US009329194B2

(12) United States Patent
Fritchie et al.

(10) Patent No.: US 9,329,194 B2
(45) Date of Patent: May 3, 2016

(54) AUTOMATED ANALYZER FOR CLINICAL LABORATORY

(75) Inventors: Patrick P. Fritchie, Southlake, TX (US); Gregory E. Gardner, Grapevine, TX (US); Richard W. Mahoney, Grapevine, TX (US)

(73) Assignee: ABBOTT LABORATORIES, Abbott Park, IL (US)

(*) Notice: Subject to any disclaimer, the term of this patent is extended or adjusted under 35 U.S.C. 154(b) by 0 days.

(21) Appl. No.: 13/550,240

(22) Filed: Jul. 16, 2012

(65) Prior Publication Data

US 2012/0282684 A1      Nov. 8, 2012

Related U.S. Application Data

(62) Division of application No. 12/257,495, filed on Oct. 24, 2008, now Pat. No. 8,222,048.

(60) Provisional application No. 60/985,373, filed on Nov. 5, 2007.

(51) Int. Cl.
*G01N 21/64* (2006.01)
*G01N 21/31* (2006.01)
*G01N 35/02* (2006.01)
*B01L 3/00* (2006.01)
*G01N 35/00* (2006.01)

(52) U.S. Cl.
CPC ............ *G01N 35/028* (2013.01); *B01L 3/5085* (2013.01); *G01N 35/0098* (2013.01); *G01N 2035/00564* (2013.01); *Y10T 436/11* (2015.01); *Y10T 436/113332* (2015.01); *Y10T 436/2575* (2015.01)

(58) Field of Classification Search
None
See application file for complete search history.

(56) References Cited

U.S. PATENT DOCUMENTS 4,275,149 A   6/1981   Litman et al.
4,649,116 A   3/1987   Daty et al.
(Continued)

FOREIGN PATENT DOCUMENTS

DE   3841961   6/1990
EP   254051    8/1994
(Continued)

OTHER PUBLICATIONS

European Patent Office, Office Communication issued for European Patent Application No. EP08847881.3, on Jul. 7, 2013, (3 pages).
(Continued)

*Primary Examiner* — P. Kathryn Wright
(74) *Attorney, Agent, or Firm* — Hanley, Flight & Zimmerman, LLC

(57) ABSTRACT

A laboratory automation system that is capable of carrying out clinical chemistry assays, immunoassays, amplification of nucleic acid assays, and any combination of the foregoing, said laboratory automation system employing at least one of micro-well plates and deep multi-well plates as reaction vessels. The use of micro-well plates as reaction vessels enables the laboratory automation system to assume a variety of arrangements, i.e., the laboratory automation system can comprise a variety of functional modules that can be arranged in various ways. In order to effectively carry out immunoassays by means of micro-well plates, a technique known as inverse magnetic particle processing can be used to transfer the product(s) of immunoassays from one micro-well of a micro-well plate to another.

22 Claims, 57 Drawing Sheets

(56) References Cited

U.S. PATENT DOCUMENTS

| | | |
|---|---|---|
| 4,804,519 A | 2/1989 | Sainz et al. |
| 4,971,913 A | 11/1990 | Manabe et al. |
| 5,082,631 A | 1/1992 | Lenmark, Sr. et al. |
| 5,358,691 A | 10/1994 | Clark et al. |
| 5,417,922 A | 5/1995 | Markin et al. |
| 5,427,743 A | 6/1995 | Markin |
| 5,578,270 A | 11/1996 | Reichler et al. |
| 5,580,524 A | 12/1996 | Forrest et al. |
| 5,589,137 A | 12/1996 | Markin et al. |
| 5,604,130 A | 2/1997 | Warner et al. |
| 5,700,427 A | 12/1997 | Ghaed et al. |
| 5,795,784 A | 8/1998 | Arnquist et al. |
| 5,817,458 A | 10/1998 | King et al. |
| 5,856,194 A | 1/1999 | Arnquist et al. |
| 5,936,527 A | 8/1999 | Isaacman et al. |
| 5,942,124 A | 8/1999 | Tuunanen |
| 5,959,738 A | 9/1999 | Hafeman et al. |
| 6,020,211 A | 2/2000 | Tuunanen |
| 6,040,192 A | 3/2000 | Tuunanen |
| 6,065,605 A | 5/2000 | Korpela et al. |
| 6,074,615 A | 6/2000 | Lewis et al. |
| 6,090,545 A | 7/2000 | Wohlstadter et al. |
| 6,117,397 A | 9/2000 | Antonenko et al. |
| 6,188,476 B1 | 2/2001 | Hafeman et al. |
| 6,197,575 B1 | 3/2001 | Griffith et al. |
| 6,202,829 B1 | 3/2001 | Van Dyke, Jr. et al. |
| 6,207,463 B1 | 3/2001 | Tuunanen |
| 6,267,927 B1* | 7/2001 | Pomar Longedo et al. ..... 422/65 |
| 6,277,332 B1 | 8/2001 | Sucholeiki |
| 6,309,889 B1 | 10/2001 | Cutlet et al. |
| 6,338,802 B1 | 1/2002 | Bodner et al. |
| 6,343,690 B1 | 2/2002 | Britton et al. |
| 6,353,774 B1 | 3/2002 | Goldenberg et al. |
| 6,409,925 B1 | 6/2002 | Gombinsky et al. |
| 6,436,349 B1 | 8/2002 | Carey et al. |
| 6,447,729 B1 | 9/2002 | Tuunanen |
| 6,448,092 B1 | 9/2002 | Tuunanen |
| 6,468,810 B1 | 10/2002 | Korpela |
| 6,498,037 B1 | 12/2002 | Carey et al. |
| 6,555,062 B1 | 4/2003 | Lewis et al. |
| 6,596,162 B2 | 7/2003 | Tuunanen |
| 6,691,748 B1 | 2/2004 | Tajima |
| 6,818,392 B2 | 11/2004 | Lou et al. |
| 6,938,504 B2 | 9/2005 | Camenisch |
| 7,033,543 B2 | 4/2006 | Panzer et al. |
| 7,169,355 B1 | 1/2007 | Shin et al. |
| 7,169,362 B2 | 1/2007 | Toi et al. |
| 7,178,416 B2 | 2/2007 | Whelan et al. |
| 7,208,125 B1 | 4/2007 | Dong |
| 7,273,759 B2 | 9/2007 | Coffman et al. |
| 7,274,294 B2 | 9/2007 | Heinze et al. |
| 7,275,682 B2 | 10/2007 | Excoffier et al. |
| 7,276,369 B2 | 10/2007 | Kosak |
| 7,300,628 B2 | 11/2007 | Nogawa et al. |
| 7,309,603 B2 | 12/2007 | Ma et al. |
| 7,338,249 B1 | 3/2008 | Zanon |
| 7,338,635 B2 | 3/2008 | Miyake et al. |
| 7,341,691 B2 | 3/2008 | Tamura et al. |
| 7,341,865 B1 | 3/2008 | Norris et al. |
| 7,390,460 B2 | 6/2008 | Osawa et al. |
| 7,541,001 B2 | 6/2009 | Kraemer et al. |
| 7,544,330 B2 | 6/2009 | Ryle |
| 7,556,770 B2 | 7/2009 | Justin et al. |
| 7,556,771 B2 | 7/2009 | Nakamura et al. |
| 7,597,848 B1 | 10/2009 | Ameling et al. |
| 7,610,941 B2 | 11/2009 | Kubacki |
| 7,700,298 B2 | 4/2010 | Wissel |
| 2001/0022948 A1 | 9/2001 | Tuunanen |
| 2001/0048899 A1 | 12/2001 | Marouiss et al. |
| 2002/0009391 A1 | 1/2002 | Marquiss et al. |
| 2002/0106814 A1* | 8/2002 | Matsubara et al. ........ 436/180 |
| 2002/0107642 A1 | 8/2002 | Nishida et al. |
| 2002/0197722 A1 | 12/2002 | Fichera et al. |
| 2003/0069699 A1 | 4/2003 | Ekins et al. |
| 2004/0018611 A1 | 1/2004 | Ward et al. |
| 2004/0022677 A1 | 2/2004 | Wohlstadter et al. |
| 2004/0071599 A1 | 4/2004 | Rusch et al. |
| 2004/0241011 A1 | 12/2004 | Yagi et al. |
| 2004/0241044 A1 | 12/2004 | Mordekhay |
| 2004/0248093 A1 | 12/2004 | Coombs et al. |
| 2005/0175506 A1 | 8/2005 | Matsubara et al. |
| 2005/0205673 A1 | 9/2005 | Morris et al. |
| 2005/0220675 A1 | 10/2005 | Reed et al. |
| 2005/0247782 A1 | 11/2005 | Ambartsoumian |
| 2006/0121602 A1 | 6/2006 | Hoshizaki et al. |
| 2006/0210435 A1* | 9/2006 | Alavie et al. .................... 422/65 |
| 2007/0036686 A1 | 2/2007 | Hatamian et al. |
| 2007/0059205 A1 | 3/2007 | Ganz et al. |
| 2007/0065811 A1 | 3/2007 | Keizer et al. |
| 2007/0077648 A1 | 4/2007 | Okamoto et al. |
| 2007/0086878 A1 | 4/2007 | Stanley et al. |
| 2007/0120685 A1 | 5/2007 | Morris et al. |
| 2007/0122912 A1 | 5/2007 | Sandell |
| 2007/0125836 A1 | 6/2007 | McAllister et al. |
| 2007/0150219 A1 | 6/2007 | Cawker et al. |
| 2007/0154356 A1 | 7/2007 | Modavis |
| 2007/0154358 A1 | 7/2007 | Dong |
| 2007/0172393 A1 | 7/2007 | Beer |
| 2007/0178012 A1 | 8/2007 | Ferrante et al. |
| 2007/0255506 A1 | 11/2007 | Lobban et al. |
| 2007/0255756 A1 | 11/2007 | Satomura et al. |
| 2008/0019878 A1 | 1/2008 | Trump |
| 2008/0020467 A1 | 1/2008 | Barnes et al. |
| 2008/0024301 A1 | 1/2008 | Fritchie et al. |
| 2008/0031781 A1 | 2/2008 | Rasnow et al. |
| 2008/0047368 A1 | 2/2008 | Marziali et al. |
| 2008/0050279 A1 | 2/2008 | Fujita |
| 2008/0056942 A1 | 3/2008 | Arima et al. |
| 2008/0063562 A1 | 3/2008 | Hoover et al. |
| 2008/0063563 A1 | 3/2008 | Watari |
| 2008/0115567 A1 | 5/2008 | Laing et al. |
| 2008/0118967 A1 | 5/2008 | Korpela et al. |
| 2008/0156114 A1 | 7/2008 | Justin et al. |
| 2008/0156117 A1 | 7/2008 | Londo et al. |
| 2008/0158543 A1 | 7/2008 | Puskas et al. |
| 2008/0175756 A1 | 7/2008 | Justin et al. |
| 2008/0175760 A1 | 7/2008 | Justin et al. |
| 2008/0193334 A1 | 8/2008 | Ryan et al. |
| 2008/0240898 A1 | 10/2008 | Manz et al. |
| 2009/0007703 A1 | 1/2009 | Angus et al. |
| 2009/0117004 A1 | 5/2009 | Fritchie et al. |
| 2009/0130745 A1 | 5/2009 | Williams et al. |
| 2009/0142231 A1 | 6/2009 | Shibuya et al. |
| 2009/0202390 A1 | 8/2009 | Iizumi et al. |
| 2009/0277286 A1 | 11/2009 | Kubacki |
| 2010/0203573 A1* | 8/2010 | Heinonen et al. ............... 435/29 |

FOREIGN PATENT DOCUMENTS

| | | |
|---|---|---|
| EP | 0915341 | 5/1999 |
| EP | 787296 | 3/2001 |
| EP | 2305348 | 4/2001 |
| EP | 788602 | 8/2001 |
| EP | 681700 | 11/2001 |
| EP | 1215502 | 6/2002 |
| EP | 0720747 | 7/2002 |
| EP | 1341611 | 9/2003 |
| EP | 1422650 | 5/2004 |
| EP | 1443329 | 8/2004 |
| EP | 1531328 | 5/2005 |
| EP | 1145010 | 6/2005 |
| EP | 1266694 | 9/2005 |
| EP | 1726362 | 11/2006 |
| EP | 1772736 | 4/2007 |
| EP | 1854541 | 11/2007 |
| EP | 1867998 | 12/2007 |
| EP | 1918721 | 5/2008 |
| EP | 2022736 | 2/2009 |
| GB | 2431600 | 5/2007 |
| JP | 58102161 | 6/1983 |
| JP | 59040167 | 3/1984 |
| JP | 59116044 | 7/1984 |
| JP | 5081715 | 2/1993 |
| JP | 7270428 | 10/1995 |

(56) References Cited

FOREIGN PATENT DOCUMENTS

| | | |
|---|---|---|
| JP | 08506661 | 7/1996 |
| JP | 08506789 | 7/1996 |
| JP | 2002535143 | 10/2002 |
| JP | 2003/329696 | 11/2003 |
| JP | 2004510161 | 4/2004 |
| JP | 2005523692 | 8/2005 |
| JP | 2005321408 | 11/2005 |
| JP | 2006526407 | 11/2006 |
| JP | 4208864 | 1/2007 |
| JP | 2007/111654 | 5/2007 |
| WO | 8705536 | 9/1987 |
| WO | 8800695 | 1/1988 |
| WO | 92/05448 | 4/1992 |
| WO | 9211538 | 7/1992 |
| WO | 9418565 | 8/1994 |
| WO | 95/01919 | 1/1995 |
| WO | 9501919 | 1/1995 |
| WO | 9508774 | 3/1995 |
| WO | 9612961 | 5/1996 |
| WO | 9845679 | 10/1998 |
| WO | 00/45164 | 8/2000 |
| WO | 0045164 | 8/2000 |
| WO | 02/08769 | 1/2002 |
| WO | 0227316 | 4/2002 |
| WO | 03/090897 | 11/2003 |
| WO | 2004/108270 | 12/2004 |
| WO | 2005044460 | 5/2005 |
| WO | 2005059929 | 6/2005 |
| WO | 2005/098454 | 10/2005 |
| WO | 2005/098455 | 10/2005 |
| WO | 2005/109332 | 11/2005 |
| WO | 2005/124366 | 12/2005 |
| WO | 2006/015012 | 2/2006 |
| WO | 2006/024392 | 3/2006 |
| WO | 2006/060125 | 6/2006 |
| WO | 2006/078714 | 7/2006 |
| WO | 2007/002580 | 1/2007 |
| WO | 2007/011844 | 1/2007 |
| WO | 2007/024540 | 3/2007 |
| WO | 2007/038521 | 4/2007 |
| WO | 2007/045341 | 4/2007 |
| WO | 2007/054718 | 5/2007 |
| WO | 2007/080230 | 7/2007 |
| WO | 2007/127516 | 11/2007 |
| WO | 2007/132526 | 11/2007 |
| WO | 2007/149628 | 12/2007 |
| WO | 2008/007923 | 1/2008 |
| WO | 2008007923 | 1/2008 |
| WO | 2008/024483 | 2/2008 |

OTHER PUBLICATIONS

Kwon, J. et al., "Performance Evaluation of Three Automated Human Immunodeficiency Virus Antigen-Antibody Combination Immunoassays," Journal of Virological Methods, 133 (Apr. 2006), 20-26, 7 pages.

Rodella, A. et al., "Quantitative Analysis of HBsAg, IgM anti-HBc and anti-HBc avidity in acute and chronic hepatitis B," Journal of Clinical Virology 37 (Nov. 2006), 206-212, 7 pages.

Kwon, J. et al., "Performance Evaluation of Three Automated Human Immunodeficiency Virus Antigen-Antibody Combination Immunoassays," Journal of Virological Methods, 133 (Apr. 2006), 7 pages.

Rodella, A. et al., "Quantatative Analysis of HBsAg, IgM anti-HBc and Anti-HBc Avidity in Acute and Chronic Hepatitis B," Journal of Clinical Virology, 37 (Nov. 2006), 7 pages.

Fang, X. et al., "Automation of Nucleic Acid Isolation on KingFisher Magnetic Particle Processors," XP-002517862, The Association for Library Automation, Aug. 2007, 7 pages.

Canadian Office Action, issued by the Canadian Intellectual Property Office, in connection with Canadian patent application No. 2,704,682 on Aug. 25, 2014, 4 pages.

European Office Action, issued by the European Patent Office in connection with European Patent Application 10166320.1, on Nov. 5, 2014, 3 pages.

Kellard, et al., "Automation of Cell-Based and Noncell-Based Permeability Assays," Journal of the Association for Laboratory Automation, Apr. 2007, 7 pages.

Fang et al. "Automation of Nucleic Acid Isolation on KingFisher Magnetic Particle Processors, Xp-002517862," the Association for Laboratory Automation, doi:10.1016/j.jala.2007.05.001, Aug. 2007, 7 pp.

"KingFisher™ Micro-well User Manual," Revision 1.0, Catalog No. 1507730, Apr. 9, 1994, 18 pages.

"KingFisher™ Software User Manual," Revision 1.0, Catalog No. 1508540, Nov. 2001, 38 pages.

"KingFisher™ mL User Manual," Revision 1.0, Catalog No. 1508260, Feb. 2002, 6 pages.

Hitachi Review. "Total Clinical Testing Laboratory System for Laboratory Automation," vol. 41 (1992), No. 4, 7 pages.

Molecular Devices, "SpectraMax M5/M5e Microplate Reader," retrieved from [URL:http://www.moleculardevices.com/pages/instruments/spectramax_m5.html,] May 6, 2009, 7 pages.

"Polymerase Chain Reaction," Wikipedia, the free encyclopedia, retrieved from [URL: http://en.wikipedia.org/wiki/polymerase_chain_reaction], Apr. 17, 2009, 13 pages.

Thermo Electron Corporation, "The KingFisher Family," Brochure, retrieved from [URL: http://www.thermo.com/eThermo/CMA/PDFs/Various/File_31157.pdf,] on Oct. 25, 2007, 2006, 6 pages.

"Thermal Cycler" Wikipedia, the free encyclopedia, retrieved from [URL: http://en.wikipedia.org/wiki/Thermocycler,] Apr. 17, 2009, 1 page.

Thermo Scientific,"KingFisher Flex purification automate," retrieved from [URL: http://www.thermo.com/com/cda/product/detail/1,,1136240,00.html,] Apr. 17, 2009, 3 pages.

PCT International application No. PCT/US2008/081494, International Search Report, Jul. 17, 2009, 5 pages.

PCT International application No. PCT/US2008/081494, Written Opnion of the International Searching Authority, May 5, 2010, 6 pages.

European Search Report, issued by the European Patent Office in connection with European Patent Application No. 10166320.1-2113, on Jan. 27, 2011, 5 pages.

European Office Action, issued by the European Patent Office in connection with European Patent Application No. 10166320.1-2113, on Feb. 16, 2012, 3 pages.

European Office Action, issued by the European Patent Office in connection with European Patent Application No. 10166320.1-2113, on Sep. 7, 2012, 3 pages.

European Office Action, issued by the European Patent Office in connection with European Patent Application No. 08847881.3-2113, on Dec. 20, 2011, 3 pages.

English Translation of Notification of Reasons for Rejection, issued by the Japanese Intellectual Property Office in connection with Japanese Patent Application No. JP2010532187, on Jul. 30, 2013, 5 pages.

Restriction, issued by the United States Patent and Trademark Office in connection with U.S. Appl. No. 12/257,495, on Mar. 28, 2011, 7 pages.

Office Action, issued by the United States Patent and Trademark Office in connection with U.S. Appl. No. 12/257,495, on May 3, 2011, 14 pages.

Final Office Action, issued by the United States Patent and Trademark Office in connection with U.S. Appl. No. 12/257,495, on Nov. 25, 2011, 15 pages.

Notice of Allowance and Fee(s) Due, issued by the United States Patent and Trademark Office in connection with U.S. Appl. No. 12/257,495, on Mar. 8, 2012, 9 pages.

English Translation of Notification of Reason(s) for Rejection, issued by the Japanese Intellectual Property Office in connection with Japanese Patent Application No. JP2010-532187, on Nov. 6, 2012, 4 pages.

(56) References Cited

OTHER PUBLICATIONS

Corkin et al., "Experiment Manager Software for an Automated Chemistry Workstation, Including a Scheduler for Parallel Experimentation," Department of Chemistry, Carnegie Mellon University, Chemometrics and Intellegent Laboratory Systems: Laboratory Information Management, 1992, 28 pages.

Communication pursuant to Article 94(3) EPC, issued by the European Patent Office in connection with European Patent Application 08 847 881.3, on Mar. 25, 2015, 3 pages.

Canadian Office Action, issued by the Canadian Intellectual Property Office, in connection with Canadian patent application No. 2,704,682, on Apr. 8, 2015, 3 pages.

communication Pursuant to Article 94(3) EPC, issued by the European Patent Office in connection with European Patent Application 10166320.1, on Feb. 3, 2016, 3 pages.

Summons to Attend Oral Proceedings Pursuant to Rule 115(1) EPC, issued by the European Patent Office in aonnection with European Patent Application 08847881.3, on Mar. 15, 2016, 3 pages.

\* cited by examiner

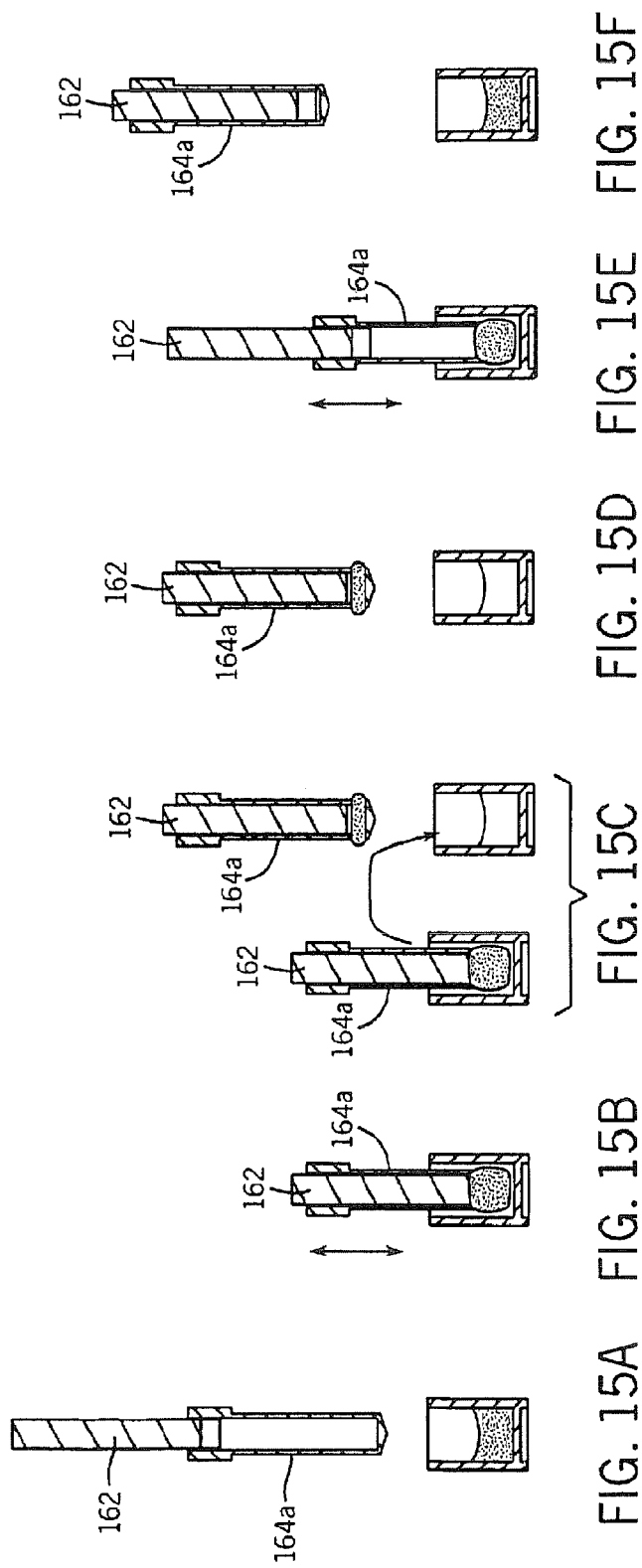

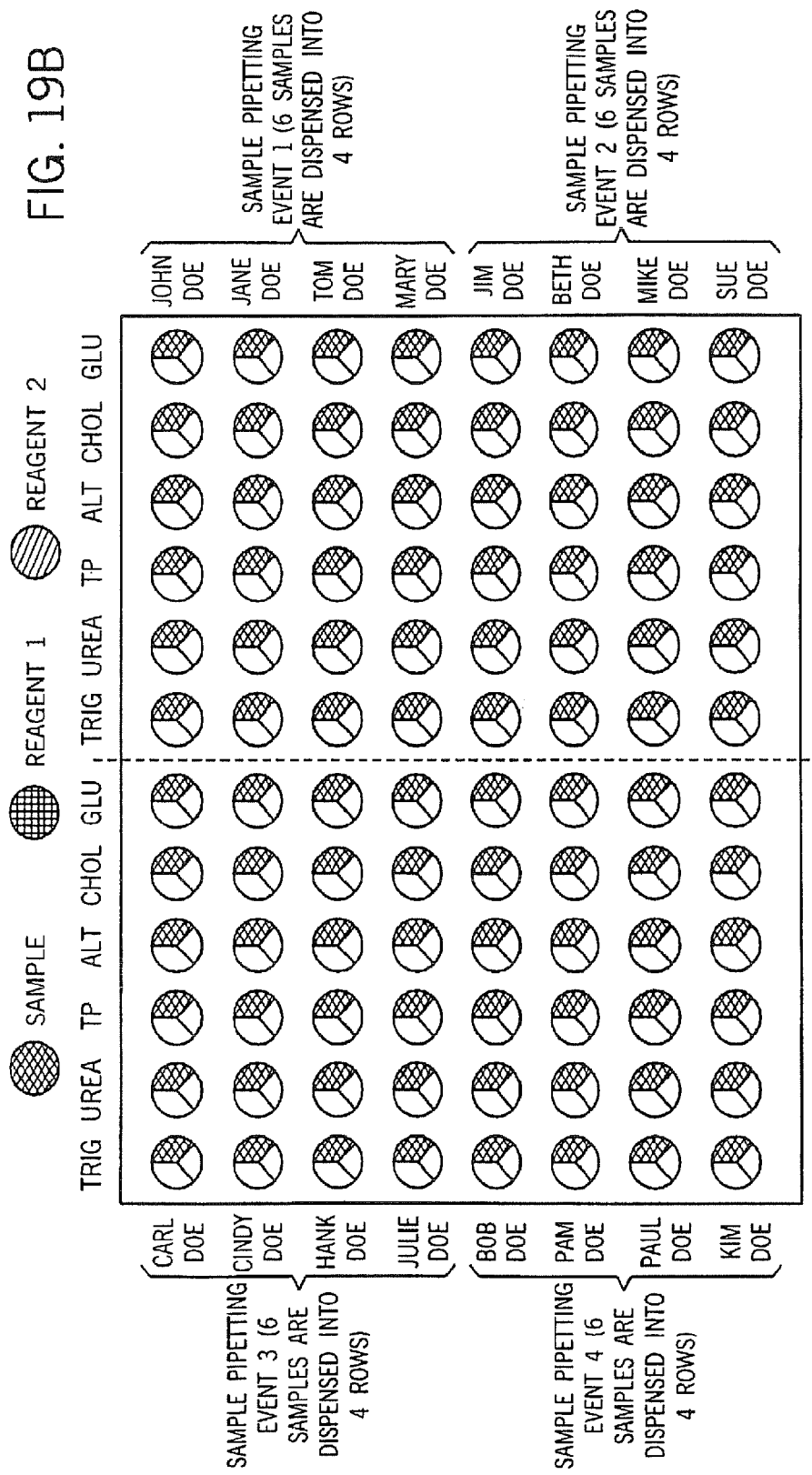

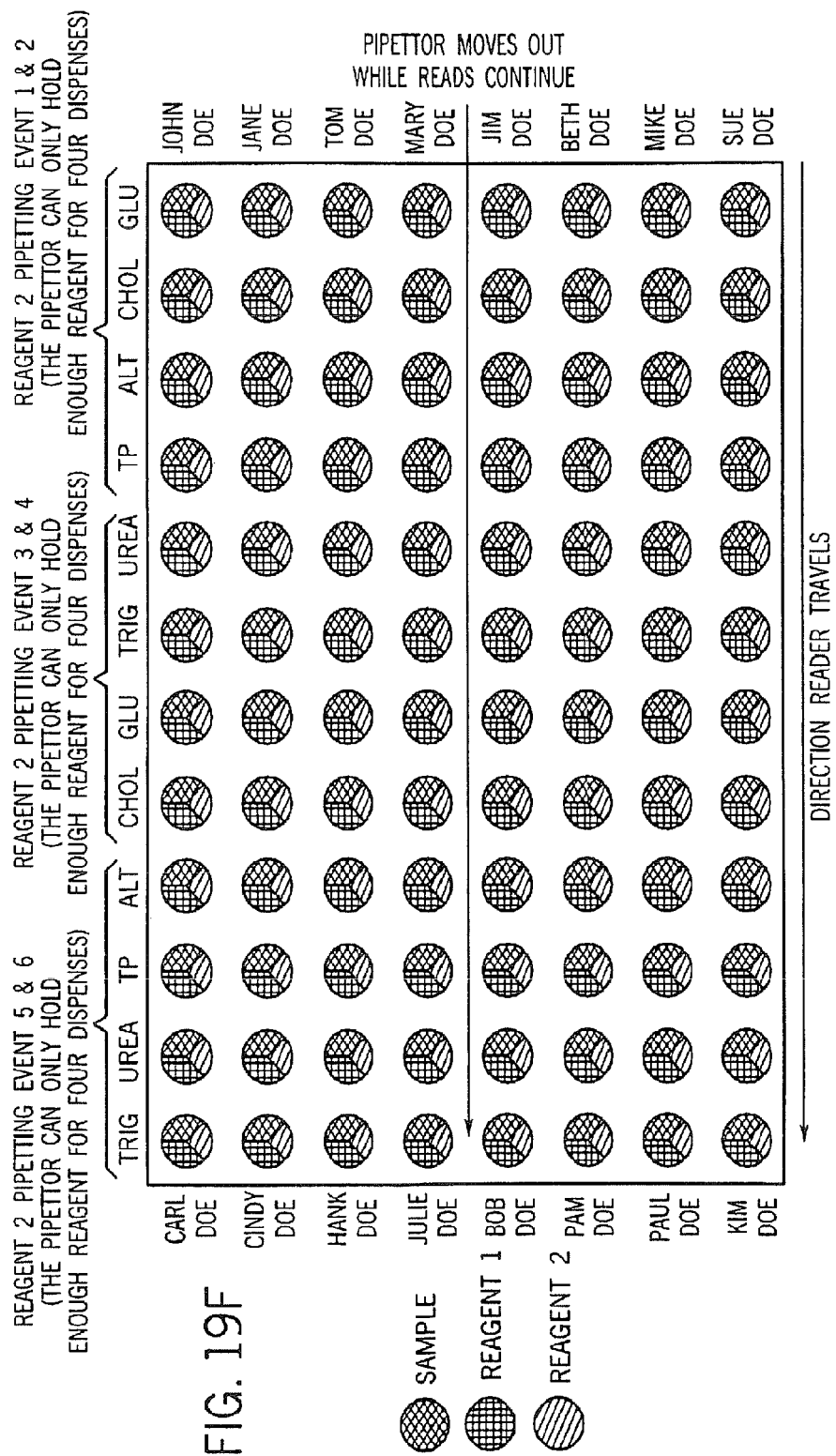

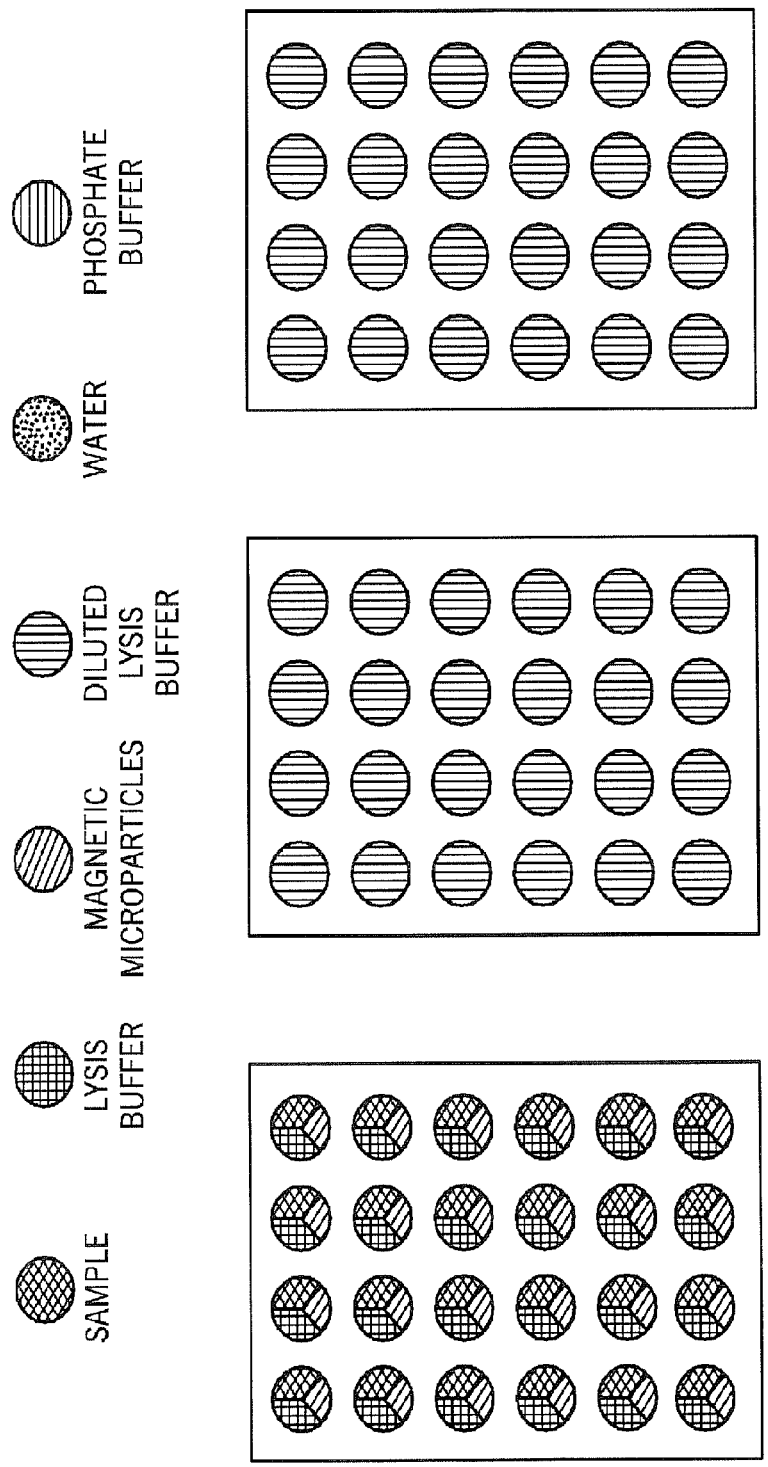

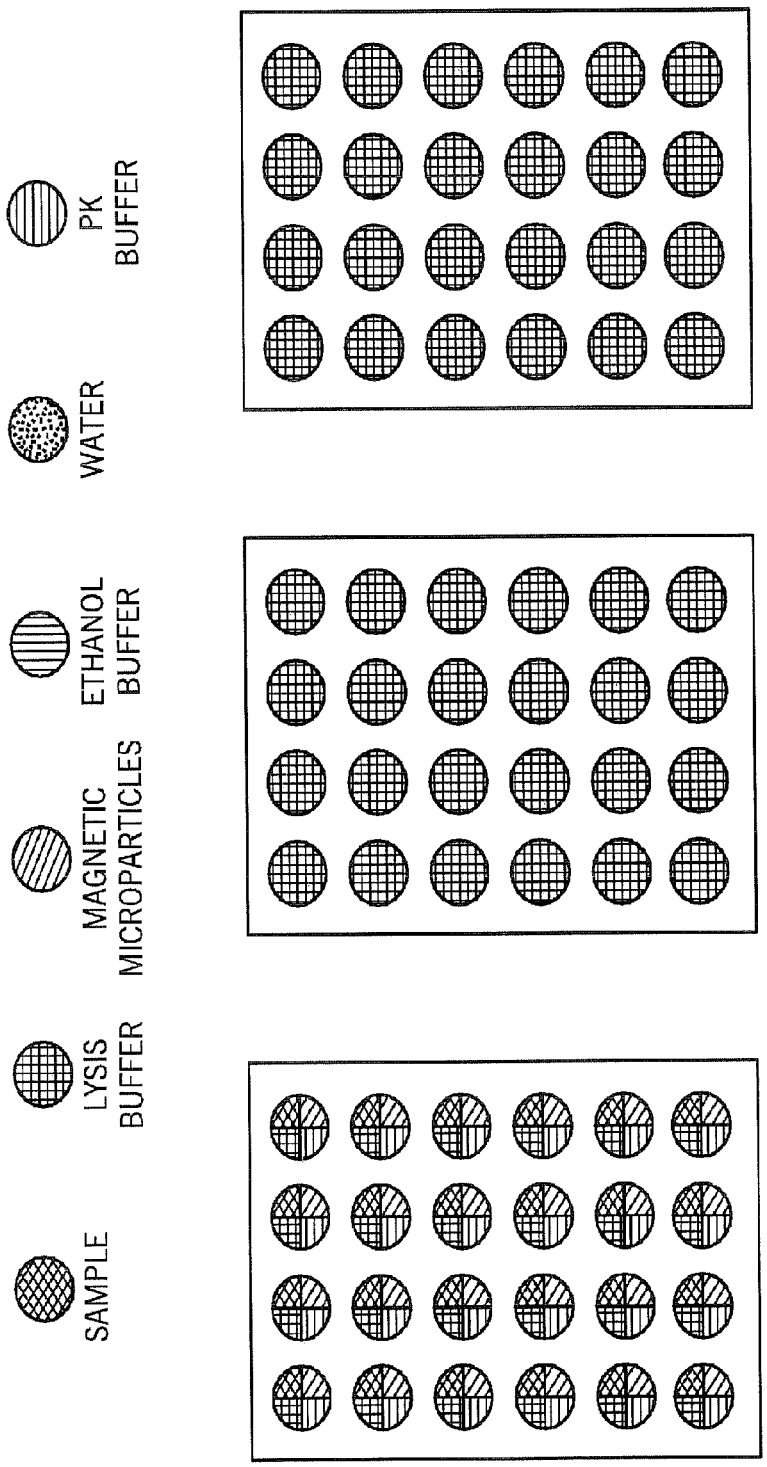

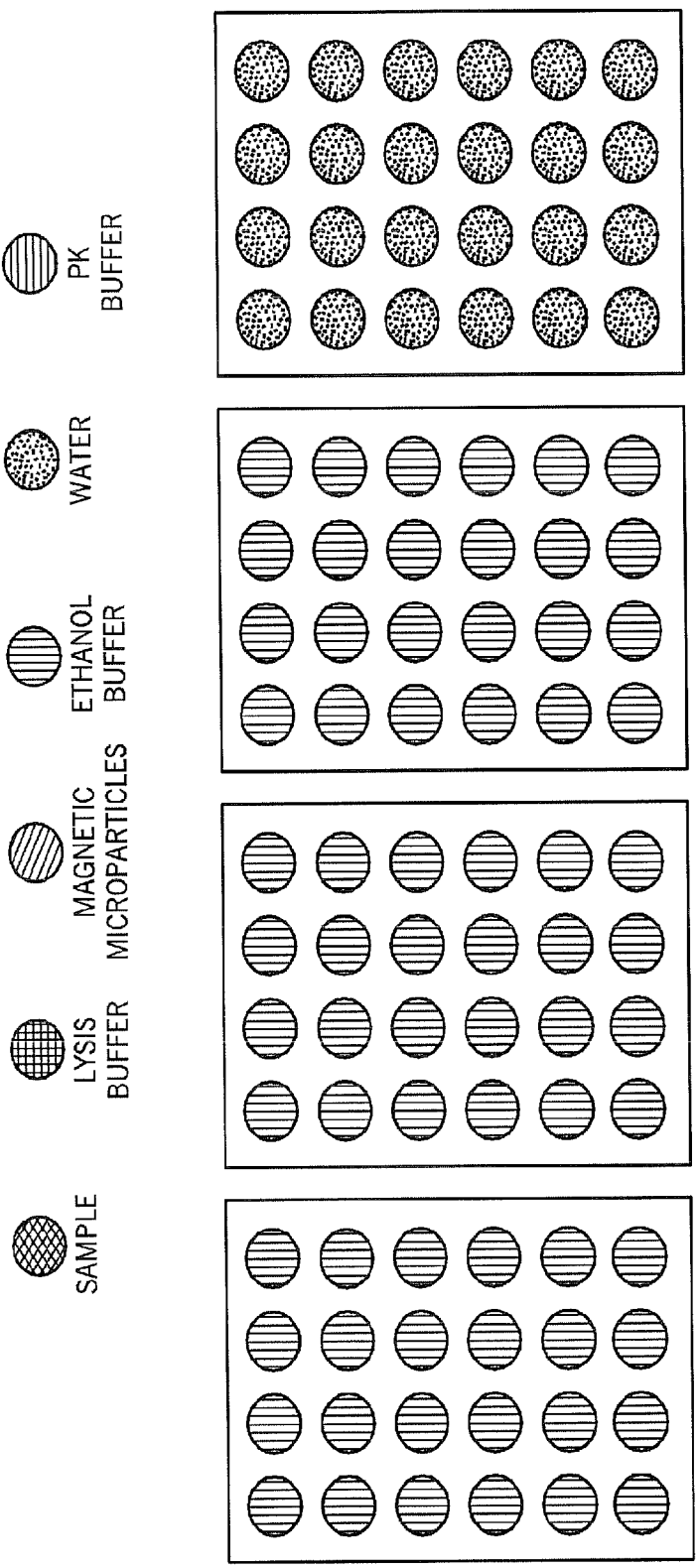

AUTOMATED ANALYZER FOR CLINICAL LABORATORY

RELATED APPLICATIONS

This patent is a divisional of U.S. patent application Ser. No. 12/257,495, which was filed on Oct. 24, 2008 and which claims priority from U.S. Provisional Application Ser. No. 60/985,373, which was filed Nov. 5, 2007, both of which are hereby incorporated by reference in their entireties.

BACKGROUND

1. Field of Disclosure

This disclosure relates to automated analyzers for clinical laboratories, more particularly, automated analyzers that can carry out analyses in the fields of clinical chemistry and immunochemistry.

2. Discussion of the Art

Automated analyzers are well-known in the field of clinical chemistry and in the field of immunochemistry. Representative examples of such automated analyzers include, but are not limited to, PRISM®analyzers, AxSym® analyzers, ARCHITECT® analyzers, all of which are commercially available from Abbott Laboratories, Cobas® 6000, commercially available from Roche Diagnostics, Advia, commercially available from Siemens AG, Dimension Vista, commercially available from Dade Behring Inc., Unicel® DxC600i, commercially available from Beckman Coulter Inc., and VITROS, commercially available from Ortho-Clinical Diagnostics. Each of these analyzers suffers from various shortcomings, some more than others. Some of the shortcomings encountered by more than one of these automated analyzers include the use of large volumes of sample, the use of large volumes of reagents, the generation of large volumes of liquid waste and solid waste, and high costs. Some of the aforementioned automated analyzers are not designed so as to be able to carry out both clinical chemistry assays and immunoassays. Some of the aforementioned automated analyzers are not capable of being modified to suit the demands of certain users. For example, even if a user desires to have more immunoassay reagents on an analyzer and fewer clinical chemistry reagents on the analyzer, or vice versa, the user cannot modify the configuration. Furthermore, the addition of additional immunoassay modules and/or clinical chemistry modules to increase throughput is difficult, if not impossible. Some of the aforementioned automated analyzers require a great deal of maintenance, both scheduled and unscheduled. In addition, some of the aforementioned automated analyzers have scheduling protocols for assays that cannot be varied, i.e., the assay scheduling protocols are fixed, which limits such features as throughput. For example, modification of current assay protocols or addition of new assay protocols may be difficult, if not impossible. The ARCHITECT® analyzers currently in use can only support six variants of chemiluminescent microparticle immunoassay protocols. In addition, some of the aforementioned analyzers occupy a great deal of floor space and consume large quantities of energy.

Users of automated analyzers desire the automated analyzers to have a minimal effect on laboratory operations, i.e., occupancy of small areas of floor space, reduction of quantities of liquid waste and solid waste, reduction of quantities of reagents and samples used, capability of interacting with existing laboratory information management systems, and simplification of ordering of consumable items. Users of automated analyzers further desire more automation of processes, i.e., greater integration of immunoassays with clinical chemistry assays, automated loading of reagents, automated loading of other consumable items, automated removal of waste, and automated maintenance. Users of automated analyzers still further desire safer and more reliable apparatus, i.e., minimal quantity of unexpected failures, minimal downtime, minimal time required to diagnose and repair unexpected failures. Users of automated analyzers still further desire more trustworthy apparatus, i.e., consistent results across a plurality of interconnected analyzers, internal checks for verifying all assay processing steps, and self-diagnosing apparatus. Users of automated apparatus further desire quiet apparatus and environmentally friendly apparatus.

SUMMARY

In one aspect, this invention provides a laboratory automation system that is capable of carrying out clinical chemistry assays, immunoassays, and both clinical chemistry assays and immunoassays. The laboratory automation system employs micro-well plates as reactions vessels. The use of micro-well plates as reaction vessels enables the laboratory automation system to assume a variety of arrangements, i.e., the laboratory automation system can comprise a variety of functional modules that can be arranged in various ways. In order to effectively carry out immunoassay reactions by means of micro-well plates, a technique known as inverse magnetic particle processing can be used to transfer the product(s) of immunoassay reactions from one micro-well of a micro-well plate to another. In one embodiment of inverse magnetic particle processing, the product(s) of an immunoassay reaction can be transferred from a first micro-well of a micro-well plate to a second micro-well of the micro-well plate, then from the second micro-well of the micro-well plate to a third micro-well of the micro-well plate, and so forth, up to an eighth micro-well of the micro-well plate, the eight micro-wells being in the same column of the micro-well plate having twelve columns, with eight micro-wells per column. According to this embodiment, twelve immunoassays can be carried out simultaneously. In another embodiment of inverse magnetic particle processing, the products(s) of immunoassay reactions can be transferred from the 96 micro-wells of a first micro-well plate to the 96 micro-wells of a second micro-well plate, then from the 96 micro-wells of the second micro-well plate to the 96 micro-wells of a third micro-well plate, and so forth, up to the 96 micro-wells of an eighth micro-well plate. According to this embodiment, 96 immunoassays can be carried out simultaneously.

The current ARCHITECT® CMIA (chemiluminescent microparticle immunoassay) protocol can be expanded to utilize 2 mL of sample by harvesting the analyte/antigen across 10 wells having a volume of 200 µL each. The ARCHITECT® CMIA protocol can be expanded to perform a homogeneous protocol by adding reagents without performing separation and wash.

The method and apparatus described herein can be used to carry out homogeneous assays, because the magnetic particle processing apparatus can be used without a separation step, i.e., the sample and the reagents can merely be mixed, allowed to react, and the separation step used in a heterogeneous assay can merely be eliminated.

In another aspect, this invention provides a method for carrying out immunoassays and clinical chemistry assays with the laboratory automation system described herein. A number of automated protocols can be employed to carry out immunoassays and clinical chemistry assays. These automated protocols include, but are not limited to, such process steps as addition of samples to reactions vessels, addition of reagents to reaction vessels, mixing of the contents of reactions vessels, incubation of reactants in reactions vessels, separating reaction products, and washing reaction products. A number of aspirating/dispensing protocols can be employed to carry out immunoassays and clinical chemistry assays. These aspirating/dispensing protocols involve kitting micro-well plates by means of a schedule not constrained by a fixed protocol. Fixed protocols are commonly utilized in conventional automated clinical laboratory analyzers. In other words, the method of this invention removes limitations upon the order of addition of reagents. In addition, the kitting protocol is not constrained by limitations relating to addition of reagents. Kitting can be carried out prior to the entry of a micro-well plate into a magnetic particle processing apparatus. The protocols eliminate the limitations inherent in the use of a carousel of an automated clinical laboratory analyzer into which conventional sample containers and conventional reagent containers are loaded by an operator. Protocols can be changed with simple updates of software files. Kitting reagents prior to performance of an assay eliminates the requirement for synchronous addition of reagents that is an inherent feature associated with a protocol that requires a device having steps of fixed intervals, such as, for example, a carousel or a process path. Devices for aspirating/dispensing can be used for kitting both immunoassays and clinical chemistry assays. The aspirating/dispensing protocols enable devices for aspirating/dispensing to be used for dispensing samples and reagents for clinical chemistry assays while immunoassays are being carried out. When the device for aspirating/dispensing is not being used for a step of an immunoassay, the device for aspirating/dispensing can be used to carry out the step of a clinical chemistry assay, and vice versa.

This invention provides a novel scheduling system for immunoassays and clinical chemistry assays that enables clinical chemistry assays to be carried out between immunoassays and immunoassays to be carried out between clinical chemistry assays.

In the laboratory automation system described herein, sample containers, reagent containers, and micro-well plates can be lifted, transported, and lowered by a device normally used for aspirating/dispensing. Pipettes of the aspirating/dispensing device can be equipped with gripping devices that can grip and transfer sample containers, reagent containers, and micro-well plates from one position to another. The gripping devices can be equipped with projections to bring about higher pressure against the sample containers, reagent containers, and micro-well plates. In the case of cylindrical containers, surfaces that conform to the cylindrical shape of the container can be adhered to the gripping devices to enable the cylindrical containers to be more readily gripped and transferred from one location to another.

The method described herein includes a method of reading information from labels. According to this method, radio frequency identification tags, conforming to the guidelines of ISO 14443 or ISO 15693 and ISO 18000, are positioned on the items of interest, such as, for example, reagent containers, sample containers, and micro-well plates. These tags can be read by and written to by either a moving antenna of a radio frequency identification reader or a stationary antenna of a radio frequency identification reader. Reading of radio frequency identification tags and writing to radio frequency identification tags are controlled by software. The use of radio frequency identification technology provides faster and more reliable readings than do barcodes, and further eliminates the hazards associated with laser scanning devices. The system described herein enables tracking of micro-well plates from the initial dispensing of samples and reagents to the final reading of results from the plates.

In the laboratory automation system described herein, troughs for holding bulk reagents can be employed. The use of troughs for holding bulk reagents enables aspirating/dispensing devices having a plurality of pipettes to aspirate and dispense reagents at a high rate of throughput.

In the laboratory automation system described herein, storage of sample containers, storage of reagent containers, transfer of sample containers, transfer of reagent containers, refrigeration of samples in sample containers, and refrigeration of reagents in reagent containers can be effected with little difficulty. Reagent containers and sample containers can be transferred from a refrigerated storage area to the analysis section of the laboratory automation system by an automated robotic mechanism.

The laboratory automation system described herein provides a user-friendly graphical user interface for enabling an operator to closely control and monitor numerous immunoassays and/or clinical chemistry assays. The graphical user interface can utilize fuel gauge-type liquid level indicators to simplify reading of liquid levels in containers. The graphical user interface can utilize instructional balloons to instruct relatively inexperienced operators in proper usage of the laboratory automation system.

The laboratory automation system and method described herein result in improved sensitivity of assays, reduction of assay processing resources, and improved reliability. In addition, the laboratory automation system and method described herein improve flexibility of assay processing resources, whereby new assays and new assay protocols can be accommodated with minimal effect upon the design of the laboratory automation system.

In the method and apparatus described herein, the physical arrangement of the micro-wells in the micro-well plates along with the coloration of the micro-wells in the micro-well plates enables efficient collection of photons when luminescence readers are used. In the prior art, when a cuvette and a photomultiplier tube are used for luminescence readings, the collection of photons is not efficient on account of the geometry of the cuvette and the geometry of the photomultiplier tube. Many chemiluminescent readers currently used to read results of immunoassays collect photons from the side of a translucent cuvette. A small portion of the photons emitted from the "sphere of light" enters into a light pipe and eventually arrive at the photomultiplier tube, where they are counted. Reflection of photons from a translucent cuvette is not possible. By using appropriately colored micro-wells within a micro-well plate, a large portion of the photons created a chemiluminescent reaction are reflected upwards, directly into the photomultiplier tube, which is focused on the contents of the micro-well.

Because the volume of a micro-well is lower than the volume of a cuvette, the volume of reagents consumed is reduced. Similarly, the volume of the sample consumed is reduced. Also, the quantity of liquid waste is reduced. On account of the design of the system described herein, a reaction vessel loader is not needed, washing mechanisms are not required, and in-track vortexers are not required. In-track vortexers are vertically movable mixers located underneath the track of a conventional analyzer that utilize fixed interval steps for moving reactions vessels, e.g., a carousel or a process path. After a reagent is dispensed into a reaction vessel, the vertically movable mixers are used to provide mixing of contents within the reaction vessel, typically by means of nutator rotators.

The apparatus and method described herein greatly simplifies the apparatus and method needed to carry out immunoassays and clinical chemistry assays. Only a single XYZ pipette is required, rather than a plurality of pipettes. By dispensing samples in rows and reagents in columns of a micro-well plate, or vice versa, pipettes can dispense a plurality of aliquots of samples or a plurality of aliquots of reagents without the need for filling the pipette until all of the aliquots are dispensed, thereby both reducing the time needed to move a pipette to and from a sample container and the time needed to move a pipette to and from a reagent container. Process path diverters, which are used in some automated clinical laboratory analyzers, are not required. Fewer mechanical parts are required to process reactions carried out in micro-wells of micro-well plates, thereby improving the reliability of the laboratory automation system. Positive displacement pumps that are actuated by a stepper motor for dispensing controlled amounts of liquids are not required. Conventional analyzers use positive displacement pumps for washing tips of probes and directly dispensing diluents, wash buffer, and pre-trigger solutions.

The apparatus and method described herein enable immunoassays to be integrated with clinical chemistry assays, using many of the same resources, such as, for example, pipettes, kitting stations, fluidics, refrigeration equipment, controllers, power supply, capable of being used for both types of assays. Other types of assay formats, such as, for example, fluorescent polarization immunoassay (FPIA) format can be added to the laboratory automation system.

The apparatus and method described herein also enable extraction of nucleic acids from a biological sample and amplification of the nucleic acids thus extracted to be integrated with immunoassays and clinical chemistry assays, using many of the same resources, such as, for example, pipettes, kitting stations, fluidics, refrigeration equipment, controllers, power supply, capable of being used for all three types of assays.

In the apparatus and method described herein, maintenance procedures for cleaning washing stations, track systems, and other components are not necessary. Priming and flushing of fluidics systems are not necessary. Manual loading of reagents and samples can be eliminated by using automated systems. In addition, ordering of reagents and other consumable items can be automated by means of a reagent inventory management system, which can communicate with on-line order entry systems available from many vendors.

Micro-well plates can be tracked by means of radio frequency identification, while conventional reaction vessels cannot be so tracked. Many commercially available sub-systems are available to process micro-well plates, which allows the user to incorporate improvements, delay obsolescence, transfer accounts for vendors who go out of business.

BRIEF DESCRIPTION OF THE DRAWINGS

FIG. 1 shows both a track system and a position where the analysis section of the laboratory automation system can be located.

FIG. 2 depicts components that can be positioned adjacent to the track system shown in FIG. 1.

FIGS. 15A, 15B, 15C, 15D, 15E, and 15F are schematic diagrams illustrating a basic process that can utilize the principles of a KingFisher™ magnetic particle processor to process immunoassay reactions.

In FIG. 16A, the micro-wells contain a mixture of the sample and magnetic microparticles. In FIGS. 16B, 16C, 16E, and 16F, the micro-wells contain wash buffer. In FIG. 16D, the micro-wells contain conjugate. In FIG. 16G, the micro-wells contain pre-trigger solution.

FIGS. 19A, 19B, 19C, 19D, 19E, and 19F are sequential top plan views of a single micro-well plate illustrating the dispensing of samples and reagents for six clinical chemistry assays for 16 patients.

In FIG. 23, the analysis section has three levels. This type of analysis section is served by a robotic system that can travel both horizontally and vertically and a single aspiration/dispensing device.

FIGS. 25A, 25B, 25C, 25D, 25E, and 25F are top plan views illustrating six deep well multi-well plates, each well of a given deep well plate containing the same ingredient(s). This kitting of deep well multi-well plates enables 24 samples of the nucleic acid RNA to be set up for processing in a magnetic particle processor prior to undergoing an amplification reaction. In FIG. 25A, the wells contain a mixture of the sample, magnetic microparticles, and a lysis buffer. In FIGS. 25B and 25C, the wells contain diluted lysis buffer. In FIGS. 25D and 25E, the wells contain water. In FIG. 25F, the wells contain phosphate buffer.

FIGS. 26A, 26B, 26C, 26D, 26E, 26F, and 26G are top plan views illustrating seven deep multi-well plates, each well of a given deep well multi-well plate containing the same ingredient(s). This kitting of deep well multi-well plates enables 24 samples of the nucleic acid DNA to be set up for processing in a magnetic particle processor prior to undergoing an amplification reaction. In FIG. 26A, the wells contain a mixture of the sample, magnetic microparticles, a lysis buffer, and a PK buffer. In FIGS. 26B and 26C, the wells contain lysis buffer. In FIGS. 26D, 26E, and 25F, the wells contain ethanol buffer. In FIG. 26G, the deep wells contain water.

DETAILED DESCRIPTION

Figure 1:
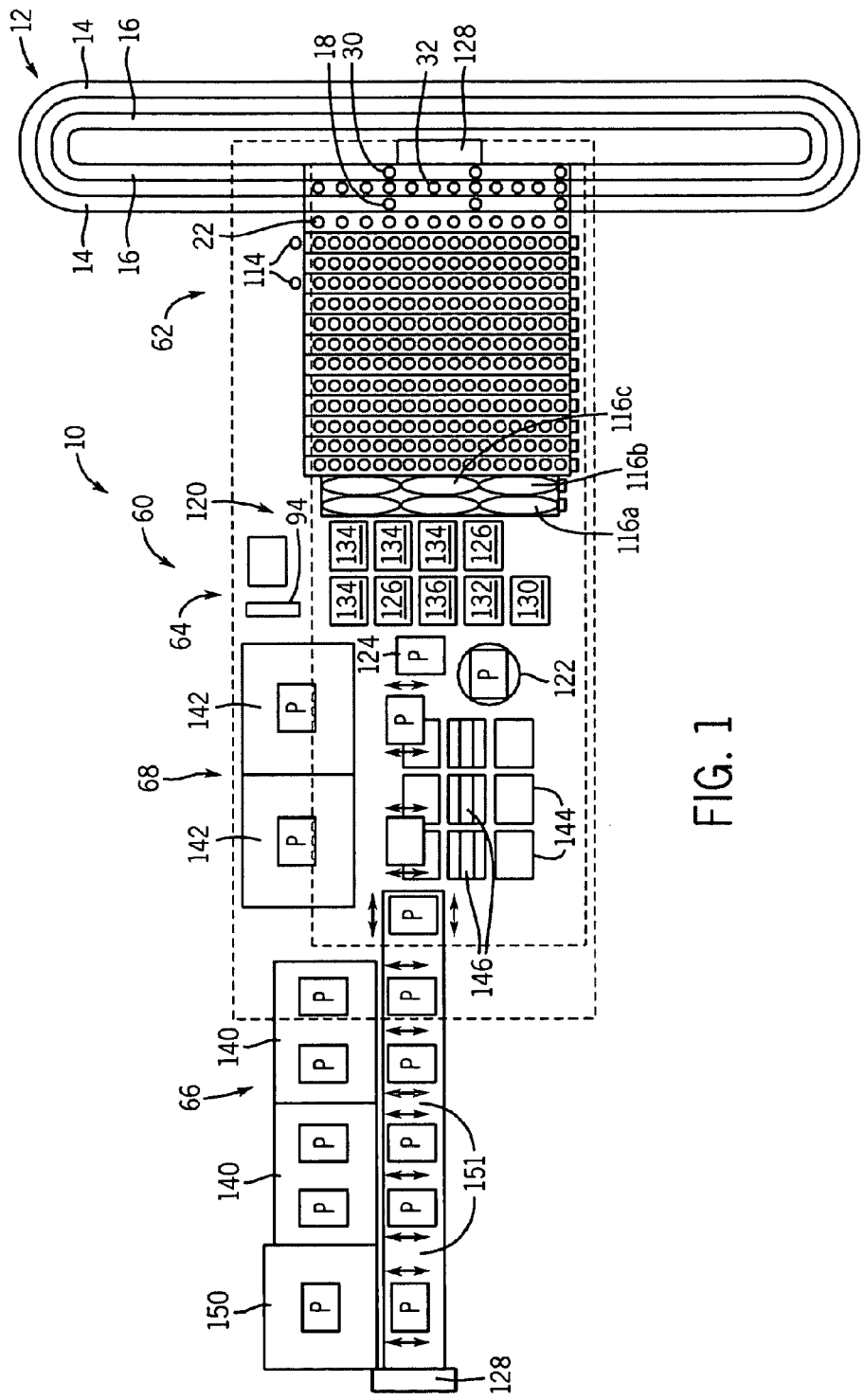
FIG. 1 is a schematic diagram illustrating one embodiment of the laboratory automation system described herein.

As used herein, the term "immunoassay" means a biochemical test that measures the concentration of a substance in a biological liquid, typically serum, using the reaction of an antibody or antibodies to its (their) antigen. An immunoassay takes advantage of the specific binding of an antibody to its antigen. As used herein, a "chemiluminescent microparticle immunoassay", alternatively referred to as "chemiluminescent magnetic immunoassay", involves a chemiluminescent label conjugated to the antibody or the antigen. In this assay, a magnetic microparticle is coated with antibodies. The assay is intended to look for antigens in the sample. A second antibody is labeled with a chemiluminescent label. This second antibody is not attached to a magnetic microparticle. The antibody and antigen with attach in the following order: antibody on magnetic microparticle-antigen-antibody-chemiluminescent label. The magnetic microparticle is then washed off. The amount of antibody-antigen-enzyme is measured by adding pre-trigger solution and trigger solution and measuring the light produced. This type of immunoassay produces light when combined with its substrate, i.e., a specific binding member. The chemiluminescent reaction offers high sensitivity and ease of measurement. This type of immunoassay involves a noncompetitive sandwich format that yields results that are directly proportional to the amount of analyte present in the sample. As used herein, the term "magnetic" means paramagnetic.

As used herein, the expression "clinical chemistry assay" means a biochemical test that measures the concentration of a substance that occurs naturally within the human body, which concentrations serves to indicate the condition or state of health of the various systems of the body. Such a substance, often referred to as an analyte, exists within certain expected ranges of concentration in a healthy human being. Chemistry analytes fall into one of three main categories, routine analytes, such as for example, lipids, nutrients, chemical constituents, metabolic products, examples of which include glucose, urea nitrogen triglycerides, uric acid, enzymes, such as, for example, alanine aminotransferase, aspartate aminotransferase, lactate dehydrogenase, and amylase, and electrolytes, such as, for example, sodium, potassium, and chloride. As used herein, the expression "laboratory automation system" means a system designed to automate the processing of samples prior to, during, and subsequent to analyzing the samples. The processing includes handling of the samples, moving the samples from a clinical analyzer to other components of the system, and storing of the samples.

As used herein, the term "sample", the expression "biological sample", and the like, mean a material suspected of containing an analyte. The sample can be used directly as obtained from the source in an assay or following a pretreatment to modify the character of the sample before undergoing an assay. The sample can be derived from any biological source, such as, for example, a physiological fluid, including, but not limited to, blood, saliva, ocular lens fluid, cerebral spinal fluid, sweat, urine, milk, ascites fluid, mucous, synovial fluid, peritoneal fluid, amniotic fluid, or the like. The sample can be pretreated prior to use, such as, for example, preparing plasma from blood, diluting viscous fluids, or the like. Methods of pretreatment can involve filtration, distillation, concentration, inactivation of interfering components, and the addition of reagents. Besides physiological fluids, other liquid samples can be used, such as, for example, water, food products, and the like. In addition a solid material suspected of containing the analyte can be used as the sample. As used herein, the term "analyte" refers to the compound or composition to be detected or measured.

As used herein, the expression "radio frequency identification" is a generic term for technologies that use radio waves to automatically identify objects, such as, for example, containers for biological samples and containers for reagents for analyzing biological samples. The most common method of identification is to store a serial number that identifies the object, and perhaps other information relating to the object or contents thereof, on a microchip that is attached to an antenna. The microchip and the antenna together are called a radio frequency identification transponder or a radio frequency identification tag. The antenna enables the microchip to transmit the identification information and other information to a radio frequency identification reader. The radio frequency identification reader converts the radio waves reflected back from the radio frequency identification tag into digital information that can then be passed on to computers that can make use of it.

As used herein, the expression "aspirating/dispensing device" means a device that has the dual functions of removing liquids from containers by suction and distributing portions of the liquids aspirated into containers, e.g., micro-wells of micro-well plates. An aspiration/dispensing device that is capable of being used for the system described herein is described in U.S. Pat. No. 7,033,543, incorporated herein by reference. As used herein, the term "pipette", also called "pipet", "pipettor", means a laboratory instrument used to transport a measured volume of liquid. As used herein, the expression "micro-well plate", also called "microtiter plate", "microplate", means a flat plate having a plurality of "wells" used as small test tubes. As used herein, the term "XYZ" refers to a device that can move in three directions, a first horizontal direction, a second horizontal direction that is perpendicular to the first horizontal direction, and a third direction that is perpendicular to both the first horizontal direction and the second horizontal direction. As used herein, the terms "re-use", "reusable", and the like, refers to a disposable item that can be used again rather than disposed of a after a single use. As used herein, the term "fixed protocol" means a protocol for carrying out an assay, wherein the beginning and ending times assigned for the incubation step(s), the beginning and ending times assigned for the mixing step(s), the beginning and ending times assigned for the reagent addition step(s), the beginning and ending times assigned for the washing step(s), and the like for other step(s), must occur at a fixed time after the assay has commenced. As used herein, the expression "analysis section of the laboratory automation system" means that portion of the laboratory automation system in which immunoassays or clinical chemistry assays or both immunoassays and clinical chemistry assays are performed. As used herein, the term "kitting" means dispensing samples and reagents in appropriate micro-wells of a micro-well plate prior to commencing chemical reactions.

As used herein, the expression "extraction of nucleic acid(s)" and the like, means removal of nucleic acid(s) from a biological sample. As used herein, the expression "amplification of nucleic acid(s)", and the like, refers to assays that use purified enzymes to isolate and then replicate specific nucleic acid(s) to levels it (they) can be detected. An example of a technique for amplification of nucleic acid(s) is polymerase chain reaction (PCR). As used herein, the expression "multi-well plate" means a plastic tray having an upper surface and a lower surface and a plurality wells depending from the lower surface of the tray, the wells capable of being filled through openings in the upper surface of the tray. The wells can be limited in size to contain a relatively small amount of liquid, e.g., less than one mL, and the multi-well plates containing the same are designated as micro-well plates. Alternatively, the wells can be expanded in size to contain a relatively large amount of liquid, e.g., greater than one mL, and the multi-well plates containing the same are merely designated as multi-well plates.

As used herein, the symbol "(s)" following the name of an item indicates that one or more of the subject items is intended, depending upon the context. As used herein, the expression "and/or" is used to indicate that either the word "and" or the word "or" can be used to connect words, phrases, or clauses.

Throughout the specification, so far as possible, like parts or components will have the same reference numerals; like parts or components may have different reference numerals when required for the sake of clarity. In addition, where necessary, a micro-well plate(s) is indicated by the letter "P". It should be noted the micro-well plates in processors and readers are not actually visible. However, the micro-well plates are inside of the processors and readers and the relative positions of the micro-well plates within the processors and readers are designated by the letter P.

Laboratory automation systems typically employ aspirating/dispensing devices wherein a pipette (or pipettes) of the aspirating/dispensing device can be moved in three dimensions, i.e., two dimensions in a horizontal plane (i.e., X and Y) and one dimension vertically (i.e., Z). The remaining components of laboratory automation systems can be placed near to or be connected with the aspirating/dispensing device to enable the pipette (or pipettes) to obtain access to various components of the laboratory automation system. However, not all components require direct access from an aspiration/dispensing device. In some cases, micro-well plates into which reagents have been dispensed can be moved out of the access range of the aspiration/dispensing device by an optional robotic mechanism and placed in an autonomous subsystem for further processing. In general, chemiluminescent microparticle immunoassays do not call for dispensing reagents after kitting has taken place. In contrast, clinical chemistry assays require dispensing reagents between readings.

Depending on the desired capabilities of the laboratory automation system, laboratory automation sub-systems (e.g., various diagnostic assay technologies) can added to or subtracted from the aspirating/dispensing device. In addition, multiple sub-systems can be added to the laboratory automation system to increase throughput, e.g., one or more immunoassay sub-systems can be added to an immunoassay sub-system to increase throughput of immunoassays, or one or more clinical chemistry assay sub-systems can be added to a clinical chemistry assay sub-system to increase throughput of clinical chemistry assays.

Figure 2:
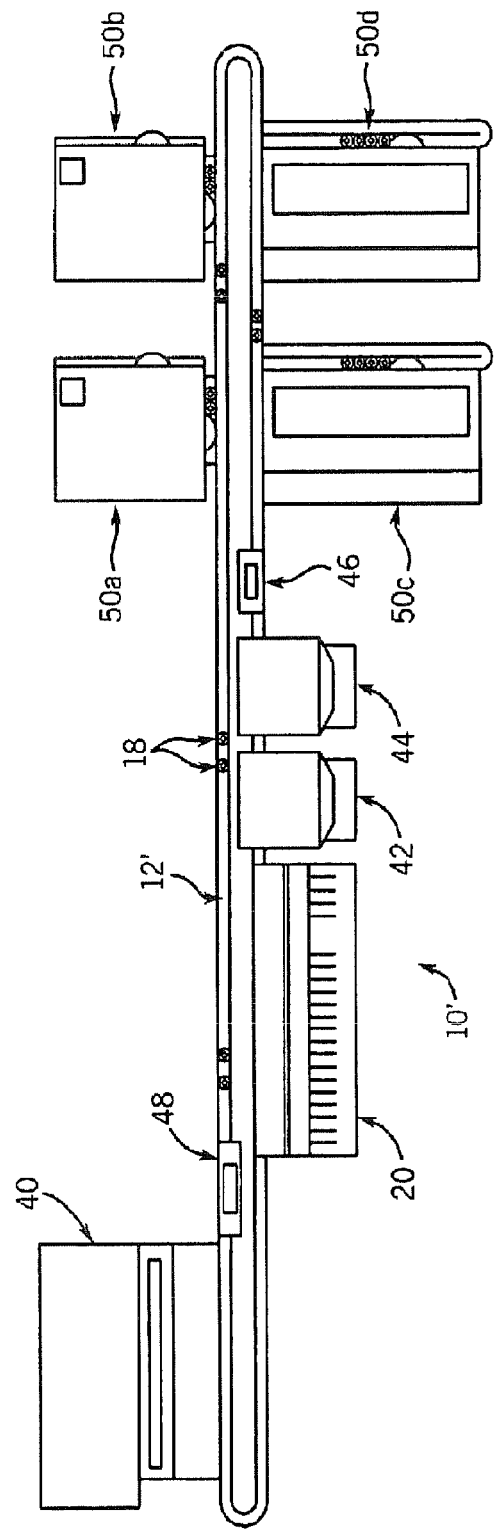
FIG. 2 is a schematic diagram illustrating a laboratory automation system currently available.

The desired components of laboratory automation systems can be positioned in numerous arrangements. FIG. 1 illustrates a laboratory automation system that can be modified for use with the system and method described herein. In this figure is shown a track arrangement for enabling the movement of containers containing samples (sample containers) and containers containing reagents (reagent containers) from an input/output module to one or more short-term storage areas for reagent containers and sample containers. Also shown in this figure is a section for positioning the analytical instruments of the laboratory automation system. FIG. 2 illustrates other conventional components of a laboratory automation system that can be placed around the track arrangement.

Figure 5:
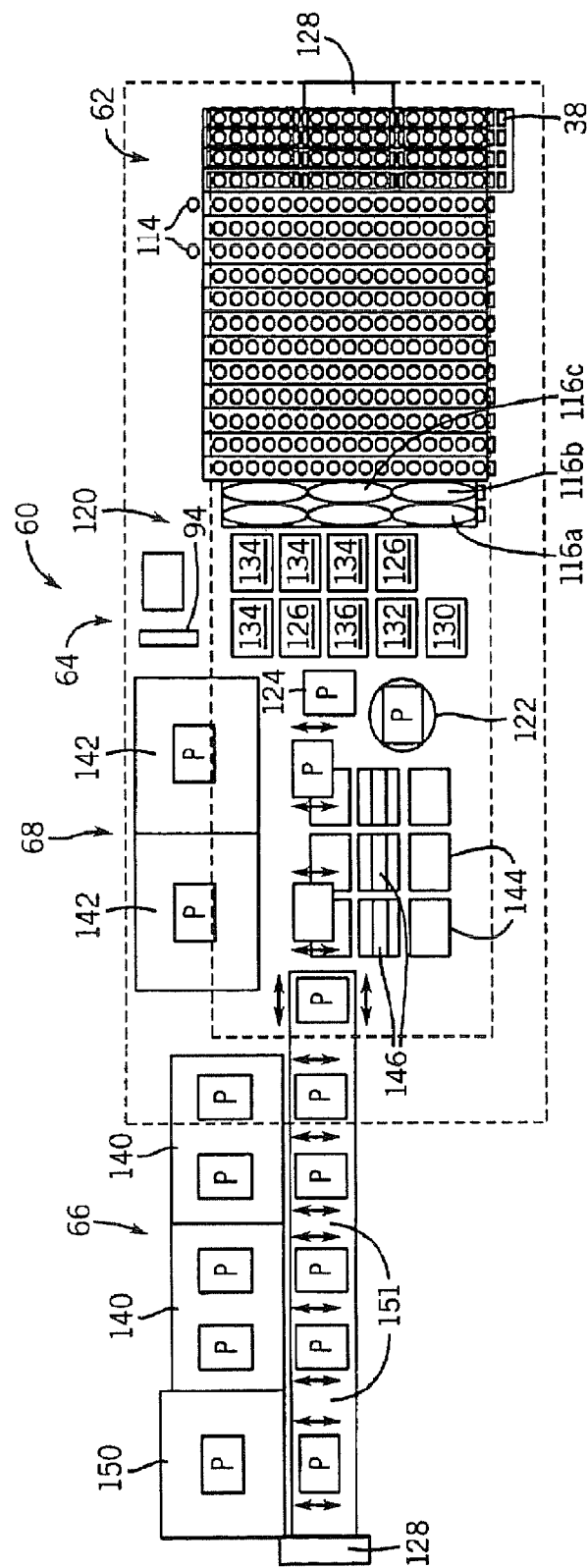
FIG. 5 is a top plan view of one embodiment of the laboratory automation system described herein. In this embodiment, the analysis section of the laboratory automation system is shown in detail. This analysis section utilizes components that integrate immunoassays with clinical chemistry assays and can perform a relatively high volume of assays per unit of time.
Figure 6:
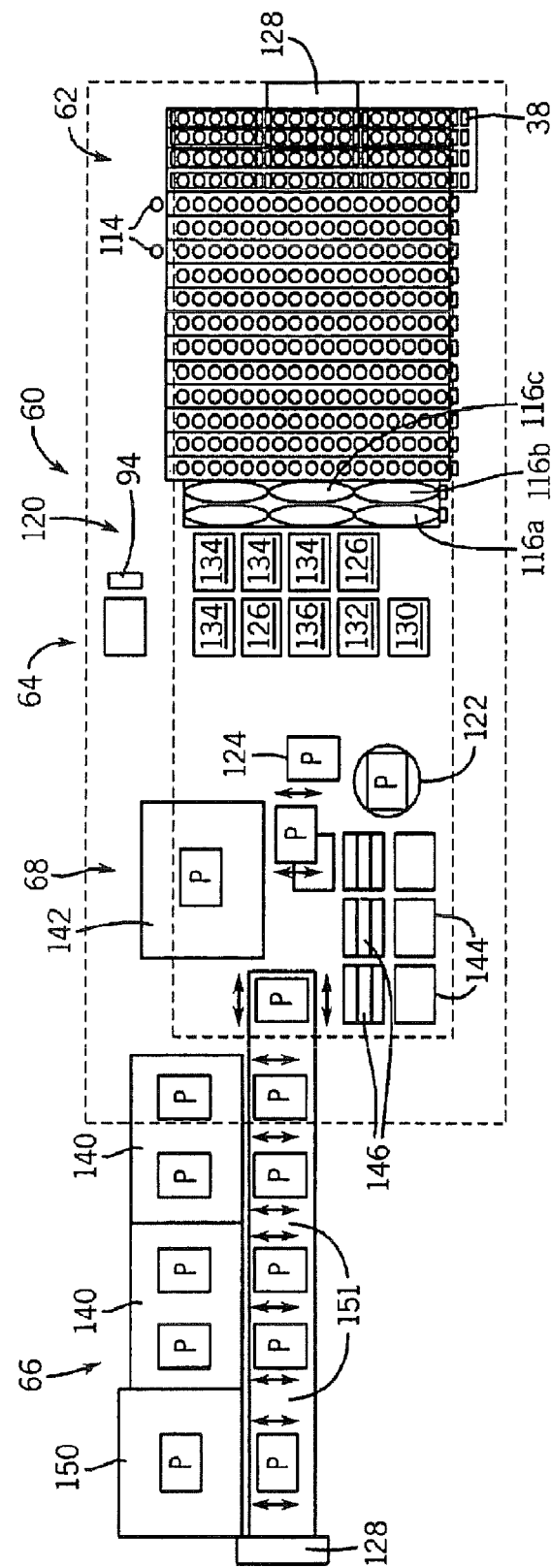
FIG. 6 is a top plan view of another embodiment of the laboratory automation system described herein. In this embodiment, the analysis section of the laboratory automation system is shown in detail. This analysis section utilizes components that integrate immunoassays with clinical chemistry assays and can perform a relatively moderate volume of assays per unit of time.
Figure 7:
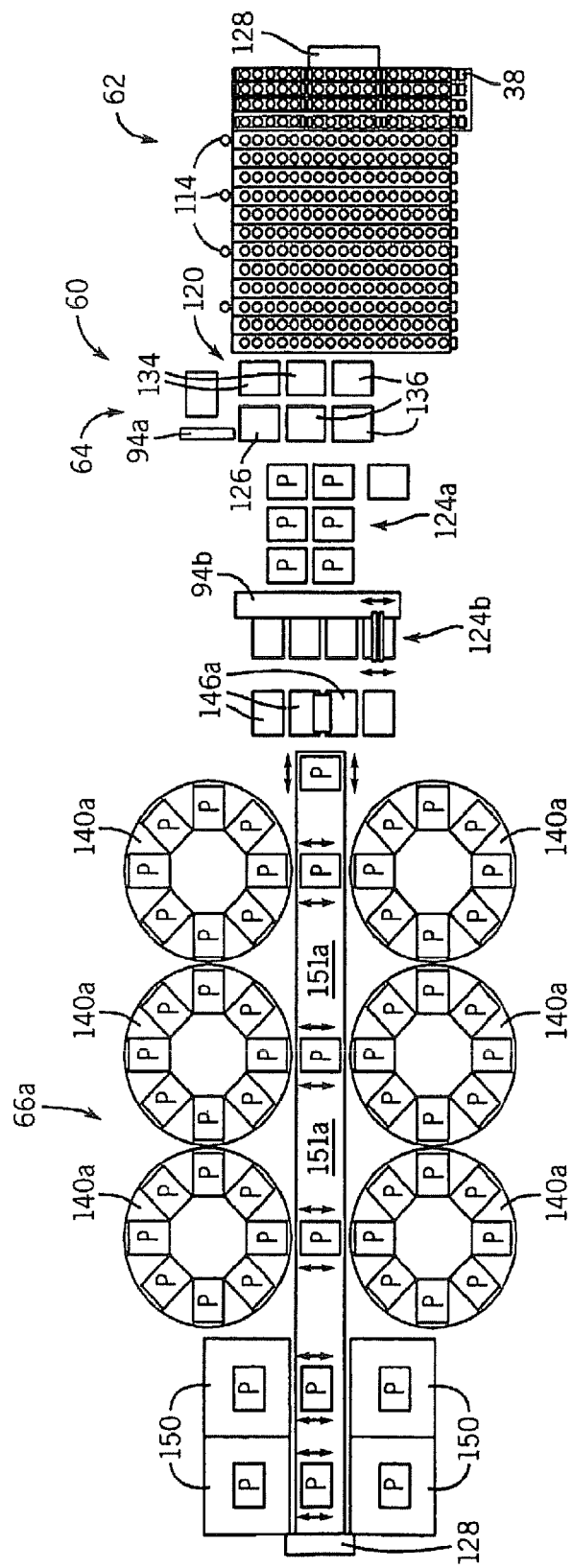
FIG. 7 is a top plan view of another embodiment of the laboratory automation system described herein. In this embodiment, the analysis section of the laboratory automation system is shown in detail. The analysis section utilizes components that perform immunoassays only. The analysis section shown can perform a very high volume of immunoassays per unit of time.
Figure 8A:
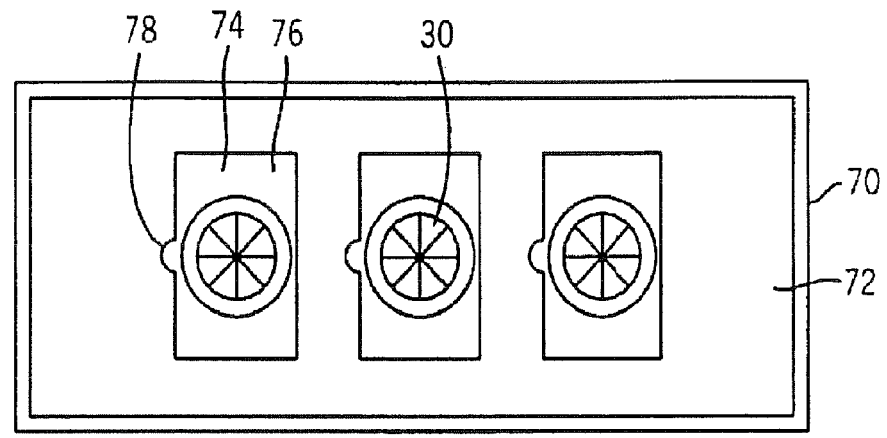
FIGS. 8A, 8B, 8C, and 8D is a schematic diagram illustrating an arrangement of sliding covers that can be used to increase the useful life of biological materials.
Figure 8B:
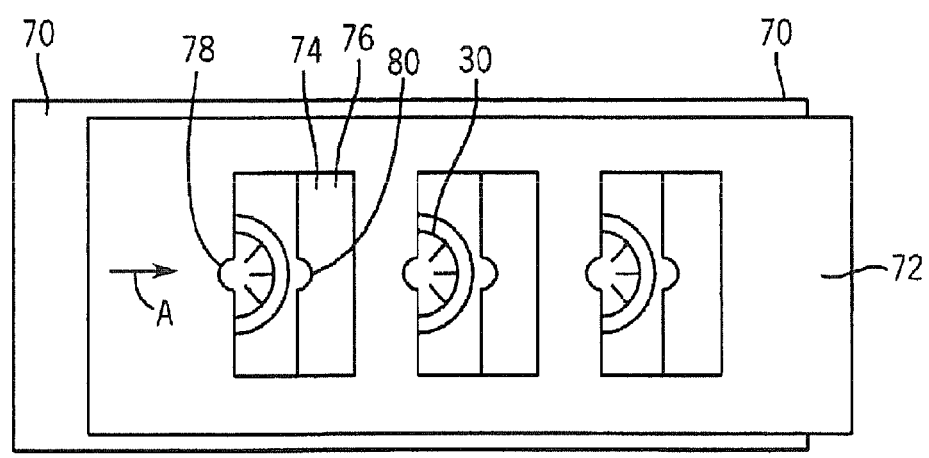
Figure 8C:
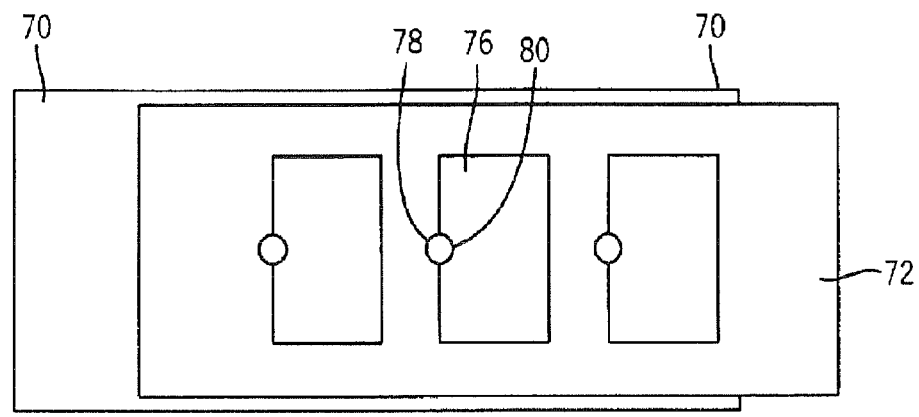
Figure 8D:
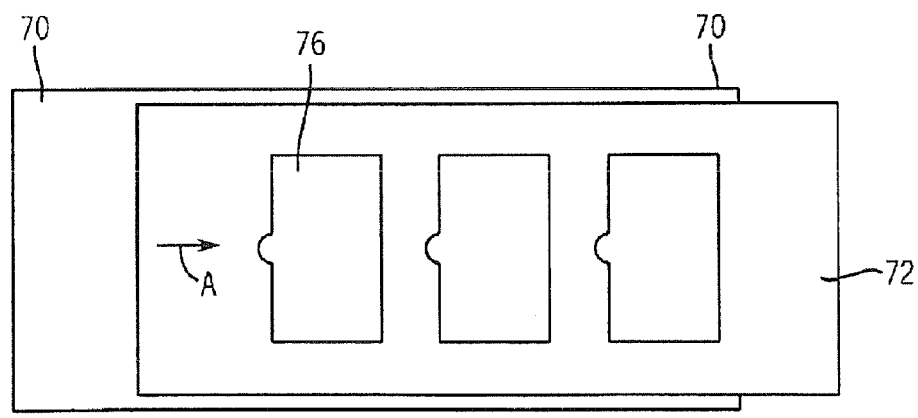

FIGS. 5, 6, and 7 illustrate three of several possible ways of arranging the components of the analysis section of the laboratory automation system, but not including the track system, which can be used with any of the arrangements shown in FIGS. 5, 6, and 7. FIGS. 5, 6, and 7 show the relative positions of such components as aspirating/dispensing devices, signal detectors, such as, for example, readers, e.g., an absorbance reader, a luminescence reader, an immunoassay processor, e.g., a chemiluminescent microparticle immunoassay (CMIA) processor, a clinical chemistry assay (CC) processor, a micro-well plate rotator, positions for storage of disposable components, positions for storage of reagents, and positions for storage of samples.

FIG. 1 shows a sub-system, i.e., an analysis section of a laboratory automation system, wherein immunoassays are integrated with clinical chemistry assays. This sub-system can also perform a relatively high number of assays per unit of time. This same sub-system is shown in FIG. 5. This sub-system enables a throughput of about 192 immunoassay tests per hour (when no clinical chemistry tests are run) or 900 clinical chemistry tests per hour (when no immunoassay tests are run) or 600 clinical chemistry tests per hour and 96 immunoassay tests per hour when both types of tests are run together. FIG. 6 shows a sub-system, i.e., an analysis section of a laboratory automation system, similar to that shown in FIGS. 1 and 5. However, the sub-system shown in FIG. 6 enables a throughput of about 96 immunoassay tests per hour (when no clinical chemistry tests are run) or 450 clinical chemistry tests per hour (when no immunoassay tests are run) or 300 clinical chemistry tests per hour and 48 immunoassay tests per hour when both types of tests are run together. FIG. 7 shows a sub-system, i.e., an analysis section of a laboratory automation system, wherein only immunoassays are carried out. However, this sub-system can perform a very high number of immunoassays per unit of time. This sub-system enables a throughput of immunoassays of about 1200 immunoassay tests per hour. Other sub-systems can be manufactured. For example, certain variations of the sub-systems shown in FIGS. 1, 5, and 6 can delete the immunoassay components. As another example, certain variations of the sub-systems shown in FIGS. 1, 5, and 6 can delete the clinical chemistry components.

Figure 3B:
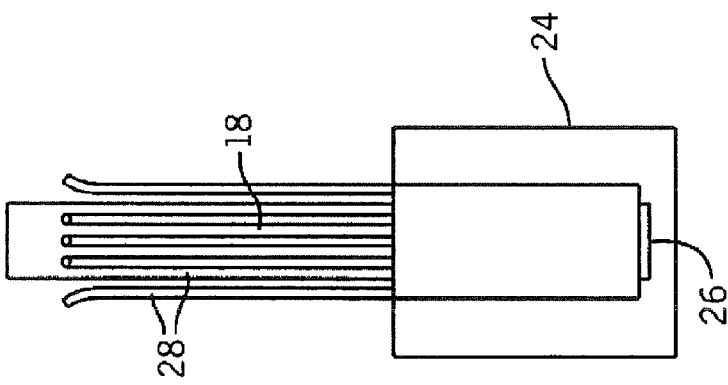
FIG. 3B is a front view in elevation illustrating a sample container in a sample container carrier having an adapter.
Figure 3A:
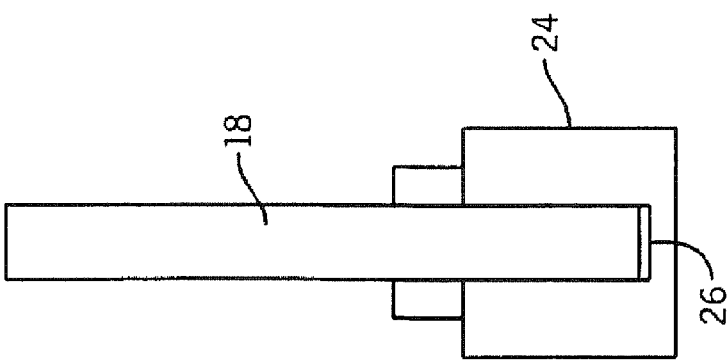
FIG. 3A is a front view in elevation illustrating a sample container in a sample container carrier.

Referring now to FIG. 1, a laboratory automation system 10 comprises a track system 12. As shown in FIG. 1, the track system 12 has a first lane 14 and a second lane 16. The purpose of the first lane 14 is to transport a container holding a sample (i.e., a sample container) 18 from an input/output module 20 (see FIG. 2) to a sample container queue 22. A sample container 18 can suitably travel over the track system 12 by means of a sample container carrier 24 (see FIGS. 3A and 3B). Sample container carriers 24 suitable for transporting sample containers 18 on a lane of a track system are commercially available from suppliers such as, for example, Inpeco S.p.a., Thermo Fisher Scientific, Inc., Beckman Coulter Inc., Lab Interlink, A&T Corporation, Siemens AG, etc. Such a sample container carrier 24 is described, for example, in U.S. Pat. Nos. 5,417,922; 5,427,743; 5,589,137; and 6,343,690, all of which are incorporated herein by reference. The sample containers 18 can be placed in sample container carriers 24 by means of a suitable robotic mechanism (not shown). The sample container carriers 24 travel along the first lane 14 of the track system 12 by means of an endless conveyor belt, or a suitable alternative thereto. Such conveyor belts, and suitable alternatives thereto, are well known to those having ordinary skill in the art. The sample container 18 or adapter sleeve 28 can be equipped with a radio frequency identification tag 26, which can be used to identify and track a given sample container 18. In an alternative embodiment of a sample container carrier 24, the sample container carrier 24 can be equipped with adapter sleeves 28, which enable the sample container carriers 24 to be the same size as reagent container carriers 34 to adapt to sample containers 18 having differing diameters or differing lengths or both of the foregoing.

Figure 4:
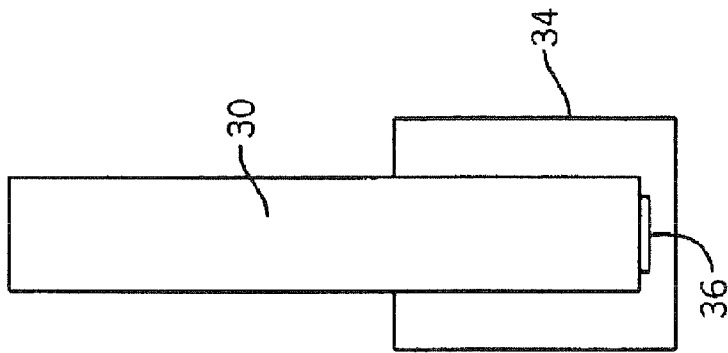
FIG. 4 is a front view in elevation illustrating a reagent container in a reagent container carrier.

The purpose of the second lane 16 is to transport a container holding a reagent (i.e., a reagent container) 30 from the input/output module 20 to a reagent container queue 32. A reagent container 30 can suitably travel over the track system 12 by means of a reagent container carrier 34 (see FIG. 4). A representative example of a reagent container carrier 34 suitable for this purpose is commercially available from Nittobo Boseki Co., Ltd. and Rexam PLC. Such a reagent container carrier 34 is described, for example, in U.S. Pat. Nos. 6,074,615 and 6,555,062, both of which are incorporated herein by reference. The reagent containers 30 can be placed in reagent container carriers 34 by means of a suitable robotic mechanism (not shown). The reagent container carriers 34 travel along the second lane 16 of the track system 12 by means of an endless conveyor belt, or a suitable alternative thereto. Such conveyor belts, and suitable alternatives thereto, are well known to those having ordinary skill in the art. The reagent container 30 can be equipped with a radio frequency identification tag 36, which can be used to identify and track a given reagent container 30. It is also possible to use the same lane of the track system 12 to transport sample container carriers 24 and reagent container carriers 34, as well as to use separate lanes for the sample container carriers 24 and the reagent container carriers 34. The use of the same lane for both sample container carriers 24 and reagent container carriers 34 could reduce the cost of the track system 12. In addition, the use of the same lane for both sample container carriers 24 and reagent container carriers 34 allows sample container carriers 24 and reagent container carriers 34 to be of the same size.

A system for managing the inventory of reagents can be designed to place reagent containers 30 into reagent container carriers 34, after which placement, these reagent container carriers 34 will be routed to the analysis section of the laboratory automation system 10, where they will be diverted into the correct local queue 32. Such placement can be effected by a robotic mechanism (not shown), which will have the capability of picking up a reagent container 30 from a storage location near the track system 12 and placing the reagent container 30 on a reagent container carrier 34. Similarly, a system for providing the samples can be designed to place sample containers 18 into sample container carriers 24 or reagent container carriers 34 having adapter sleeves 28, after which placement, these sample container carriers 24 will be routed to the analysis section of the laboratory automation system 10, where they will be diverted into the correct local queue 22. Such placement can be effected by a robotic mechanism (not shown), which will have the capability of picking up a sample container 18 from a storage location near the track system 12 and placing the sample container 18 on a sample container carrier 24 or a reagent container carrier 34 having an adapter sleeve 28.

Each analysis section of the laboratory automation system 10 will have local queues 22, 32, where the sample container carriers 24 and the reagent container carriers 34, respectively, are diverted from the track system 12 and held for processing. Diverters suitable for such a diverting purpose are well-known to those of ordinary skill in the art. A diverter is typically an electromechanically actuated gate. An example of a diverter suitable for use herein is described in U.S. Pat. No. 6,202,829, incorporated herein by reference.

The reagent containers 30 are merely removed from the reagent container carriers 34 and placed in the reagent storage area located within the analysis section of the laboratory automation system 10. The samples are aspirated from a sample container 18, which need not be removed from the sample container carrier 24. The samples can be aspirated from a given sample container 18 until all of the samples required for a testing of that sample have been removed from the sample container 18. At the completion of processing of samples or at some other appropriate time, the sample container carriers 24 and the reagent container carriers 34 are released from the local queue(s) 22, 32, and are transported to the track system 12. Empty reagent containers 30 are disposed of in solid waste containers. The sample containers 18 can be held in the sample container carrier 24 until results and/or orders determine that no retest or additional testing is required. The reagent container carriers 34 can simply be recycled for the next reagent transporting operation.

A reagent inventory management system can be added to the laboratory automation system 10 described herein. A typical reagent inventory management system includes an operator interface for the loading of boxes of reagents and other supplies, radio frequency identification system for identification of inventory and tracking, robotic mechanisms for loading containers onto the track system and removing containers from the track system, decapping equipment, refrigeration equipment, and information technology connections to laboratory analyzers and vendors.

If a track system 12 is not used to transport the sample containers 18 and the reagent containers 30 to the analysis section of the laboratory automation system 10, a sample container tray 38 that supports a plurality of sample containers 18 can be used. The laboratory automation system 10 would merely have the queues for the reagent container carriers 34 and the sample container carriers 24 replaced by a suitable support for the sample container trays 38. See, for example, FIGS. 5, 6, and 7. In these figures, the track system 12 is not shown. In place of the track system 12 are sample container trays 38. However, fittings for sample container trays 38 can be removed, and the remainder of the laboratory automation system 10 can be connected with a track system 12.

Placed at appropriate positions along the track system 12 can be various components for preparing samples, which samples are supplied in sample containers 18, for the analytical systems that will be described later. Referring now to FIG. 2, which is a commercially available laboratory automation system 10', such components that can also be used in the laboratory automation 10 described herein are positioned along the track system 12'. These components include, but are not limited to, the input/output module 20 for (a) introducing sample containers 18 to the laboratory automation system 10 and (b) removing sample containers 18 from the laboratory automation system 10, and a container storage and retrieval unit 40 for storing samples upon which a set of assays has been performed. Also shown in FIG. 1 are a first centrifuge system 42 and a second centrifuge system 44 for separating serum from cells in a sample of blood, a decapper 46 for removing caps from sample containers 18, typically caps from sample tubes, a resealer 48 for sealing the sample containers 18 after completion of analytical testing, and a refrigerator (not shown) for prolonging the useful life of biological materials, e.g., reagents, samples. The reagent containers 30 can be loaded by the operator into the refrigerator, when the reagent containers 30 are received in a shipping carton from a shipping department. This loading process may require removing the top of the shipping carton. The radio frequency identification tags 36 affixed to the reagent containers 30 can be read by a radio frequency identification reader (not shown) associated with the refrigerator and the inventory is recorded. When an analysis section of the laboratory automation system 10 connected to the system for managing the inventory of reagents requests a reagent container(s) 30, the system for managing the inventory of reagents typically removes the oldest reagent(s) of the type requested from a shipping carton in the refrigerator, i.e., in a first-in, first-out manner, prepares the reagent container(s) 30 for processing (e.g., caps are removed, septa are installed, etc.) and places the reagent container(s) 30 into reagent container carrier(s) 34. Removal of the reagent container 30 from the shipping carton and placement of the reagent container 30 into the reagent container carrier 34 can be carried out by means of a robotic mechanism (not shown). The reagent container carriers 34 holding the reagent containers 30 are then diverted onto the appropriate lane of the track system 12 and subsequently routed to the analysis section of the laboratory automation system 10 that requested the reagent(s). Eventually, empty shipping cartons are ejected from the refrigerator into a solid waste container.

Not shown in FIG. 1 but necessarily present is a control unit for handling information in the laboratory automation system 10. The control unit also provides the commands to the various robotic mechanisms, which carry out the automated functions of the laboratory automation system 10. It is expected that the control unit can be a personal computer. Additional discussion of the conventional components of a simple laboratory automation system can be found in Ikeda et al., "Total Clinical Laboratory Testing System for Laboratory Automation", Hitachi Review, Vol. 41 (1992) No. 4, pages 167-172, incorporated herein by reference. Examples of tube storage and retrieval units, input/output modules, centrifuge systems, decappers, resealers, refrigerators, and other auxiliary components are well-known to those of ordinary skill in the art and are readily commercially available from numerous sources. Also shown in FIG. 2, but not to be included in the laboratory automation system 10 described herein are a first immunoassay analyzer 50a, a second immunoassay analyzer 50b, a first clinical chemistry analyzer 50c, and a second clinical chemistry analyzer 50d. The invention described herein utilizes different types of immunoassay analyzers and different types of clinical chemistry analyzers.

A central reagent storage area (not shown) can provide a substantial inventory of reagents; these reagents can be transported to the track system 12 or the analysis section of the laboratory automation system 10 as required. Means of transportation suitable for transporting reagents from the central storage area to the input/output module 20 include, but are not limited to, gantries, endless conveyor belts, and robotic mechanisms.

Adjacent to the track system 12 is at least one analysis section 60 of the laboratory automation system 10. Depending upon the size of the track system 12, more than one analysis section 60 can be employed. The analysis section 60 has four major sub-sections, namely a sub-section 62 for retaining samples and reagents that are to be used in the assays, a sub-section 64 for retaining disposable components for the equipment needed to introduce and manipulate samples and reagents into reaction vessels, e.g., micro-well plates, a sub-section 66 for supporting instruments needed to carry out immunoassays, and a sub-section 68 for supporting instruments needed to carry out clinical chemistry assays. Sub-section 66 is not required to be directly accessible to an aspiration/dispensing device and can utilize kitted micro-well plates. Sub-section 68 generally requires an aspiration/device that has direct access to micro-well plates.

The sub-section 62 of the analysis section 60 is preferably elevated to a level sufficient to accommodate a radio frequency identification reader (not shown) for reading information from radio frequency identification tags 26, 36. Such a radio frequency identification reader is described in U.S.

application Ser. No. 11/495,430, filed Jul. 28, 2006, entitled SYSTEM FOR TRACKING VESSELS IN AUTOMATED LABORATORY ANALYZERS BY RADIO FREQUENCY IDENTIFICATION, incorporated herein by reference.

In one embodiment of implementing the radio frequency identification system for containers and carriers for containers, e.g., the sample container carriers 24 and the reagent containers 30, the radio frequency identification system includes at least one movable radio frequency identification reader. In order for the radio frequency identification reader to read the data from the radio frequency identification tag associated with a container, or with a container carrier, the radio frequency identification reader is caused to move to a position proximate to the radio frequency identification tag so that the information from the radio frequency identification tag can be read with an amount of noise and interference from nearby radio frequency identification tags on other containers, or on other container carriers, that are insufficient to adversely affect the integrity of the data read by a radio frequency identification reader. In this embodiment, a transmission sub-system must be provided to enable the at least one radio frequency identification reader to move among the containers and the carriers for the containers. A second reader, which is stationary, can be used to read the radio frequency identification tags attached to consumable items that are transported to the vicinity of the second reader.

In another embodiment, the radio frequency identification system includes at least one stationary radio frequency identification reader. In order for the at least one radio frequency identification reader to read the data from the radio frequency identification tag associated with a container, or with a container carrier, the container, or the container carrier, is caused to move to a position proximate to, and preferably in register with, the at least one radio frequency identification reader so that the information from the radio frequency identification tag can be read with an amount of noise and interference from nearby radio frequency identification tags on other containers, or on other container carriers, that are insufficient to adversely affect the integrity of the data read by a radio frequency identification reader. In this embodiment, a transmission sub-system need not be provided to enable the at least one radio frequency identification reader to move among the containers and the container carriers.

There are at least two ways to implement the foregoing embodiment of the stationary radio frequency identification reader. According to a first way, the sample containers and the reagent containers, or the sample container carriers and the reagent container carriers, can be transported to a position proximate to at least one stationary radio frequency identification reader, whereby the stationary radio frequency identification reader tags on the containers, or on the container carriers, can be read by the at least one stationary radio frequency identification reader. According to a second way, a plurality of antennas, which are traces on a printed circuit board, function as separate stationary radio frequency identification readers. These antennas can receive separate collections of data. In a preferred embodiment of a reader for reading radio frequency identification tags, a single printed circuit board has a plurality of antennas under the reagent storage area and the sample storage area. The length of the antenna is important, because the length determines the relationship with the radio frequency used. The length of the antenna corresponds to some multiple of wavelength of the radio frequency energy, e.g., one-half wavelength, one-quarter wavelength.

The printed circuit board for the radio frequency identification system can provide connections for remote antennas and a means for selecting those antennas one at a time. For example, the radio frequency identification system can have external connections for several remote reading locations, such as the micro-well plate rotator, pre-treatment area, magnetic particle processor, luminescence reader(s), absorbance reader(s), inventory reading locations, and locations on the local queue and transport track. By reading the antennas at these remote locations, a micro-well plate can be tracked throughout the laboratory automation system and provide a chain of custody.

In order to implement the radio frequency identification system described herein, a radio frequency identification tag can be positioned on the lowermost portion of a container, e.g., a reagent container 30, or on a container carrier, e.g., a sample container carrier 24. It is often desirable to position an encapsulated radio frequency identification tag on the lowermost portion of a container. In the case of sample containers 18, a radio frequency identification tag can be positioned on the sample container carrier 24.

In one embodiment, two high frequency (13.56 MHZ) radio frequency identification readers can be employed. One radio frequency identification reader is capable of moving under the area where the reagent containers are positioned. The other radio frequency identification reader, which is stationary, reads radio frequency identification tags on micro-well plates. The use of radio frequency identification readers makes it possible to efficiently and tightly pack reagent containers and sample containers 18 in the laboratory automation system 10. The use of radio frequency identification readers and radio frequency identification tags make it possible to include a higher density of data on a container, relative to the amount of data that can be applied by means of barcodes. Furthermore, if writable radio frequency identification tags are used, the data on the radio frequency identification tags can be updated to reflect changes that have taken place with respect to the contents of the containers equipped with the radio frequency identification tags. The radio frequency identification system can provide an interface to personal computer.

In the laboratory automation system 10 described herein, samples are shared for both immunoassay and clinical chemistry assay technologies. The samples can be transported to the sub-section 62 of the analysis section 60 by the track system 12 of the laboratory automation system 10 to minimize the storage of samples on the analysis section 60 of the laboratory automation system 10 and to automate retest and/or reflex testing. Alternatively, the samples can be positioned at the sub-section 62 of the analysis section 60 by other means, such as, for example, manually or, if desired, by a robotic mechanism (not shown). As discussed previously, samples can be transferred to the analysis section 60 of the laboratory automation system 10 by means of a sample container carrier 24 or by means of trays 38 that support sample containers 18. A typical sample container tray 38 can hold up to five (5) sample containers 18, a row of sample container trays can typically comprise up to three (3) sample container trays 38, and the sub-section 62 can typically hold up to twelve (12) sample container trays. While the area of the sub-section 62 of the analysis section 60 allocated for sample containers 18 is not critical, it can be seen that up to sixty (60) sample containers 18 can be stored in the sub-section 62. However, more than sixty sample containers 18 can be stored in sub-section 62 of the analysis section 60, if the dimensions of the analysis section 60 are increased.

The sub-section 62 of the analysis section 60 provides sufficient space for temporary storage for reagent containers 30 for clinical chemistry assays, temporary storage of reagent containers 30 for immunoassays, along with equipment for stirring reagents for immunoassays, and temporary storage of sample containers 18. The sub-section 62 can be designed to include reagent containers 30 for clinical chemistry assays only, reagent containers 30 for immunoassays only, or a combination of reagent containers 30 for both types of assays. The sub-section 62 is preferably equipped to provide refrigeration and evaporation control for the reagents and the samples. FIGS. 8A, 8B, 8C, and 8D illustrate a system for minimizing the exposure of reagent containers 30 to the environment. In this system, a system of sliding reagent covers 70, 72 can be used to insulate the reagent containers 30 from the exterior environment. Reagents can be preserved for longer periods of time through the use of the sliding reagent cover embodiment described herein. In this embodiment, a first sliding reagent cover 70 is positioned above a plurality of reagent containers 30 located in the sub-section 62. A second sliding reagent cover 72 is positioned above the plurality of reagent containers 30 and also above the first sliding reagent cover 70. The first sliding reagent cover 70 is substantially rectangular in shape, as is the second sliding reagent cover 72. The first sliding reagent cover 70 is inserted into a track (not shown) in which the first sliding reagent cover 70 can slide in a horizontal direction, as shown by the arrow "A". The second sliding reagent cover 72 is inserted into a track (not shown), which is in register with the track into which the first sliding reagent cover 70 is inserted, in which the second sliding reagent cover 72 can slide in a horizontal direction, as shown by the arrow "A". The first sliding reagent cover 70 has a plurality of openings 74 formed therein, which can be placed in register with a plurality of reagent containers 30. Similarly, the second sliding reagent cover 72 has a plurality of openings 76 formed therein, which can be placed in register with a plurality of reagent containers 30. As shown in FIGS. 8A, 8B, 8C, and 8D, the openings 74 and the openings 76 are rectangular in shape. At the left edge of each opening 76 in the second sliding reagent cover 72 is a semi-circular notch 78. This semi-circular notch 78 has its open portion facing the right. At the right edge of each opening 74 in the first sliding reagent cover 70 is a semi-circular notch 80. This semi-circular notch 80 has its open portion facing the left. The first sliding reagent cover 70 and the second sliding reagent cover 72 can be moved relative to one another so that the notches 80 in the first sliding reagent cover 70 and the notches 78 in the second sliding reagent cover 72 join to form a small opening, through which the tip of a pipette can be inserted to aspirate a liquid reagent from a reagent container 30. When the reagent is not being aspirated, the first sliding reagent cover 70 and the second sliding reagent cover 72 can be moved relative to one another so that the small opening is closed, thereby enabling the first sliding reagent cover 70 and the second sliding reagent cover 72 to reduce the effect of the environment on the reagents, thereby resulting in a longer useful life for the reagent.

The individual reagent containers 30 for clinical chemistry assays and the individual reagent containers 30 for immunoassays can be removed from reagent container carriers 34, inserted at the appropriate locations of sub-section 62 of the analysis section 60 by means of a robotic system, wherein gripping devices 92 can be affixed to a device 94 that can aspirate and dispense liquids, hereinafter alternatively referred to as an aspirating/dispensing device 94. See FIGS. 9A, 9B, 9C, 9D, 9E, and 9F for schematic diagrams illustrating gripping devices suitable for use herein. The aspirating/dispensing device 94 is capable of aspirating liquids from a container and dispensing liquids into a micro-well of a micro-well plate. The aspirating/dispensing device 94 has a head 96 that can be equipped with a plurality of pipettes 98. A commercially available robotic system suitable for use herein typically has from four to twelve pipettes. The gripping devices 92 are capable of gripping reagent containers 30, sample containers 18, and micro-well plates, raising the gripped container or the gripped micro-well plate in a vertical direction, and lowering the gripped container or the gripped micro-well plate in a vertical direction. The aspirating/dispensing device 94 is capable of moving in the two horizontal directions that are perpendicular to one another. The range of movement in either direction is unlimited. However, for the sake of economics, it is preferred that the analysis sections be as small as possible. Accordingly, it is expected that a typical range of movement for the aspirating/dispensing device 94 be from about two feet to about eight feet, preferably from about two feet to about six feet, more preferably from about two feet to about four feet in both horizontal directions. A robotic system suitable for use with the apparatus and method described herein is commercially available from Hamilton Company. In this system, two pipettes 98 of the aspirating/dispensing device 94 are capable of receiving the gripping devices 92. The gripping devices 92 can be securely attached to the stems of the pipettes 98 of the aspirating/dispensing device 94 by means of an expandable O-ring locking mechanism. The expandable O-ring locking mechanism is described in U.S. Pat. No. 7,033,543, incorporated herein by reference.

Figure 9A:
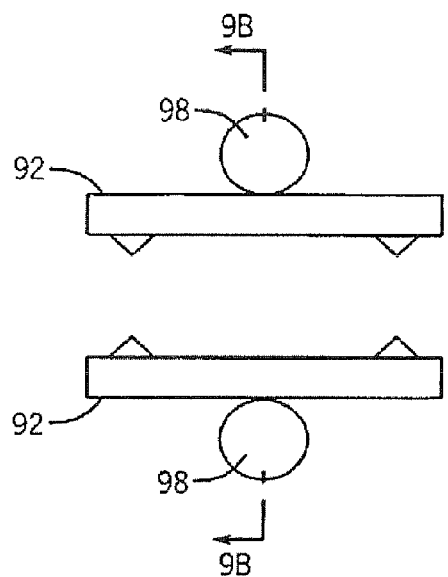
FIG. 9A is a schematic diagram illustrating the top view of gripping devices attached to an aspirating/dispensing device, the gripping devices gripping a micro-well plate.
Figure 9B:
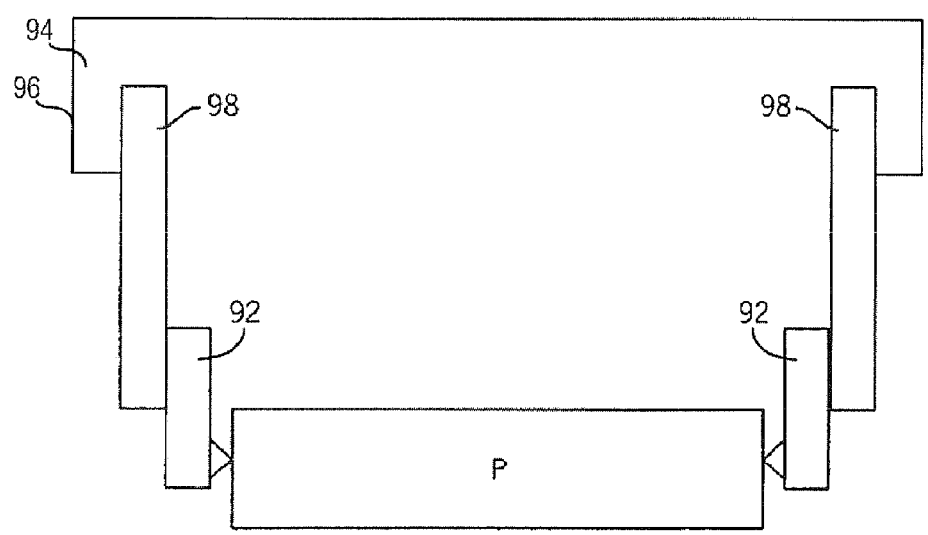
FIG. 9B is a schematic diagram illustrating a cross-sectional view of FIG. 9A taken along line 9B-9B.

The gripping devices 92 are typically rectangular parallelepipeds, e.g., in the shape of paddles, and are typically made of metal, e.g., stainless steel. FIGS. 9A and 9B illustrate gripping devices 92 that are suitable for gripping micro-well plates. Each paddle-shaped gripping device 92 has at least one projection, preferably two or more projections, on the major surface thereof that contacts the edge of a micro-well plate. When the paddle-shaped gripping devices 92 are affixed to pipettes 98, the paddle-shaped gripping devices 92 are retained by the expandable O-rings previously mentioned. This same expandable O-ring can be used to retain a pipette tip, which can be slipped over the discharging end of a pipette 98. This expandable O-ring mechanism holds the pipette tip securely, while the pipette is being used to aspirate and dispense fluids and even when the pipette tip is penetrating the septum of a container, which activity would typically cause a friction-staked pipette tip to be pulled off the discharging end of the pipette.

Figure 9C:
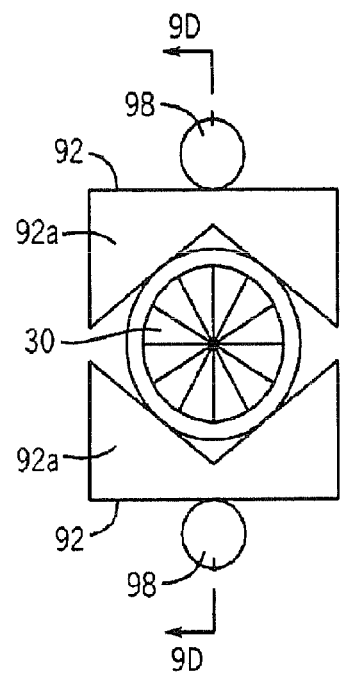
FIG. 9C is a schematic diagram illustrating the top view of gripping devices attached to an aspirating/dispensing device, the gripping devices gripping a cylindrical container.
Figure 9D:
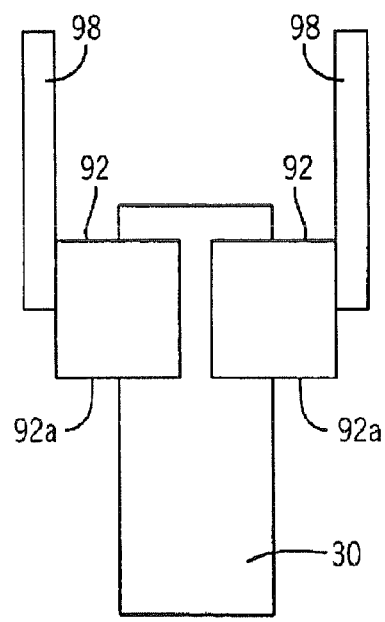
FIG. 9D is a schematic diagram illustrating a cross-sectional view of FIG. 9C taken along line 9D-9D.
Figure 9E:
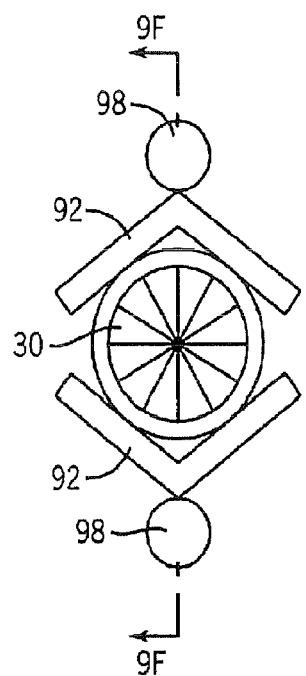
FIG. 9E is a schematic diagram illustrating the top view of gripping devices attached to an aspirating/dispensing device, the gripping devices gripping a cylindrical container.
Figure 9F:
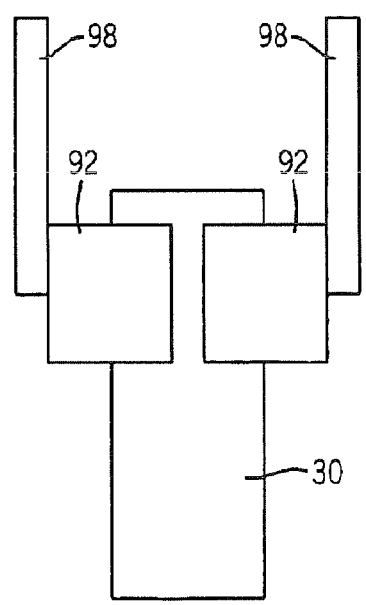
FIG. 9F is a schematic diagram illustrating a cross-sectional view of FIG. 9E taken along line 9F-9F.

In order for the aspirating/dispensing device 94 to grip a micro-well plate, two pipettes of the aspirating/dispensing device 94 to which the gripping devices 92 are attached are moved toward each other, whereby the micro-well plate can be gripped between the paddle-shaped gripping devices 92. When being gripped, the micro-well plate can be either in the portrait or landscape orientation, i.e., the micro-well plate can be gripped via either the two longer sides of the micro-well plate or by the two shorter sides of the micro-well plate. The projections mentioned previously penetrate slightly into the surface of the soft plastic material of the micro-well plate, thereby securely holding the micro-well plate for raising, lowering, or transporting. Various modifications of the gripping devices 92 can be used for gripping cylindrical-shaped containers, such as, for example, reagent containers 30, sample containers 18. For the purpose of gripping cylindrical-shaped containers, the gripping devices 92 are preferably rectangular parallelepipeds, as shown and described previously, to which are attached adapters 92a of such a size and shape that the adapters 92a can substantially conform to the shape of the container. FIGS. 9C and 9D illustrate gripping devices 92 that are suitable for gripping cylindrical-shaped containers. Another embodiment of a gripping device 92 that carries out the same function as the gripping device 92 illustrated in FIGS. 9C and 9D is the gripping device 92 illustrated in FIGS. 9E and 9F. In the gripping device 92 illustrated in FIGS. 9E and 9F, the paddles, instead of being straight, are substantially L-shaped. A pipette 98 equipped with the L-shaped gripping device 92 can readily grip, lift, transfer, lower, and place cylindrical containers 30 from any location to any other location in the analysis section 60 of the laboratory automation system 10.

Figure 10C:
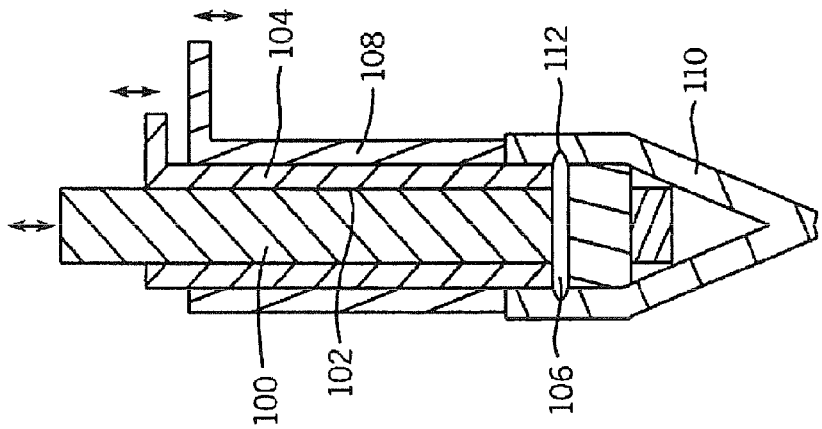
FIGS. 10A, 10B, 10C, 10D, and 10E are schematic diagrams illustrating the steps required to insert a gripping device or a pipette tip onto the end of a pipette and to remove the gripping device or the pipette tip from the end of the pipette.
Figure 10B:
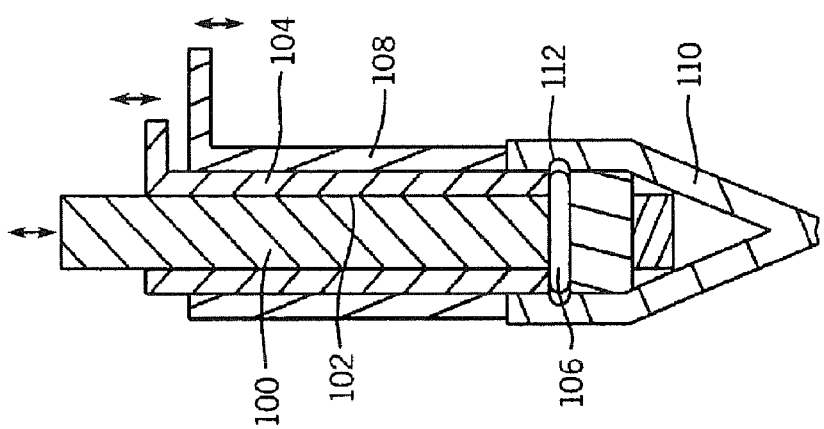
Figure 10A:
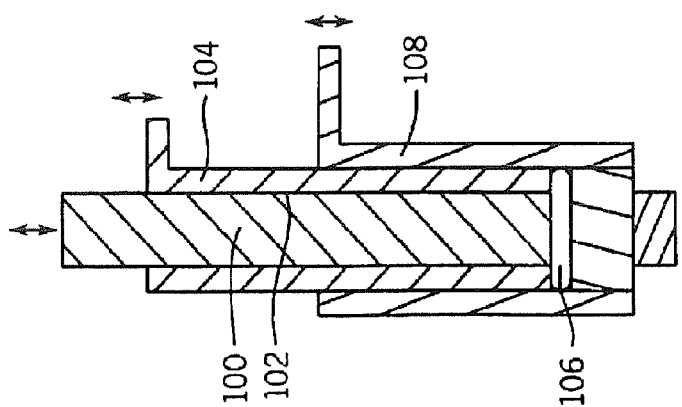
Figure 10E:
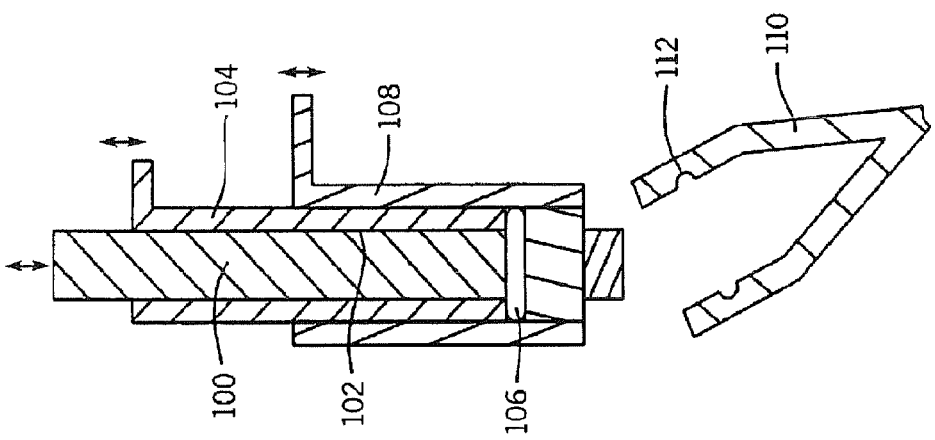
Figure 10D:
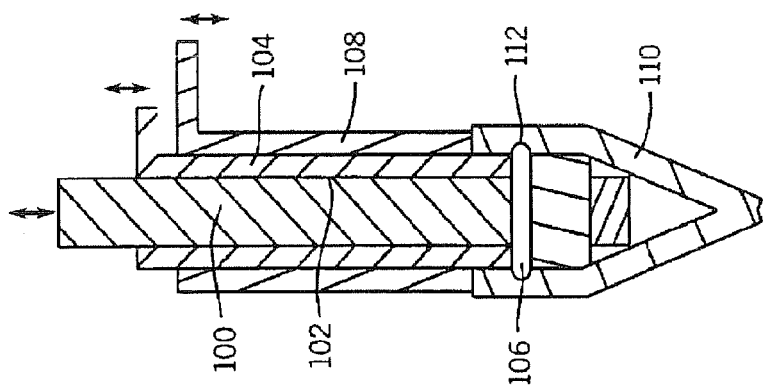

FIGS. 10A, 10B, 10C, 10D, and 10E illustrate the operation of the expandable O-ring locking mechanism. The pipette 98 comprises a cylindrical tube having an interior wall 100 and an exterior wall 102. Encircling a significant portion of the exterior wall 102 of the pipette 98 is an O-ring actuator sleeve 104. An expandable O-ring 106 is positioned around the exterior wall 102 of the pipette 98 and immediately below the lower end of the O-ring actuator sleeve 104. The expandable O-ring 106 is typically made from a resilient polymeric material. Encircling a significant portion of the O-ring actuator sleeve 104 is an ejector sleeve 108. In FIG. 10A, neither a gripping device 92 nor a pipette tip 110 is mounted to the pipette 98. In FIG. 10B, either a gripping device 92 or a pipette tip 110 is mounted to the pipette 98 by means of a slip fit, wherein there is little or no insertion force. In FIG. 10C, the expandable O-ring 106 is compressed and expanded by means of the O-ring actuator sleeve 104, which is moved vertically by a small motor (not shown). In FIG. 10D, the gripping device 92 or the pipette tip 110 is locked onto the cylindrical tube of the pipette 98 via the expandable O-ring 106 and a groove 112 in the interior wall of the pipette tip 110. In FIG. 10E, the expandable O-ring 106 is decompressed and retracted radially by raising the O-ring actuator sleeve 104, by reversing the direction of the aforementioned motor. The gripping device 92 or the pipette tip 110 is removed for disposal or reuse by means of the ejector sleeve 108, which is moved relative to the main tube of the pipette by a small motor (not shown).

Alternative embodiments of robotic mechanisms (not shown) for gripping micro-well plates can also be employed. In one alternative embodiment, the robotic mechanism can grip a micro-well plate, raise and lower the micro-well plate vertically, and rotate the micro-well plate while it is being transported. This type of robotic mechanism, while useful for such operations as rotating micro-well plates to facilitate insertion of the plates into various types of assay processors and readers of results of assays, moves micro-well plates above the deck of the laboratory automation system 10 only. It should be noted that in FIGS. 1, 5, 6, and 7, the components shown therein are positioned on only a single level. Another alternative embodiment of robotic mechanism, in addition to exhibiting all of the features of the previously mentioned embodiments, is further capable of transporting micro-well plates from a position above the deck of the laboratory automation system 10 to a position below the deck of the laboratory automation system 10, thereby providing another option for transporting micro-well plates from the pipette, then to an assay processor, then to a reader, and finally to a container for waste. This embodiment provides an alternative to three-dimensional transport in a limited vertical space. This embodiment will be described in greater detail following the discussion of FIG. 23.

The use of a pipette, such as a Hamilton pipette, eliminates pumps and lines by using dry air displacement syringes. Such a pipette provides asymmetric pipette spread for more efficient dispensing of liquids. An asymmetric pipette spread means that the dispensing of liquids can be carried out from variable locations, i.e., the pipettes need not be spaced equidistant from one another. In addition, such a pipette provides capacitative and pressure liquid level sense along with pressure monitoring during aspirating and dispensing. As mentioned previously, the use of expandable O-rings also eliminates the necessity of mounting pipette tips by means of frictional force, which frictional force typically results in the deformation of the pipette tips.

The reagent containers 30 are preferably contained in a refrigerated area, e.g., an area where the temperature can range from about 2° C. to about 8° C. As discussed previously, the reagent containers 30, as well as the sample containers 18 or adapter sleeves 28 for sample containers 18, can be equipped with radio frequency identification tags, which can be read by an automated radio frequency identification reader (not shown) positioned below the sub-section 62 of the analysis section 60. A radio frequency identification reader can read and update radio frequency identification tags on reagent containers 30 and on sample containers 18 (or on sample container carriers 24) when aspiration of a portion of the reagent or a portion of the sample is carried out or an operation for scanning the items in inventory is initiated. Information of the type shown in TABLE 1 can be updated on the radio frequency identification tags by the radio frequency identification reader.

TABLE 1

| Class of data | Specific data |
| --- | --- |
| Tag identifier | Unique identifier for container |
| Manufacturing data | (a) Revision number(s) of reagent(s) |
|  | (b) Serial number(s) of reagent(s) |
|  | (d) Component identifier(s) |
|  | (e) Lot number(s) of reagent(s) |
|  | (f) Stability/expiration data for reagent(s) |
|  | (g) Times/dates of manufacture of reagent(s) |
|  | (h) Configuration(s) of assay(s) |
|  | (e.g., number of reagent containers needed) |
|  | (i) Number of tests in container(s) |
|  | (j) Associated components of assay(s) |
|  | (k) Calibration data for assay(s) |
| Shipping and storage data | (a) Temperature(s) of reagent during shipping |
|  | (b) Times/dates of shipping movements and storage periods |
|  | (c) Locations and dates of storage periods |
| Analyzer and usage data | (a) Times/dates of opening(s) of reagent container(s) |
|  | (b) Number of aspirations from reagent container(s) |
|  | (c) Carryover and potential contamination or dilution of reagent(s) or sample(s) |
|  | (d) Encryption algorithms for protection of data |
|  | (e) Other algorithms to ensure integrity of data |
|  | (f) Chain of custody for operations performed on micro-well plates, reagent containers and sample containers; for micro-well plates, dispensing of samples, reagents(s), incubation temperature, processing, and readings; for reagent containers, date of manufacture, date of shipping, date of loading in reagent inventory management system, date of opening, date of loading into analyzer, aliquots removed and remaining, cumulative carryover, expiration date; for sample containers, draw date, patient, doctor, technicians, test orders, centrifugation, decapping, aliquots removed, cumulative carryover, resealing, entry into storage |

An area located in front of the analysis section 60, can be used as a radio frequency identification read zone for micro-well plates. A system for utilizing radio frequency identification tags and radio frequency identification readers is described in U.S. application Ser. No. 11/495,430, filed Jul. 28, 2006, which has previously been incorporated herein by reference.

For reagents for use in immunoassays, the sub-section 62 of the analysis section 60 can typically accommodate thirty-four (34) reagent containers 30 for dispersible magnetic microparticles, thirty-four (34) reagent containers 30 for conjugate, i.e., the component that contains the label for the assay, e.g., a chemiluminescent conjugate, and thirty-four (34) reagent containers 30 for diluent. The reagent containers for the dispersible magnetic particles, the reagent containers for the conjugate, and the reagent containers for the diluent can be the same or they can differ from one another, so long as they are compatible with the analysis section 60 of the laboratory automation system 10. Each reagent container 30 that contains dispersible magnetic microparticles is placed on a seat (not shown) that is equipped with a shaft (not shown) journaled in a bearing (not shown), thereby allowing rotation of the seat by means of rotation of the shaft in the bearing. The shaft is rotated by a small gear (not shown) positioned on the shaft beneath the bearing. The small gear of a given reagent container 30 engages the small gear of a reagent container 30 adjacent thereto. The gear of the reagent container 30 positioned at an end of a row of reagent containers 30 is engaged by a drive gear 114 attached to a dispersing motor (not shown), e.g., a stepper motor. The drive gear 114 causes the small gear of the reagent container 30 positioned at the end of the row of reagent containers 30 to rotate, which in turn causes the small gear of the next adjacent reagent container 30 thereto to rotate, which further in turn causes the small gear of the next adjacent reagent container 30 thereto to rotate, and so forth, thereby causing all of the small gears of the reagent containers in the row to rotate, with the result that all of the reagent containers 30 are caused to rotate. Such rotation of all of the reagent containers 30 brings about the dispersing of the magnetic microparticles in all of the reagent containers 30 containing magnetic microparticles in the row at the end of which is the motor. The reagent containers 30 for immunoassays can be keyed to prevent incorrect loading of the containers. Such keying can be effected by designing the reagent containers 30 in such a manner that the reagent containers 30 can be inserted in only a single orientation. Such keying is not generally used for automated loading of reagent containers 30. However, keying is desirable for preventing an inferior container of a competitor to be used with the apparatus described herein.

Another type of keying feature involves adapter plates or guides (not shown) on the printed circuit board of the radio frequency identification system to prevent racks for reagent containers for immunoassays from being placed in racks for reagents for clinical chemistry assays. In addition, racks for reagent containers for immunoassays cannot be loaded backwards if blind mate connectors are employed, because, if these racks are loaded backwards, these racks will not properly conform to the blind mate connectors, whereby the dispersing motor will not be connected, and an error will be signaled. The racks for reagent containers for clinical chemistry assays can be installed in any direction, and will work properly, because printed circuit board of the radio frequency identification system identifies each container individually.

The reagent containers 30 containing dispersible microparticles are rotated continuously (except during an aspirating step) in the same manner as employed by the ARCHITECT®instrument, i.e., 360° in one direction and then 225° in the opposite direction. See, for example, U.S. Pat. Nos. 5,580,524; 6,436,349; and 6,498,037, all of which are incorporated herein by reference. For containers for use in clinical chemistry assays, the sub-section 62 of the analysis section 60 can typically accommodate sixty-eight (68) reagent containers 30 for various reagents. The number of reagent containers 30 that can be accommodated by the sub-section 62 of the analysis section 60 is not critical. The numbers set forth previously are merely representative examples for a typical arrangement.

Bulk liquids, such as, for example, a pre-trigger solution for certain types of immunoassays, wash buffer, and deionized water, are preferably contained in troughs 116a, 116b, 116c, etc., so that a plurality of pipette tips 110 can aspirate a specific liquid simultaneously. The purpose of the pre-trigger solution is to enable the release of a chemiluminescent material, e.g., acridinium, from the conjugate that has bound to the magnetic microparticles in an immunoassay. In addition, the pre-trigger solution adds hydrogen peroxide and lowers the pH to a level so that no photons are emitted from the chemiluminescent material. A trigger solution complementary to the pre-trigger solution raises the pH back to neutral by means of a basic solution, e.g., sodium hydroxide solution, and allows the hydrogen peroxide to generate photons from the chemiluminescent material. Dispensing of bulk liquids can also be performed by a sub-system on the analysis section 60 in order to reduce the burden of the aspirating/dispensing device 94. As shown in FIGS. 1, 5, and 6, the sub-section 62 of the analysis section 60 can accommodate six (6) troughs. The number of troughs that can be accommodated by the sub-section 62 of the analysis section 60 is not critical. The numbers set forth previously are merely representative examples for a typical arrangement. Other bulk liquids can be stored where appropriate. For example, the trigger solution for certain types of immunoassays, which is used in conjunction with the pre-trigger solution, can be stored in a reader, such as, for example, a luminescence reader, whereby the trigger solution is released at the point when the results of the assay are to be read. The trigger solution enables photons to be emitted from the label of the reaction product of the immunoassay within from about 3 to about 5 seconds.

A storage area 120 for pipette tips (both unused pipette tips and pipette tips for reuse) and a temperature controllable micro-well plate rotator 122 or stationary aspirating/dispensing locations 124 are positioned at the sub-section 64 of the analysis section 60. If stationary aspirating/dispensing devices are used, a plate rotator need not be used.

Racks 126 for disposable pipette tips and containers 128 for solid waste can be located at or near the center of the analysis section 60, thereby minimizing travel distances of the aspirating/dispensing device 94 over the clean laboratory equipment, e.g., pipette tips, micro-well plates, for aspirating/dispensing operations. These racks 126 for disposable pipette tips are used to store disposable pipette tips for immunoassays and clinical chemistry assays prior to the use thereof. Racks 130 for tip combs, i.e., a disposable item used in inverse magnetic particle processing, are used to store tip combs prior to the use thereof. Used tip combs can be disposed of in a rack 132 for used tip combs. "Re-use" racks 134 for pipette tips can be used to store pipette tips allocated to specific reagent containers 30 or bulk liquids in order to reduce the consumption of pipette tips. A rack stacker 136 for disposable tips is capable of storing a large number of racks of disposable tips in a dispenser that dispenses racks of disposable tips. The rack stacker 136 can be an elongated container wherein a spring or motor drive urges the stored racks toward the surface of the analysis section 60. Other "re-use" racks (not shown) for pipette tips can be used to store pipette tips allocated to specific samples when those samples are tested in the immunoassay mode and the clinical chemistry assay mode in order to reduce the consumption of pipette tips. A pipette tip can be reused if the pipette tip repeats the use of the same sample or the same reagent, i.e., so long as there is no carryover from another sample or another reagent. After all of the tests for a given sample are complete, the pipette tip for the sample is ejected to solid waste in a container 128 for solid waste located in an appropriate position near the analysis section 60. The aforementioned racks can be designed to be compatible with the expected contents thereof. Such racks are commercially available and are well-known to those of ordinary skill in the art.

Representative examples of capacities of various storage areas for disposable items are as follows:
(a) Rack for disposable tips can hold up to 96 disposable tips 1-1000 µL;
(b) Rack for reusable disposable tips can hold up to 96 disposable tips 1-1000 µL;
(c) Rack for disposable tips can hold up to 96 disposable tips 1-300 µL;
(d) Rack for reusable disposable tips can hold up to 96 disposable tips 1-300 µL;
(e) Stacker for racks for disposable tips (4), 96 disposable tips 1-300 µL;
(f) Rack for reusable disposable tips can hold up to 96 disposable tips 1-1000 µL;
(g) Clean tip comb rack;
(h) Used tip comb rack A pre-treatment and dilution area is located at the stationary aspirating/dispensing location 124. At this location, if desired, the micro-well plate can be maintained in a stationary position, i.e., incapable of rotation. Pre-treatment steps and/or dilution steps are performed prior to immunoassay processing and clinical chemistry assay processing.

Referring now to FIGS. 1, 5, and 6, an immunoassay processor 140 is positioned at the sub-section 66 of the analysis section 60. In FIG. 7, a different type of immunoassay processor is used. This immunoassay processor is designated by the reference numeral 140a. More than one immunoassay processor 140 can be utilized. A clinical chemistry assay processor 142 is positioned at the sub-section 68 of the analysis section 60. More than one clinical chemistry assay processor can be utilized. Storage racks 144 for micro-well plates are positioned at or near the sub-section 68 of the analysis section 60. Stackers 146 for micro-well plates are used to store micro-well plates for immunoassays and clinical chemistry assays prior to kitting the micro-well plates for immunoassays or clinical chemistry assays. As indicated previously, the laboratory automation system described herein can function with a clinical chemistry assay processor(s) without any immunoassay processor or can function with an immunoassay processor(s) without any clinical chemistry processor.

The immunoassay processor 140 provides the following functions: incubation of reaction mixtures, mixing of reaction mixtures, separation of components from reaction mixtures, washing of reaction product(s), and release of label to enable reading of the results of immunoassays. An immunoassay processor 140 that can be modified for use herein is a KingFisher™ magnetic particle processor, commercially available from Thermo Fisher Scientific, Inc., Waltham, Mass., and described in U.S. application Ser. No. 11/923,828, filed Oct. 25, 2007, and entitled METHOD OF PERFORMING ULTRA-SENSITIVE IMMUNOASSAYS, incorporated herein by reference. Other magnetic particle processors that can be modified for use in certain embodiments described herein include KingFisher™ 96 magnetic particle processor, commercially available from Thermo Fisher Scientific, Inc., Waltham, Mass. This type of immunoassay processor is depicted in FIG. 7, and designated by the reference numeral 140a. The KingFisher™ Flex magnetic particle processor can provide rapid and reproducible purification of high-quality DNA, RNA, proteins, and cells from various starting materials, such as, for example, blood, cell cultures, tissue lysates, soil, and faeces. Like the KingFisher™ magnetic particle processors described previously, the KingFisher™ Flex magnetic particle processor uses magnetic rods that move particle through the various purification phases, i.e., binding, missing, washing, elution. The KingFisher™ Flex magnetic particle processor uses a 24-rod magnet head and 24-well deep well plate. The volume of sample can be as high as 5 mL. For higher throughput needs, 96 samples can be processed in different working volumes (20-1000 µL) using 96-rod magnet head and appropriate 96-well plates. Details relating to the KingFisher™ Flex magnetic particle processor are accessible by means of the Hypertext Transfer Protocol on the World Wide Web at the website thermo.com/com/cda/product/detail/1,10136240,00.html, incorporated herein by reference. The KingFisher™ Flex magnetic particle processor can be incorporated into a modified embodiment of the type illustrated in FIG. 7.

In the embodiment wherein the label is a chemiluminescent label, the release of label is carried out in a manner similar to that used in the ARCHITECT® analyzer, as described in U.S. Pat. Nos. 5,795,784 and 5,856,194, both of which are incorporated herein by reference. The trigger solution is dispensed during the reading of a reaction product in a well.

A luminescence reader 150 separate from the immunoassay processor 140 is positioned at the sub-section 68 of the analysis section 60 to read the results of the immunoassay from the micro-well plates after the reaction mixtures are processed. The micro-well plates can be moved from the immunoassay processor 140 to the luminescence reader 150 by means of a conveyor belt 151. Alternatively, the micro-well plates can be moved from the immunoassay processor 140 to the luminescence reader 150 by means of a robotic mechanism, such as, for example, a robotic mechanism of the type illustrated in FIG. 23 and described in connection with an embodiment of a multiple-level analysis section.

A one channel, 96-position luminescence reader 150 can be housed in an enclosure in which light and temperature can be controlled. The addition of the trigger solution and the readings are carried out in the micro-well plate by means of a stationary dispenser/reader and a moving micro-well plate. The micro-well plate moves inside of the luminescence reader 150, whereby the light-collecting aspect of reading takes place in one column at a time. The trigger solution is dispensed during the reading of a reaction product in a micro-well. For the micro-well plate utilized herein, the collection lens of the luminescence reader 150 is positioned over the micro-well of interest, and the photons are counted as the trigger solution is being injected. The micro-wells of the micro-well plates are reflective of light so that more of the light generated by the chemiluminescent reaction can be detected. The micro-wells typically bear a pigment, usually white. The trigger solution is direct vertically aligned with the micro-wells and injected by means of a positive displacement pump. A luminescence reader 150 suitable for use with apparatus described herein is commercially available from Molecular Devices Corporation under the trademark LMax II 384. This reader 150 has a sensitivity of 0.6 attomole (T3 tracer acridinium). This reader 150 can operate at wavelengths ranging from about 380 nm to about 630 nm. This reader 150 has a dynamic range of greater than 5 decades, i.e., 1 to 100,000. This reader 150 can provide incubation of micro-well plates. This reader 150 can further provide accommodate a micro-well plate having 384 micro-wells, thereby enabling the reduction of volume of the reagent.

Figure 23:
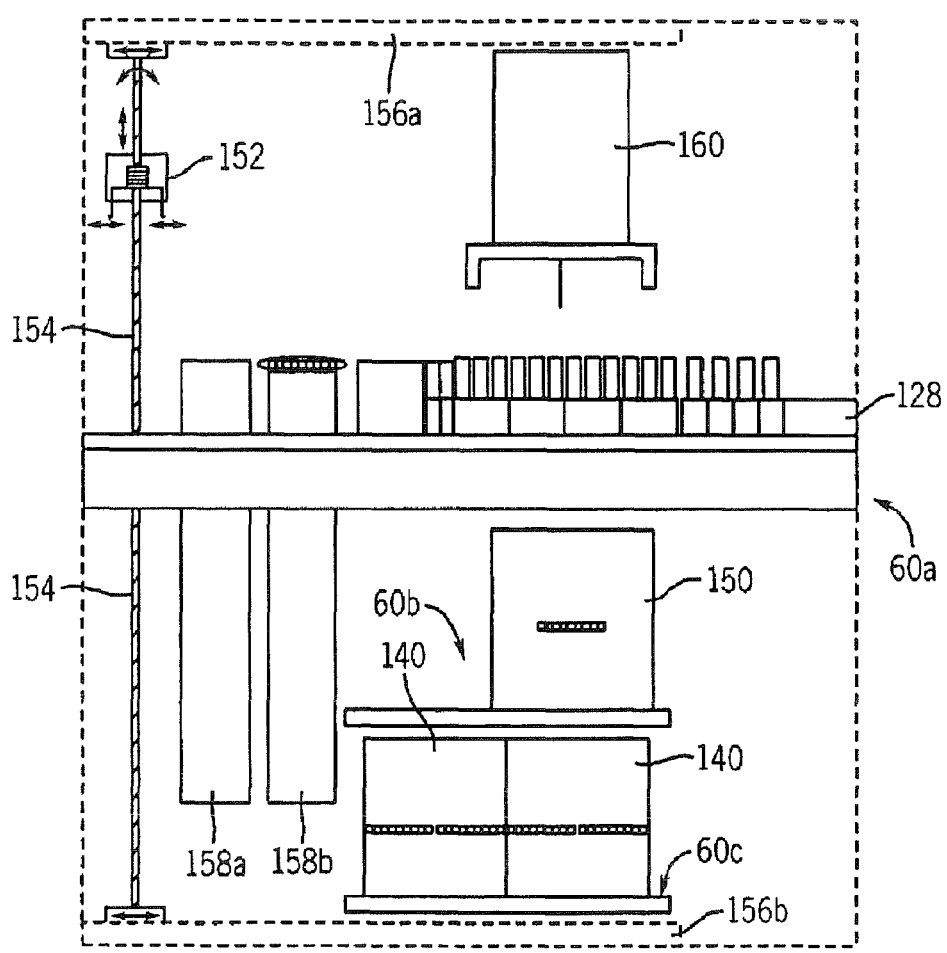
FIG. 23 is schematic diagram illustrating an analysis section of a laboratory automation system that has a multiple level configuration.

Referring now to FIG. 23, it can be seen the single level analysis section 60 is divided into three levels, whereby the quantity of floor area required for the components of the analysis section 60 of the laboratory automation system 10 can be reduced. The sample containers 18 and reagent containers 30 are positioned on the upper level 60a. The luminescence reader(s) 150 is (are) positioned on the middle level 60b and the immunoassay processor(s) 140 is (are) positioned on the lower level 60c. A robotic gripping device 152 is capable of moving vertically by means of a threaded screw 154. Attached to the robotic gripping device 152 is a nut (not shown) that enables the robotic gripping device 152 to move vertically along the threaded screw 154. Movement of the nut can be actuated by a motor (not shown), typically a stepper motor. The robotic gripping device 152 is further capable of moving in a horizontal direction along tracks 156a, 156b, which are dedicated to the robotic gripping device 152. The robotic gripping device 152 can be designed to have features to enable telescoping movement and rotational movement. The telescoping feature enables the robotic gripping device 152 to have the reach thereof extended or retracted. The rotational feature facilitates the gripping, raising, lowering, and placing of micro-well plates in positions desired. It should be noted that the analysis section can employ more than two levels 60a, 60b. Also shown in FIG. 23 are stacker drawers 158a and 158b for storing and dispensing disposable tips and micro-well plates, respectively. The aspirating/dispensing device 160 need not have the capability of functioning as a gripping device for reagent containers or micro-well plates or both containers and micro-well plates. However, this capability can enhance the automated features of the laboratory automation system 10.

Immunoassays can be carried out by means of an immunoassay processor 140 known as a magnetic particle processor. A representative example of a magnetic particle processor that can be modified for use with the laboratory automation system described herein is the KingFisher™ magnetic particle processor, commercially available from Thermo Fisher Scientific, Inc., Waltham, Mass., and described in U.S. application Ser. No. 11/923,828, filed Oct. 25, 2007, and entitled METHOD OF PERFORMING ULTRA-SENSITIVE IMMUNOASSAYS, incorporated herein by reference. Other magnetic particle processors that can be modified for use in certain embodiments described herein include KingFisher™ 96 magnetic particle processor, commercially available from Thermo Fisher Scientific, Inc., Waltham, Mass. and KingFisher™ Flex magnetic microparticle processor. In the KingFisher™ 96 magnetic particle processor, a plurality of micro-well plates is used. Each micro-well plate of the plurality of plates corresponds to a single row of micro-wells of the KingFisher™ magnetic particle processor. The KingFisher™ magnetic particle processor 140 is designed for the automated transfer and processing of magnetic particles at volumes on the order of up to 300 microliters for clinical chemistry assays and up to 200 microliters. The principle of the KingFisher™ magnetic particle processor is based on the use of magnetic rods 162 covered with disposable, specially designed tip combs 164 and micro-wells (as reaction vessels). The KingFisher™ magnetic particle processor 140 functions without any aspirating or dispensing components or aspirating/dispensing devices.

Samples and reagents including magnetic particles are dispensed into the micro-wells in a micro-well plate. The use of a micro-well plate format allows the use of volumes on the order of up to 300 microliters for clinical chemistry assays and up to 200 microliters for chemiluminescent microparticle immunoassays. The steps of the protocol can be preloaded in embedded software, which can be selected by the user by means of the graphical user interface, which will be described later.

In one embodiment, the magnetic particle processor 140 can process one, or possibly two, micro-well plates in order to process twelve (12) to twenty-four (24) immunoassay tests substantially simultaneously. The temperature of the magnetic particle processor 140 can be controlled in the magnetic particle processing area. The target temperature of the liquid is 37° C.; the temperature of the temperature controlling circuit is set at a point slightly higher to account for heat loss.

In an alternative embodiment, the magnetic particle processor can utilize an entire 96 micro-well plate to constitute a single step of the process. In this embodiment, 96 immunoassay tests can be processed substantially simultaneously.

U.S. Pat. Nos. 6,448,092 and 6,596,162, both of which are incorporated herein by reference, describe the operation of a KingFisher™ magnetic particle processor 140 and a KingFisher™ magnetic particle processor 140a. In addition, U.S. patent application Ser. No. 12/257,428 entitled SYSTEM FOR AUTOMATICALLY LOADING LABORATORY ANALYZER, which has been filed as a non-provisional U.S. Patent Application on Oct. 24, 2008, and which claims priority from U.S. Provisional Application Ser. No. 60/985,794, filed Nov. 6, 2007, and furthermore, is incorporated herein by reference, illustrates useful modifications of the KingFisher™ magnetic particle processor.

Figure 11:
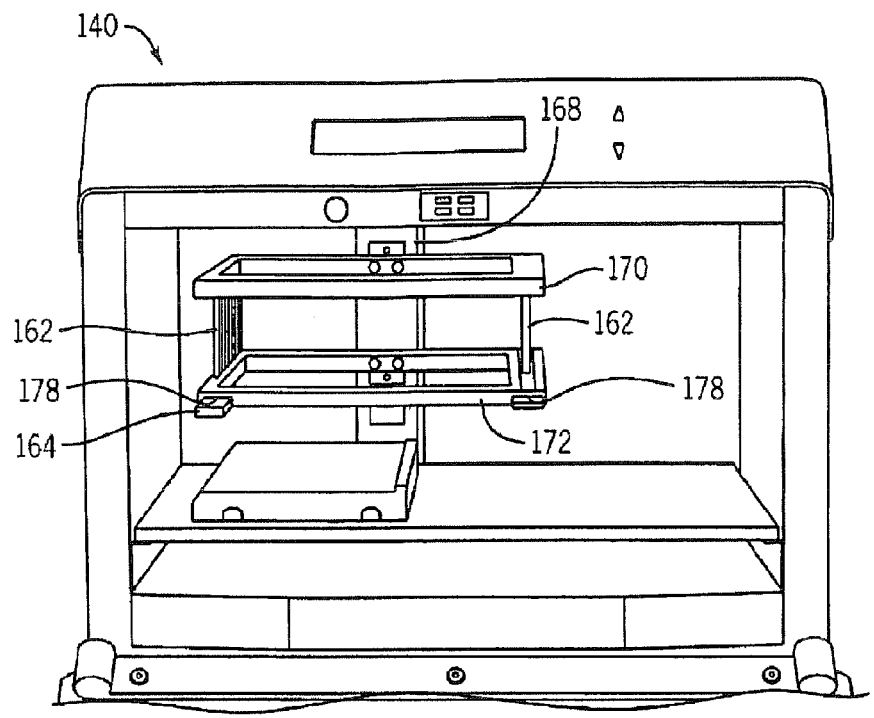
FIG. 11 is a front view in elevation of a commercially available magnetic particle processor.

Referring now to FIG. 11, The KingFisher™ magnetic particle processor 140 is designed for a maximum of two micro-well plates, each of which has 96 micro-wells, which micro-well plates are compatible with the tip combs 164. The micro-well plates are maintained stationary and the only moving assembly is a processing head 168 with tip combs 164 and magnetic rods 162. The processing head 168 consists of two vertically moving platforms 170, 172. One platform 170 is needed for the magnetic rods 162 (2.times.12 rods) and the other platform 172 is needed for the plastic tip combs 164. The platforms are rectangular metal frames that can be moved in both a horizontal direction, to move from one micro-well to another, and in a vertical direction to enter or exit a micro-well and to agitate magnetic particles in a micro-well. The platforms 170 and 172 are shown in FIG. 11.

Figure 12:
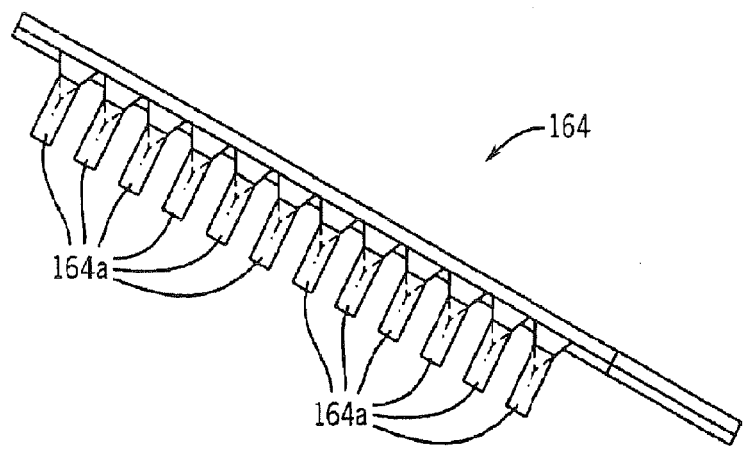
FIG. 12 is a front view in elevation of a tip comb suitable for use in the magnetic particle processor shown in FIG. 11.

One micro-well plate contains twelve columns and eight rows of micro-wells and processing of one sample typically uses up to eight micro-wells of a given column. In certain embodiments two micro-well plates can be employed, whereby more than eight micro-wells can be used to carry out an immunoassay. One tip comb 164 containing twelve tips 164a, as shown in FIG. 12, is used for processing twelve samples at a time within one micro-well plate, each sample requiring a separate column.

Before starting the magnetic particle processing via the aforementioned graphical user interface, the samples and the reagents are dispensed into the wells of the micro-well plate at the plate rotator 122. Kitting a micro-well plate for up to twelve immunoassays can be carried out at the plate rotator 122. The sample(s), the reagent(s), the buffer(s), and the other materials (e.g., the pre-trigger solution) are added at the plate rotator 122. The plate rotator 122 can be used to rotate the micro-well plate 900 to place the micro-well plate in the appropriate orientation for introducing the micro-well plate into the magnetic particle processor. The reactions mixtures can be incubated at the plate rotator 122. Incubation can be carried out by means of an overheating technique, whereby the micro-well plate is heated rapidly to a temperature of from about 42° C. to about 47° C., whereupon the source of heat is removed. By this means, the incubation step of the process can keep pace with the speed of the pipette. The rate of change of temperature is proportional to the difference of the temperature between the object being cooled or heated, and the agent performing the cooling or heating. It is desired to have the temperature of the liquid in a micro-well in a micro-well plate to be at temperature of 37° C. during the time required to kit the micro-well plate for an immunoassay or dispense a sample into a micro-well plate for carrying out clinical chemistry assays. Because this time interval is much shorter than the time interval required to reach equilibrium temperature on the plate rotator 122, the temperature of the plate rotator 122 is increased. In summary, the temperature of the plate rotator 122 will be set (via RS-232) so that the final temperature of the first liquids dispensed into the micro-wells of the micro-well plate reaches a temperature of 37° C. in the time required to dispense the remaining liquids. In other words, the liquids wherein temperature is critical are dispensed first.

A movable tray (not shown) capable of holding two separate micro-well plates can be moved into the magnetic particle processor 140 and out of the magnetic particle processor 140. The movement of the movable tray can be carried out manually, but is preferably be carried out by means of a motor-driven mechanism, such as, for example, a loader analogous to the type of loader used to load a compact disc into a compact disc player. An endless belt conveyor 151 can be used to transport micro-well plates from the magnetic particle processor 140 to the luminescence reader 150. The tip comb(s) 164 is (are) loaded into its (their) slots 178, which are located in the platform 172. The kitted micro-well plate(s) is (are) placed onto the movable tray in the correct position and the movable tray is pushed into the position required for magnetic particle processing of an immunoassay. During the magnetic particle processing operation, the front lid (not shown) and the top lid (not shown) of the magnetic particle processor 140 can be closed or can remain open. Closed lids protect the processing against environmental contamination and loss of heat.

Figure 13:
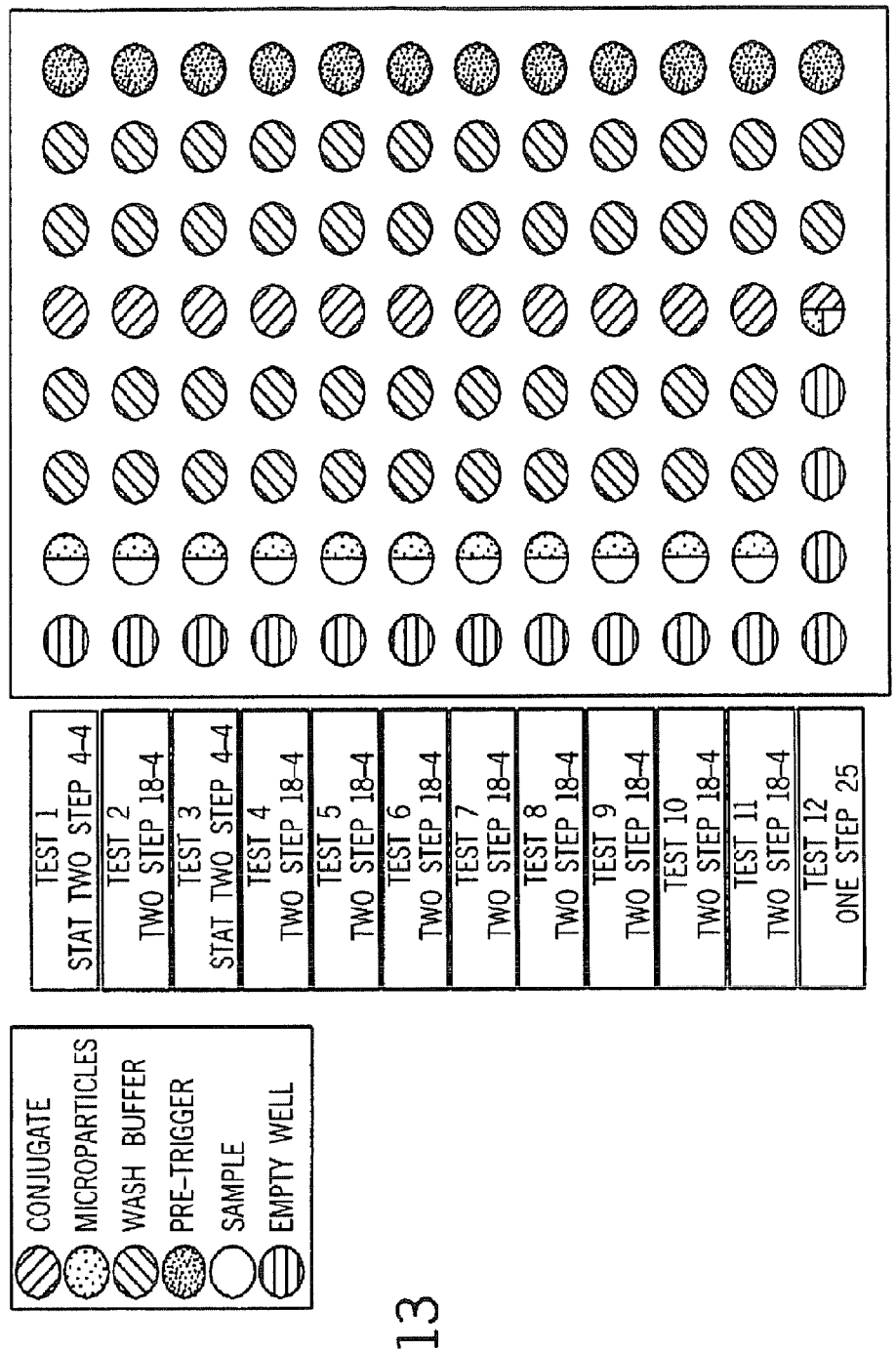
FIG. 13 is a top plan view of a micro-well plate illustrating the kitting of chemiluminescent microparticle immunoassays utilizing a single micro-well plate having 96 micro-wells.

FIG. 13 illustrates the kitting of chemiluminescent microparticle immunoassays utilizing a single micro-well plate having 96 micro-wells. Incubation of the sample and the magnetic microparticles are performed in the second row of the micro-well plate. Wash buffer is dispensed in the third, fourth, sixth, and seventh rows of the micro-well plate. The conjugate is dispensed in the fifth row of the micro-well plate. Pre-trigger solution is dispensed in the eighth row of the micro-well plate.

Figure 14:
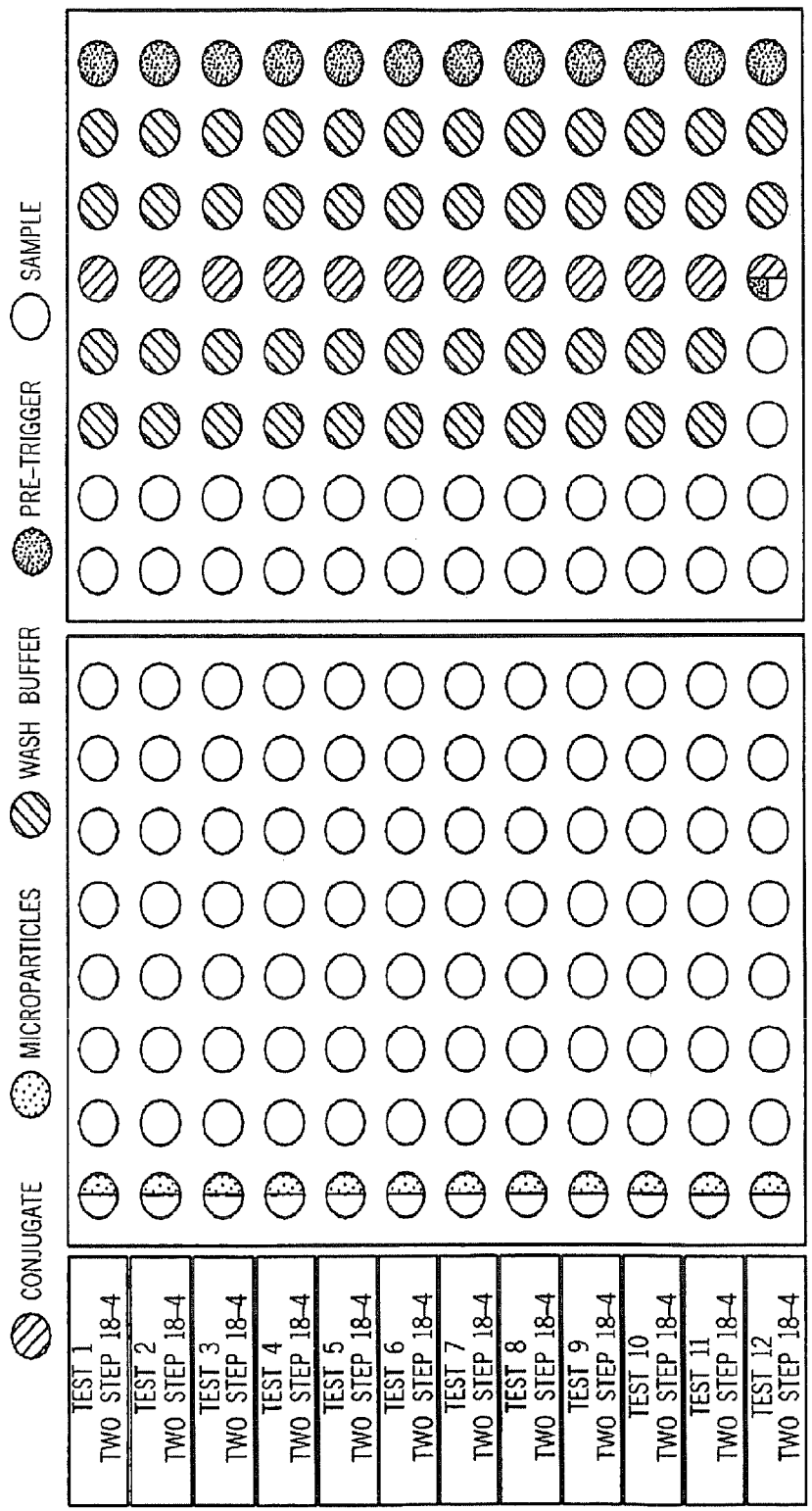
FIG. 14 is a top plan view of an arrangement illustrating the kitting of chemiluminescent microparticle immunoassays utilizing two micro-well plates, each micro-well plate having 96 micro-wells.
Figure 16A:
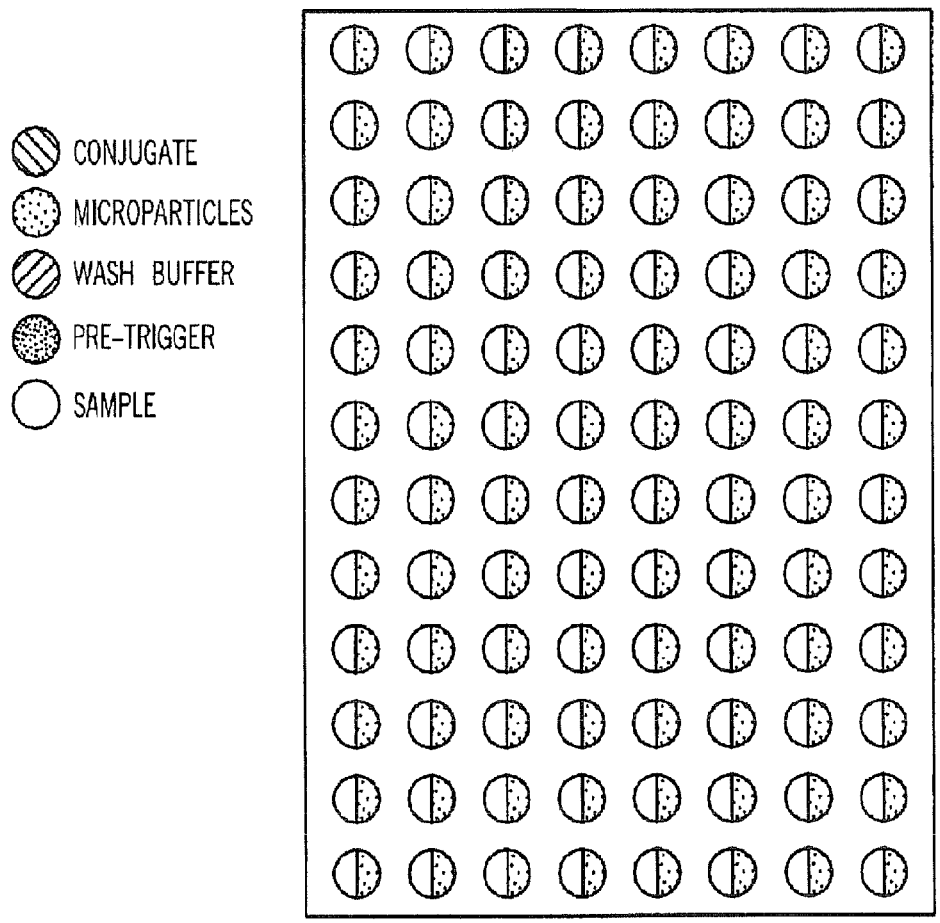
FIGS. 16A, 16B, 16C, 16D, 16E, 16F, and 16G are top plan views illustrating seven micro-well plates, each micro-well of a given micro-well plate containing the same ingredient. This kitting of micro-well plates enables 96 immunoassays to be conducted simultaneously.
Figure 16B:
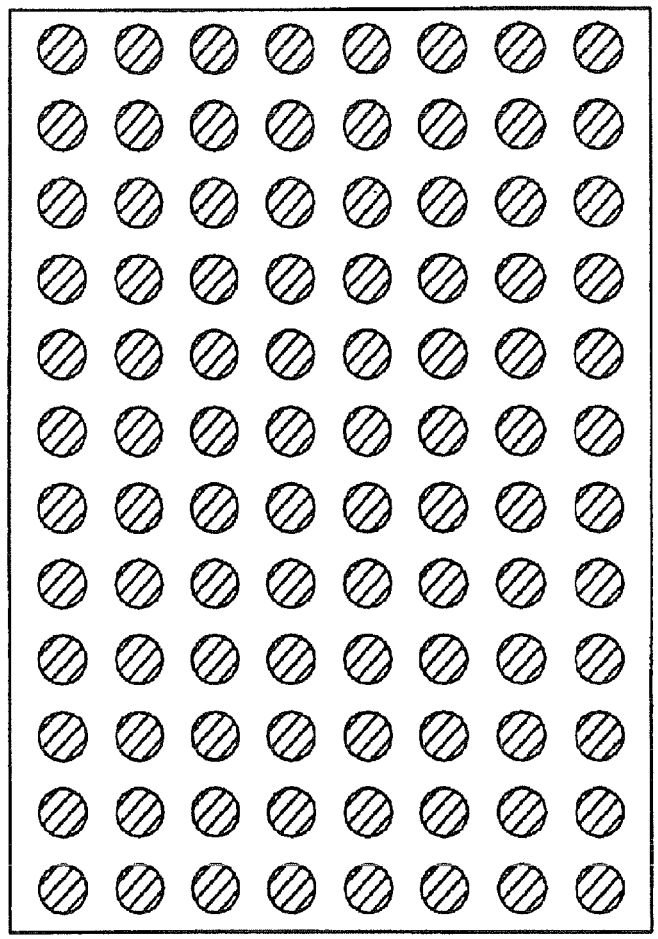
Figure 16C:
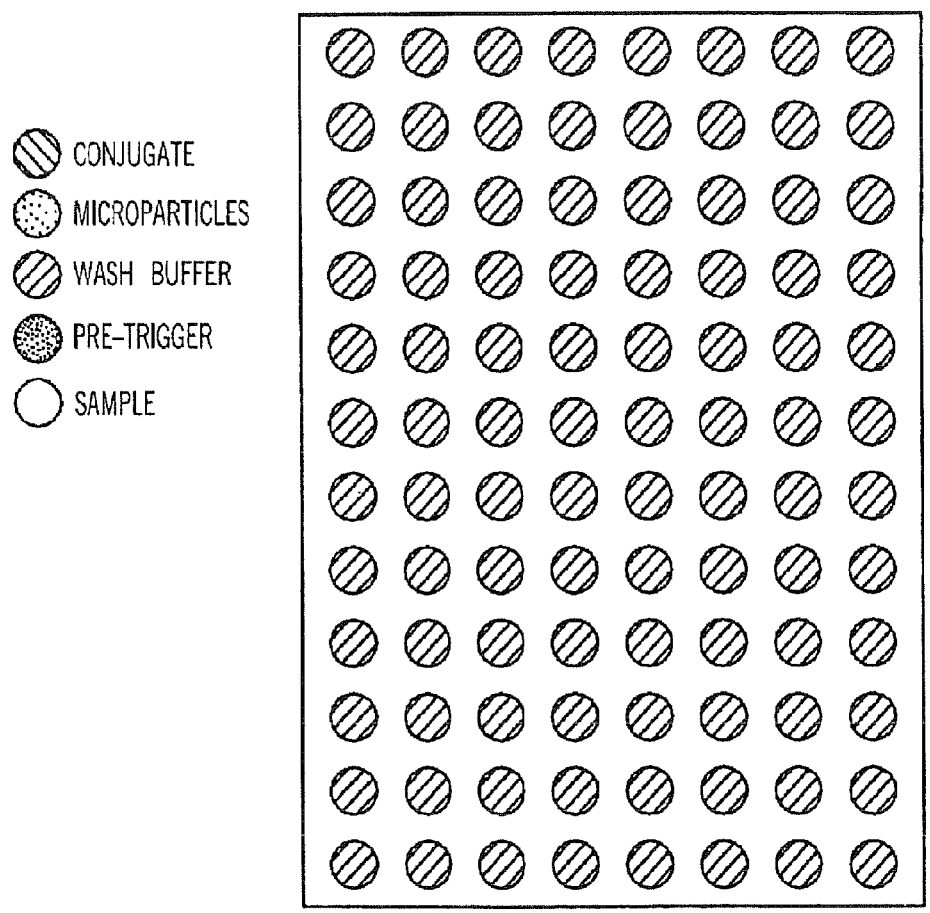
Figure 16D:
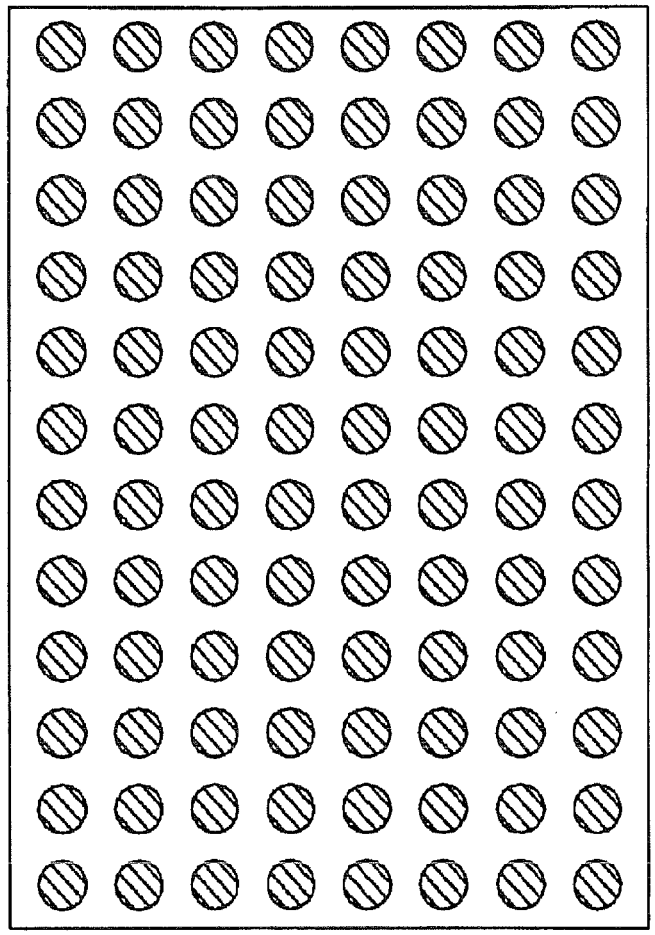
Figure 16E:
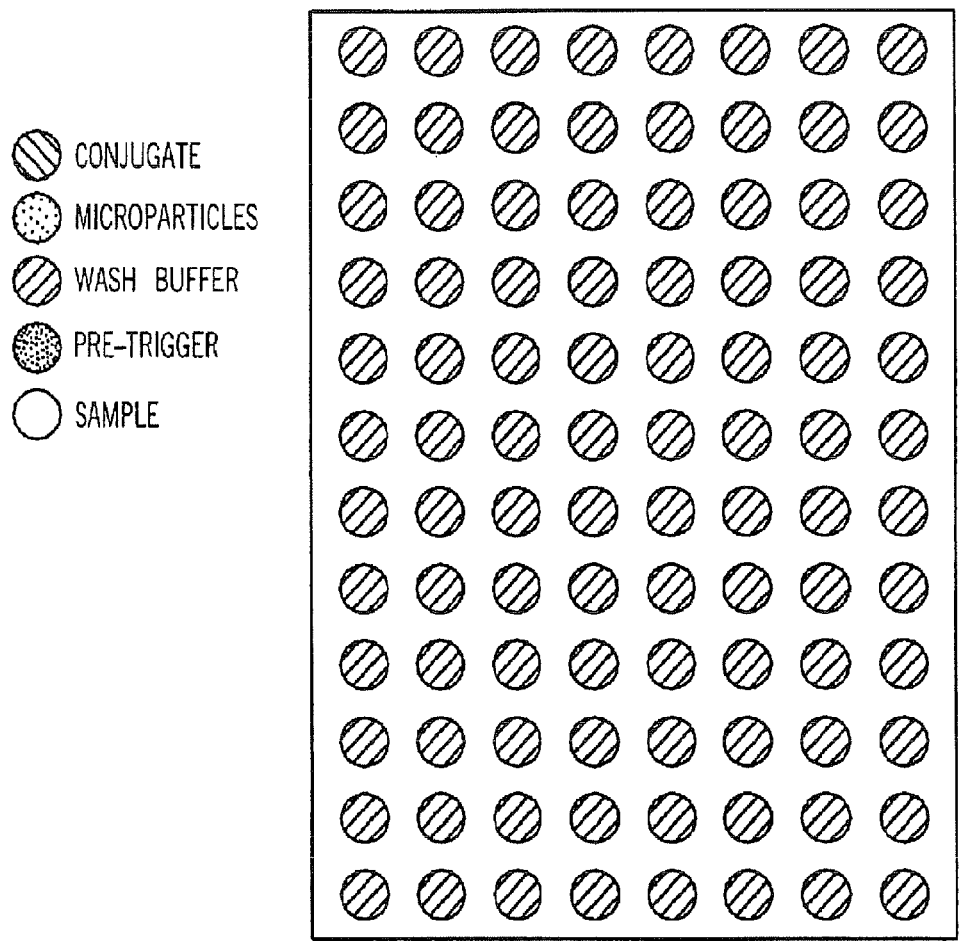
Figure 16F:
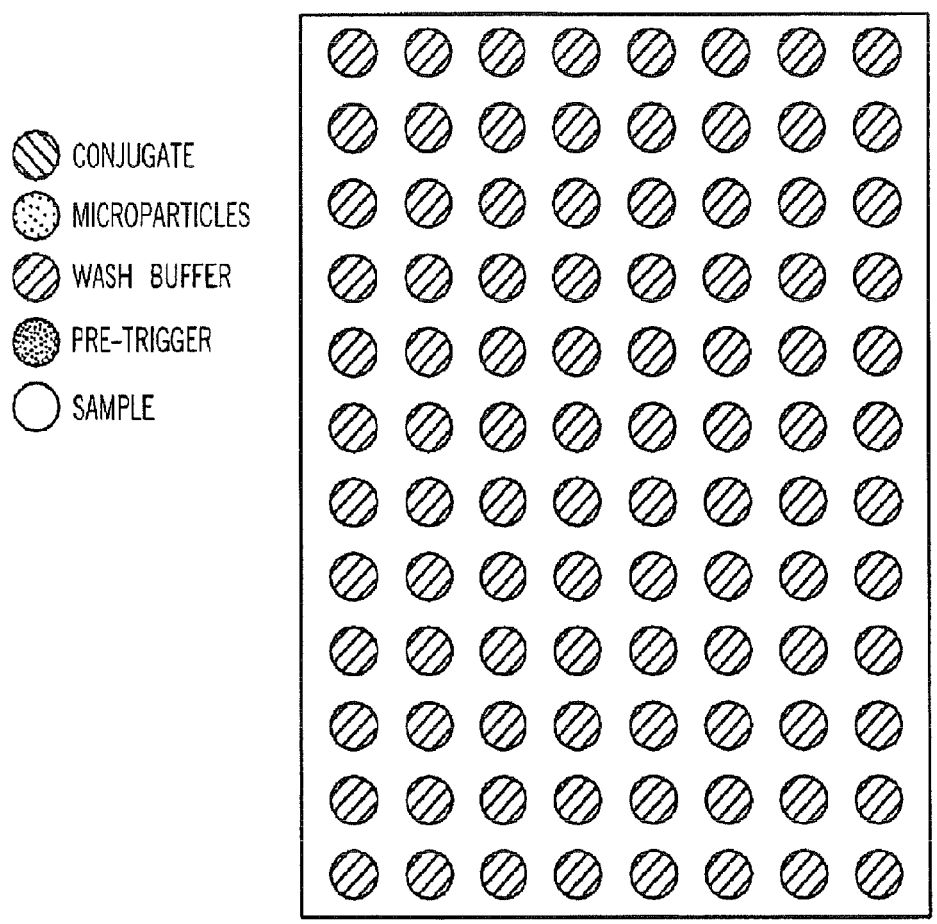
Figure 16G:
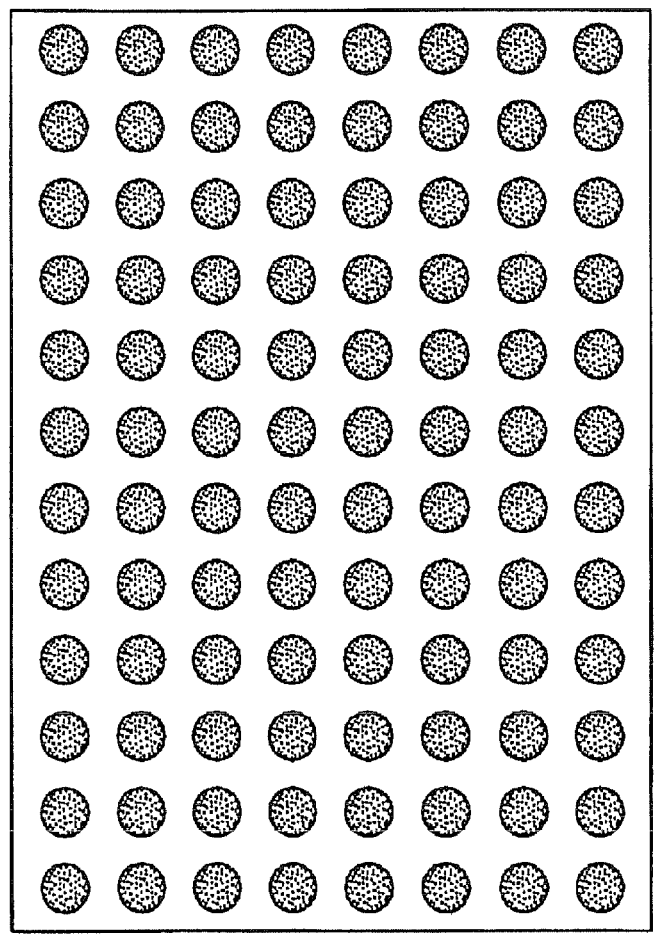

FIG. 14 illustrates the kitting of chemiluminescent microparticle immunoassays utilizing two micro-well plates, each micro-well plate having 96 micro-wells. Incubation of the initial sample and the magnetic microparticles are performed in the first row of the micro-well plate on the left. Nine subsequent rows (seven rows in the micro-well plate on the left and the first two rows in the micro-well plate on the right) can be used to accumulate additional antigen from the remaining volume of the sample. The processing requires two micro-well plates, but can utilize the same set of tip combs 164. Wash buffer is dispensed in the third, fourth, sixth, and seventh rows of the micro-well plate on the right. Conjugate is dispensed in the fifth row of the micro-well plate on the right. Pre-trigger solution is dispensed in the eight row of the micro-well plate on the right. Other kitting arrangements can be used in place of the kitting arrangements shown in FIGS. 13 and 14.

The principle of the operation of the magnetic particle processor 140 is based on the use of (a) magnetic rods 162 that can be covered with the tips or sheaths of disposable tip combs 164 and (b) micro-well plates. New tip combs 164 are installed in the magnetic particle processor 140 prior to processing each micro-well plate. A tip comb 164 comprises a strip of non-magnetic material that joins a plurality of tips, or sheaths, made of non-magnetic material, which tips, or sheaths, cover the magnetic rods 162. Commercially available tip combs comprise twelve tips for the KingFisher™ magnetic particle processor and 96 tips for the KingFisher™ 96 magnetic particle processor. The magnetic particle processor 140 is capable of functioning without any aspirating and/ or dispensing devices or components. The magnetic particle processor 100 is designed for a maximum of 96 micro-wells in a micro-well plate.

The dimensions of the micro-wells are compatible with the dimensions of the tip comb 164 and the tips, or the sheaths, thereof, with the result that the tips can be used to mix or agitate the contents of the micro-well. A single sample processing for an immunoassay can be carried out in a single micro-well plate containing 96 micro-wells. One tip comb 164 containing twelve (12) tips 164a, or sheaths, can be used for processing twelve (12) samples at one time.

The operating principle employed by the magnetic particle processor is inverse magnetic particle processing technology, commonly referred to as MPP. Rather than moving liquids from one micro-well to another micro-well, the magnetic particles are moved from one micro-well to another micro-well, e.g., from a micro-well in a given column and row of a micro-well plate to a micro-well in the same column and in another row of the micro-well plate, at least one micro-well containing reagent(s) required for the immunoassay. This principle stands in contrast to the external magnet method, which is used in such automated analyzers as the ARCHITECT® analyzer, commercially available from Abbott Laboratories, Abbott Park, Ill. According to inverse magnetic particle processing technology, magnetic particles are transferred with the aid of the magnetic rods 162 covered with the disposable, specially designed plastic tip combs 164.

Working with magnetic particles can be divided into at least six separate process steps:

Collecting particles: In this step, magnetic particles are collected from the micro-well specified.

Binding particles: In this step, material is collected onto the magnetic particles from the reagent in a specific micro-well.

Mixing particles: In this step, the reagent and particles (if inserted), are mixed with the plastic tip in a specific micro-well.

Releasing particles: In this step, the collected material is released from the surfaces of the magnetic particles into a specific micro-well.

Washing particles: In this step, the magnetic particles are washed in a specific micro-well.

Incubation of reaction mixtures: In this step the temperature of the reaction mixture is elevated to a sufficient level to obtain a satisfactory specific binding reaction. This step can be carried out at the same time as are the five steps listed previously. During the collection of the magnetic particles from the micro-wells of a micro-well plate, the magnetic rods 162 are fully enclosed by the tips, or the sheaths, of the tip comb 164. The magnetic rods 162 together with the tip comb 164 move slowly up and down in the micro-wells, and the magnetic particles are collected onto the walls of the tips, or the sheaths, of the tip comb 164. The magnetic rod 162 together with the tip comb 164, having collected the magnetic particles, can be lifted out of one column of micro-wells and transferred into the next column of micro-wells required by the process, etc. After collection of the magnetic particles, the magnetic rods 162 together with the tip comb 164 are lifted from the micro-wells, the magnetic rods 162 are lifted out of the tips, or the sheaths, and the tips, or the sheaths, of the tip comb 164 are lowered into the next micro-well containing a reagent. Magnetic particles are released by moving the tip comb 164 up and down several times at considerably high speed until all the particles have been mixed with the contents located in the succeeding row of micro-wells of the micro-well plate. This process can be carried out for twelve (12), twenty-four (24), or ninety-six (96) immunoassay reactions simultaneously.

Washing the magnetic particles is a frequent and an important phase of the magnetic particle processing activity. Washing is a combination of the release step and the collection step in a micro-well filled with a washing solution. To maximize washing efficiency in the micro-wells of a micro-well plate, the magnetic rods 162 together with the tip comb 164 are designed to have minimized liquid-carrying properties. To keep the suspension containing the magnetic particles evenly mixed in long-running reactions, the tip comb 164 can be moved up and down from time to time.

Inverse magnetic particle processing provides a micro-well plate format. Inverse magnetic particle processing eliminates the need for a process path of the type use in an ARCHITECT® analyzer, eliminates loaders for reaction vessels, eliminates mixers, and eliminates process path washing mechanisms, which typically operate in accordance with a fixed protocol. Inverse magnetic particle processing allows kitting and eliminates the need for time-dependent additions of critical reagents and other liquids.

FIGS. 15A, 15B, 15C, 15D, 15E, and 15F illustrate schematically basic elements of the inverse magnetic particle processing. FIG. 15A shows a suspension of magnetic particles in a micro-well before collection. FIG. 15B shows the collection of magnetic particles. FIG. 15C shows the transfer of magnetic particles from one micro-well to another micro-well. FIG. 15D shows the magnetic particles on the surface of a tip of the tip comb. FIG. 15E shows the release of magnetic particles in the micro-well. FIG. 15F shows a suspension.

The clinical chemistry assay processor 142 provides the following functions: incubation of reaction mixtures, mixing of reaction mixtures, performing a reading with a blank, performing a reading of a reaction mixture. An absorbance reader built into the clinical chemistry assay processor 142 is positioned at the sub-section 68 of the analysis section 60 to read the results of the clinical chemistry assay from the micro-well plates after the reaction mixtures are processed. The clinical chemistry assay processor 142 provides incubation of reaction mixture, mixing of reaction mixtures, and absorbance readings.

An eight-channel, 16-wavelength reader (340-850 nm) can be used to interleave reading with additions of a first reagent and a second reagent. A shaker/mixer is utilized for the addition of all reagents. Light and temperature are controlled in the reading area. An absorbance reader suitable for use in the apparatus described herein is commercially available from Molecular Devices under the trademark SpectraMax® II 384. See also, U.S. Pat. Nos. 6,188,476 and 5,959,738, both of which are incorporated herein by reference. This reader can operate at wavelengths ranging from about 190 nm to about 1000 nm. This reader can read an optical density of 0 to 4.0. A baseline read is performed on a fresh micro-well plate for each wavelength and each micro-well prior to any addition of liquid. Together with an offset value, which is based on a reading of water, the "blank read" can be calculated. The "water read" is an attempt to provide a background reference for the reading of a signal after reagents are added to the micro-well plate. The absorbance reading of the micro-well plate and the water is minimal, but still has some measurable value. By subtracting this measurable value for the signal read, the actual differential related to the concentration of the antigen can be determined. After reagents are added to the sample within a micro-well of the micro-well plate, the difference between the signal read and the blank read is used to calculate absorbance and the concentration of analyte. This type of calibration information is amenable to storage on a radio frequency identification tag that is attached to the micro-well plate.

This reader is equipped with a PathCheck® sensor. The PathCheck® sensor measures the depth (optical path length) of samples in a micro-well plate. SoftMax® Pro software can automatically normalize the well absorbance to a cuvette equivalent path length of 1 cm. This reader provides mixing and incubation of micro-well plates. This reader further enables the reading of a micro-well plate having 384 micro-wells, which can lead to reduction of the volume of liquid introduced into each micro-well.

Fluorescence polarization immunoassay (FPIA) capability can be added to the analyzer system described herein. A plate reader for fluorescence polarization immunoassay can be added and homogeneous assays performed. Equipment for carrying out fluorescence polarization immunoassays is well-known to those of ordinary skill in the art. Homogeneous assays can be performed in a manner that is substantially to the manner in which clinical chemistry assays are performed.

Sensing of levels of bulk liquids can be performed by the XYZ pipette. The XYZ pipette can determine the height of the liquid in a container in terms of motor steps and can then actuate replenishment of these liquids when the level of same is below a certain height. The XYZ pipette can sense the level of liquid in reagent containers 30. Empty reagent containers 30 can be disposed of into containers for solid waste. Reagent containers 30 for replenishing the supplies of reagents by means of transfer by the XYZ pipette can be supplied by the reagent inventory management system, described previously. Liquid height sensors attached directly to containers for bulk liquids can also determine the height of the liquid in the container and can actuate the replenishment of these bulk liquids when the level of the same is below a specified height.

The analysis section shown in FIGS. 1 and 5 is substantially similar to the analysis section shown in FIG. 6 with certain exceptions, all of which cause the analysis section shown in FIG. 6 to have a lower maximum throughput than the analysis section shown in FIGS. 1 and 5. Some of the differences between the analysis section shown in FIGS. 1 and 5 and the analysis section shown in FIG. 6 can include, for example, the number of immunoassay processors, the number of clinical chemistry assay processors, variations in number of racks for disposable tips, variations in number of racks for reusable tips, variations in number of stackers for disposable tips, variations in positioning of components in the analysis section 60 of the laboratory automation system 10. Other differences relate primarily to the placement of components in the analysis section 60 of the laboratory automation system 10. The major factors that determine throughput are the numbers of immunoassay processors and clinical chemistry assay processors.

The analysis section shown in FIG. 7 carries out immunoassays, but does not carry out clinical chemistry assays. However, immunoassay throughput is greatly increased relative to the analysis sections shown in FIGS. 1, 5 and 6. The analysis section shown in FIG. 7 exhibits some significant differences relative to the analysis sections shown in FIGS. 1, 5, and 6. Sub-sections 62 and 64 are substantially similar to those sub-sections shown in FIGS. 1, 5, and 6. However, the sub-section 66a of FIG. 7 utilizes six magnetic particle processors 140a that can be derived by modifying the KingFisher™ 96 magnetic particle processor and a plurality of luminescence readers 150, e.g., four luminescence readers. The stackers 146a for micro-well plates are located at or near sub-section 66a. Samples and reagents are kitted at the area 124a by means of the aspirating/dispensing device 94a, typically having twelve (12) pipettes. The kitting area 124b for the wash buffer and the pre-trigger solution is located near the stackers 146a. A high-speed reagent dispenser 94b is used to kit the micro-well plates with the wash buffer and the pretrigger solution. Movement of the micro-well plates to the luminescence readers 150 can be carried out by a conveyor belt 151a.

The aspirating/dispensing protocols, assay processing protocols, and reading protocols are functionally equivalent (i.e., same relative timing) to immunoassay assay protocols as are employed on the ARCHITECT® apparatus.

FIGS. 16A, 16B, 16C, 16D, 16E, 16F, and 16G illustrate micro-well plates to be kitted for immunoassays. Referring now to FIGS. 16A, 16B, 16C, 16D, 16E, 16F, and 16G each row of the micro-well plate for an immunoassay of the type illustrated in FIG. 13 is expanded to encompass an entire micro-well plate. However, no micro-well plate is employed to account for the row illustrated in FIG. 13 that is characterized by empty micro-wells. Thus, one complete micro-well plate is used for the introduction of samples along with microparticles, four complete micro-well plates are used for washing the reaction product with wash buffer, one complete micro-well plate is used for introducing conjugate, and one complete micro-well plate is used for introducing pre-trigger solution A total of seven micro-well plates is used, each micro-well plate corresponding to a row of the micro-well plate shown in FIG. 13. However, it should be noted that the column illustrated in FIG. 13 involving TEST 12 is not represented by any of the micro-well plates illustrated in FIGS. 16A, 16B, 16C, 16D, 16E, 16F, and 16G.

Initially, as three micro-well plates are kitted with the conjugate, three micro-well plates are kitted with wash buffer. The three micro-well plates containing wash buffer are placed into each of three immunoassay processors, one micro-well plate containing wash buffer per immunoassay processor, as shown in FIG. 7. Then the three micro-well plates containing conjugate are placed into the aforementioned three immunoassay processors, as shown in FIG. 7, one micro-well plate containing conjugate per immunoassay processor. While nine additional micro-well plates are being kitted with wash buffer and placed into the aforementioned three immunoassay processors (three micro-well plates containing wash buffer per processor), three additional micro-well plates are being kitted with samples and microparticles and placed into the aforementioned three immunoassay processors (one micro-well plate containing samples and microparticles per processor). Finally, three additional micro-well plates are kitted with pre-trigger solution and placed into the aforementioned three immunoassay processors (one-micro-well plate containing pre-trigger solution per processor). This entire process can be repeated for a second set of three immunoassay processors. A high-speed reagent dispenser 94b can be employed to kit the immunoassays rapidly.

Figure 18A:
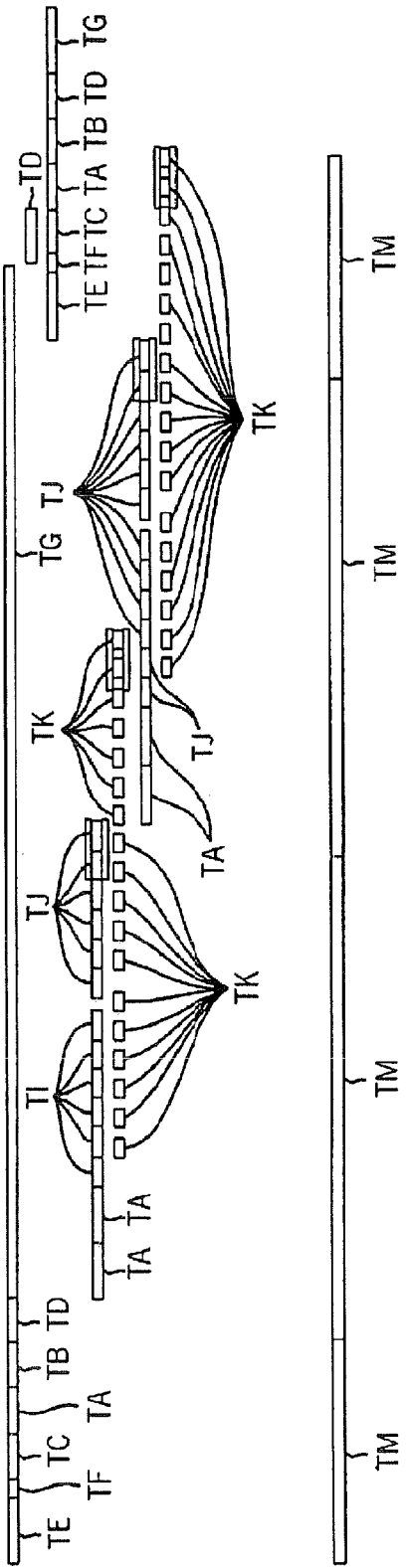
FIG. 18A is a chart illustrating interleaving of aspirating and dispensing protocols so that immunoassays can be carried out a higher than expected throughput rate.
Figure 18B:
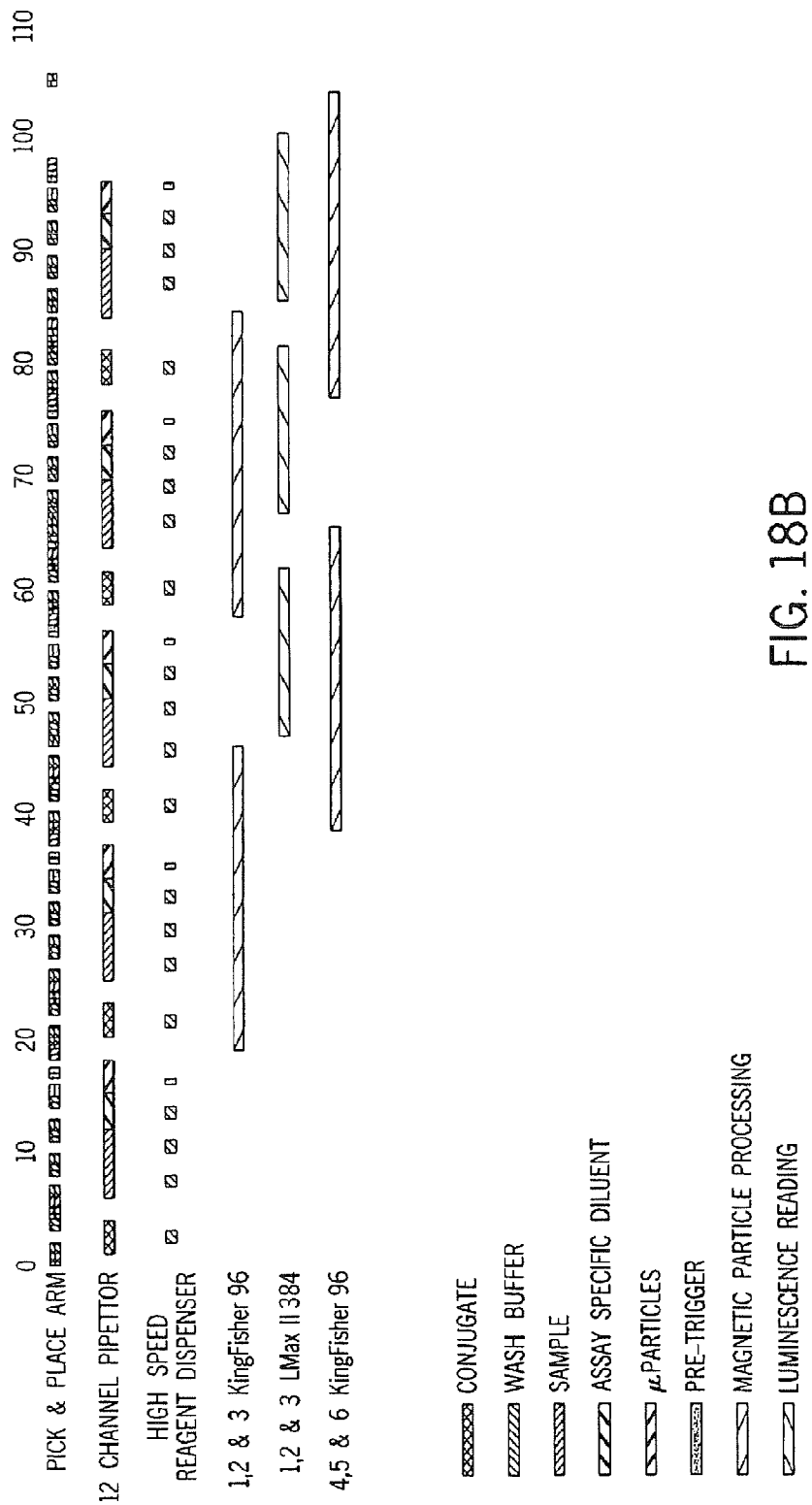
FIG. 18B is a chart illustrating interleaving of aspirating and dispensing protocols so that both immunoassays and clinical chemistry assays can be performed with a common set of resources.
Figure 19A:
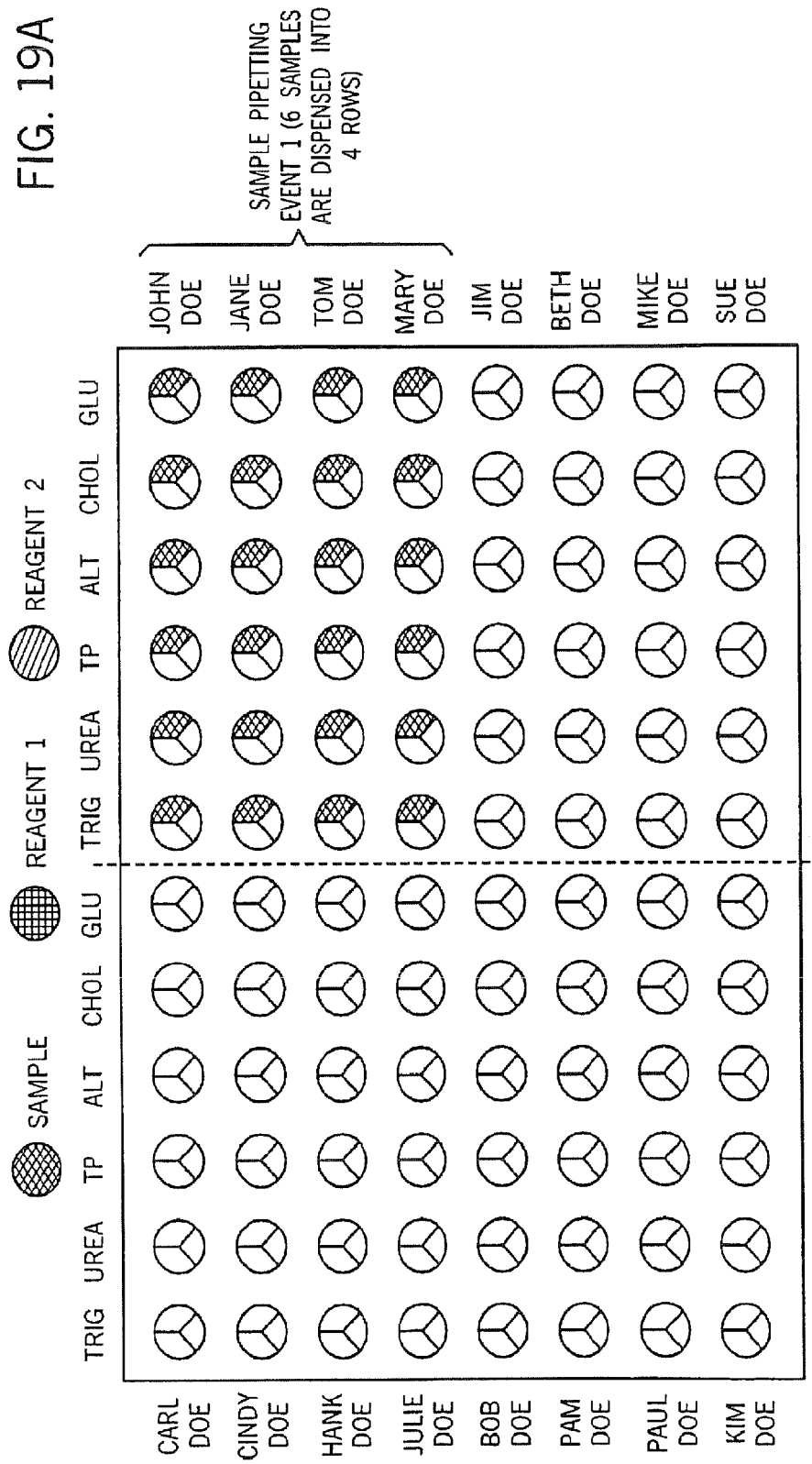
Figure 19C:
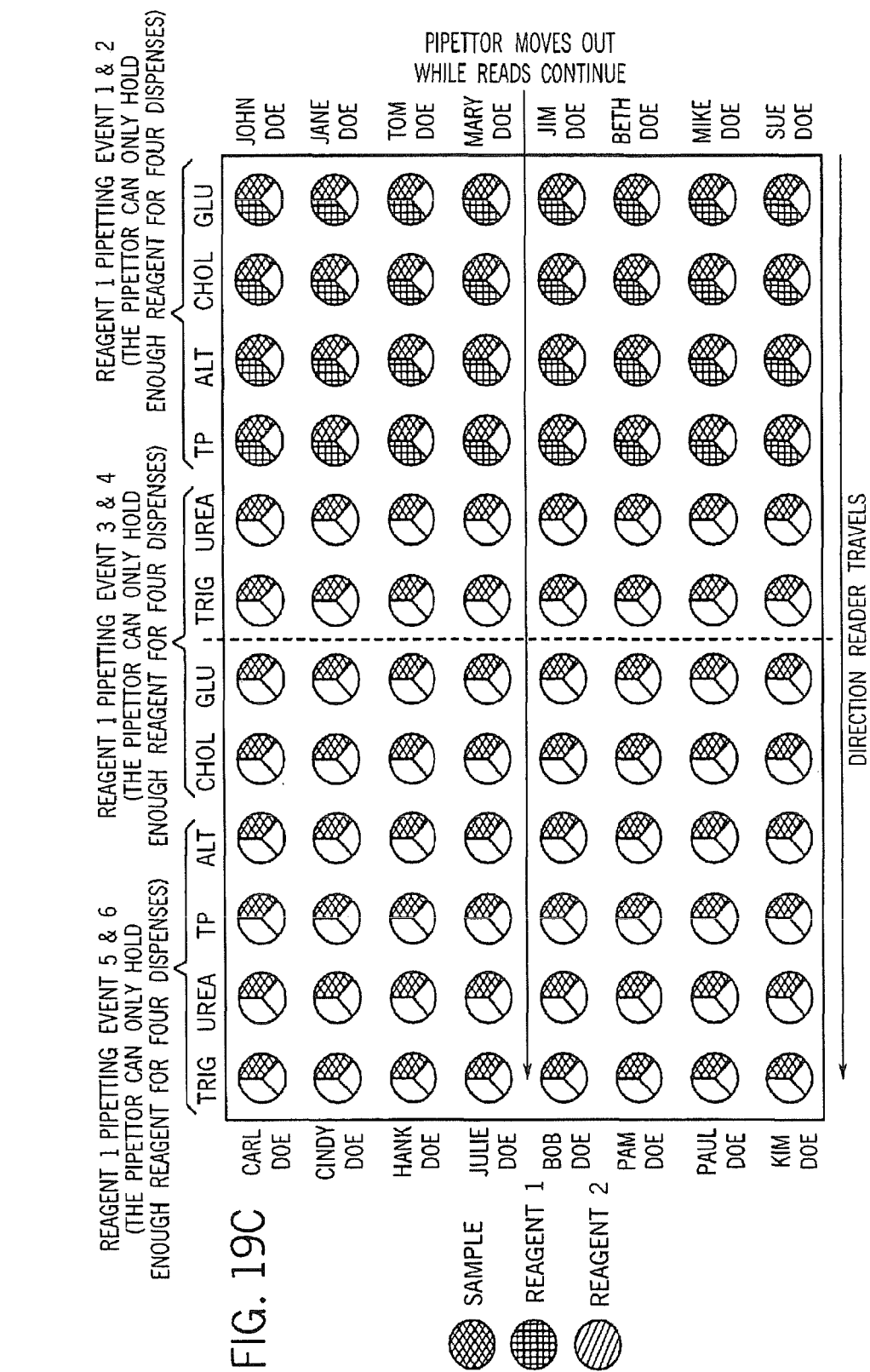
Figure 19D:
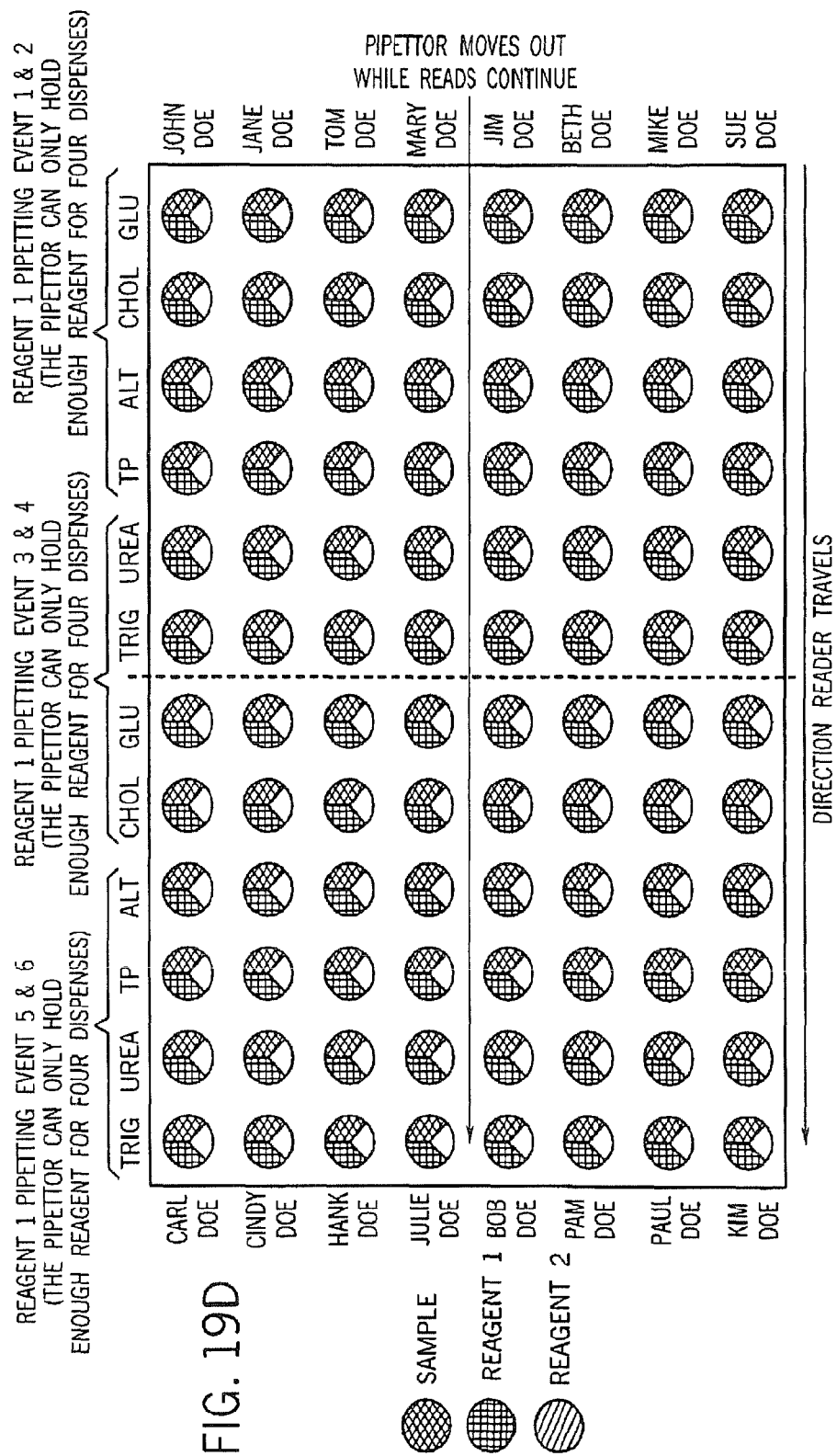
Figure 19E:
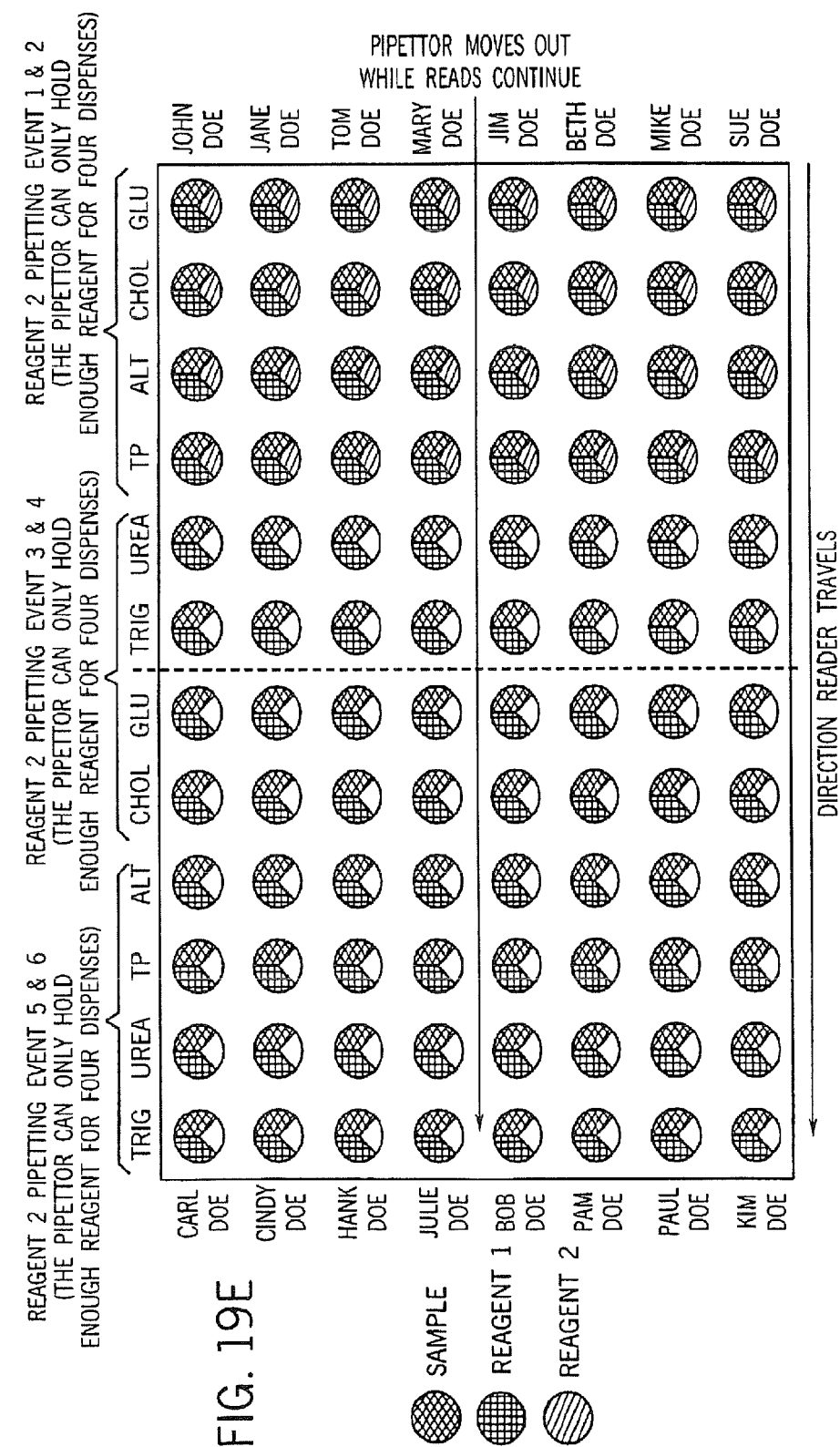
Figure 20A:
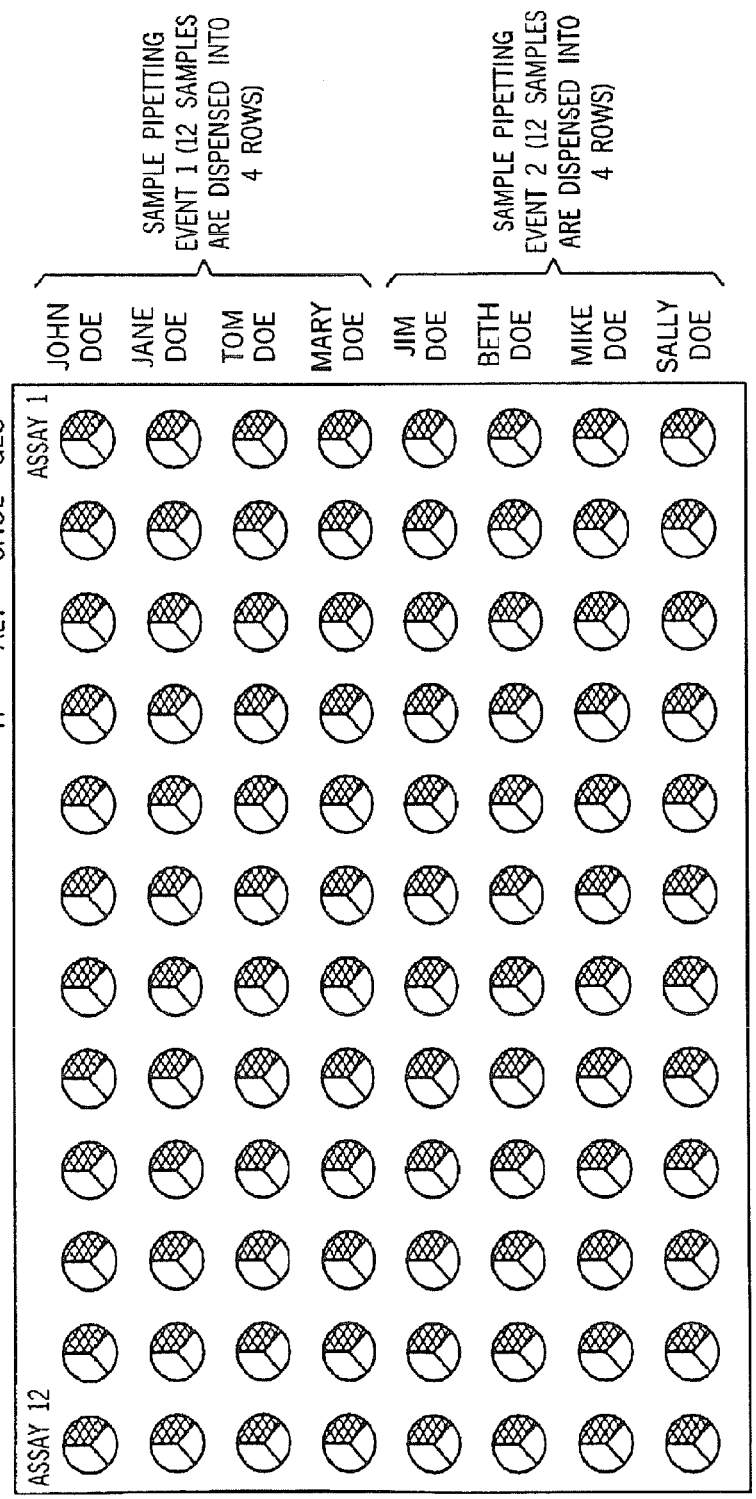
FIGS. 20A, 20B, 20C, 20D, and 20E are sequential top plan views of a single micro-well plate illustrating the dispensing of samples and reagents for twelve clinical chemistry assays for eight patients.
Figure 20B:
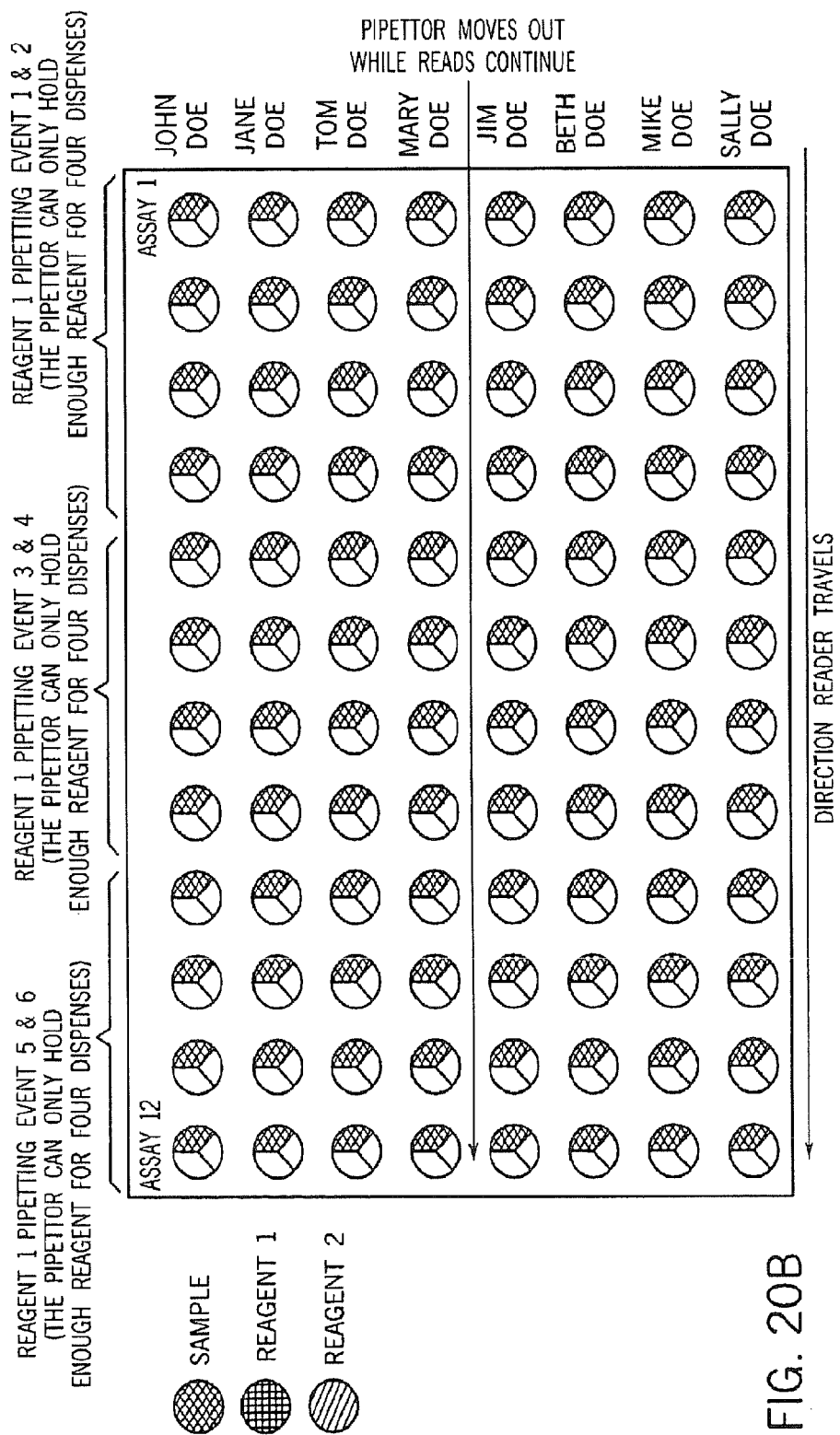
Figure 20C:
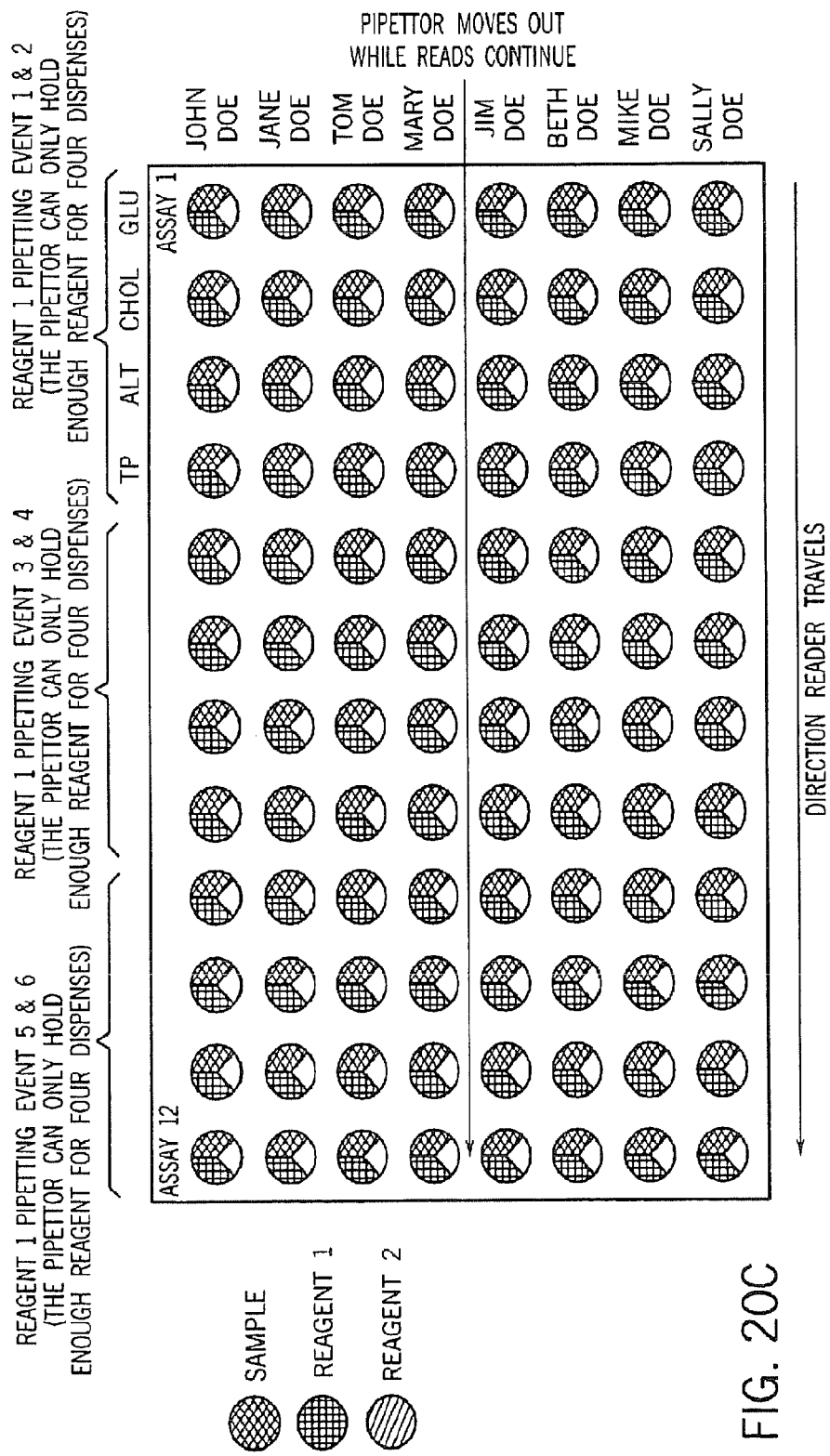
Figure 20D:
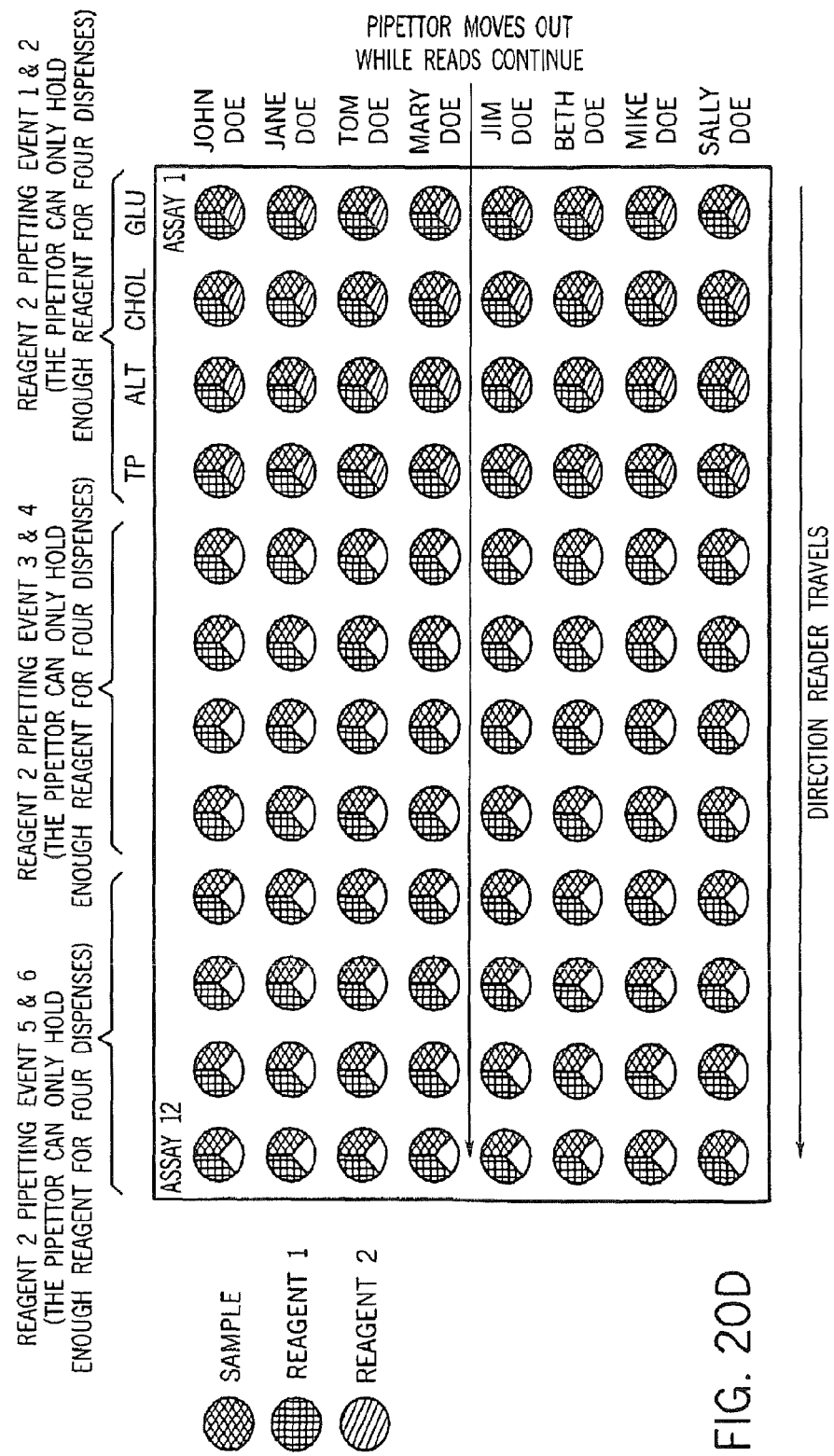
Figure 20E:
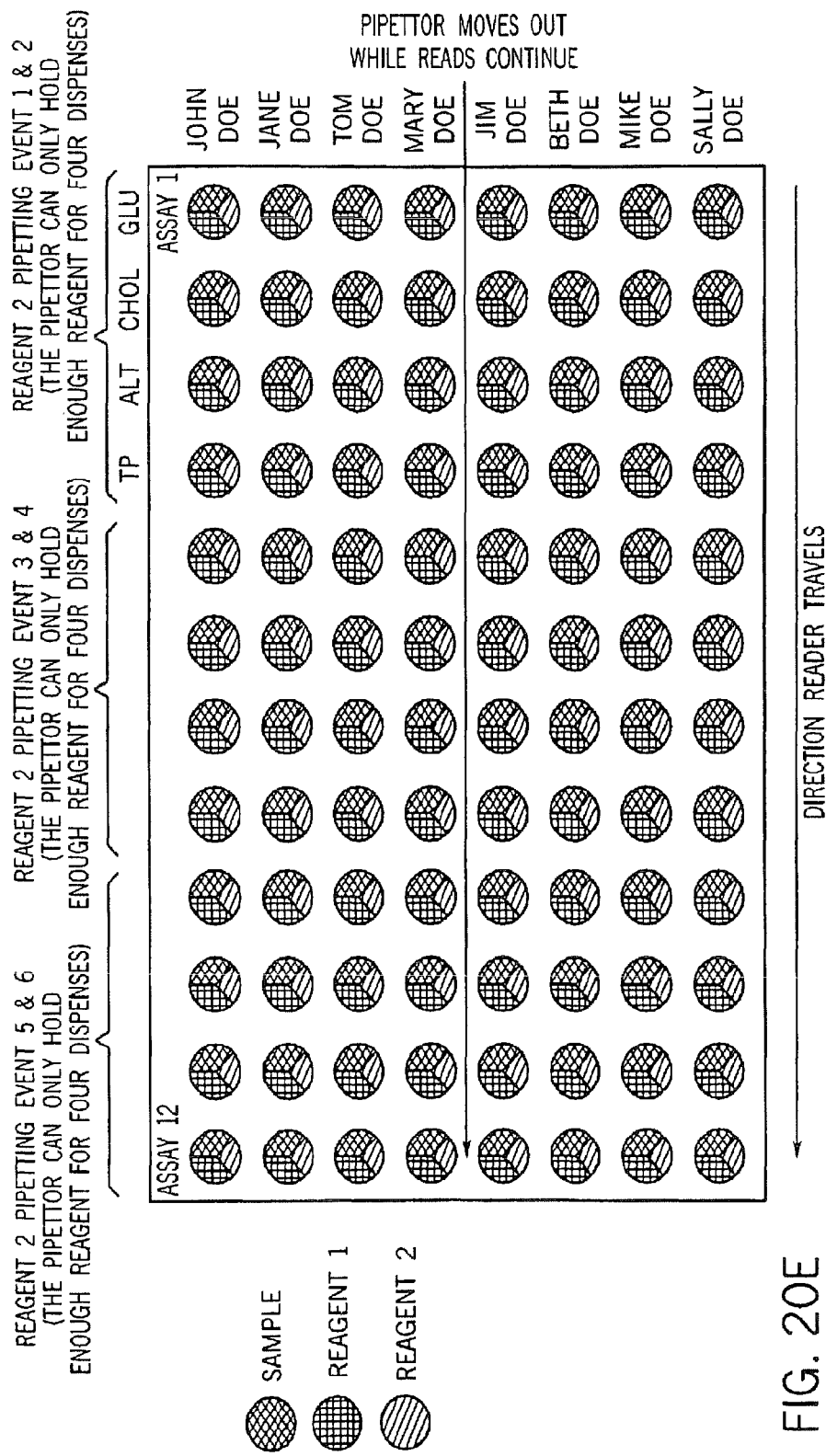
Figure 21A:
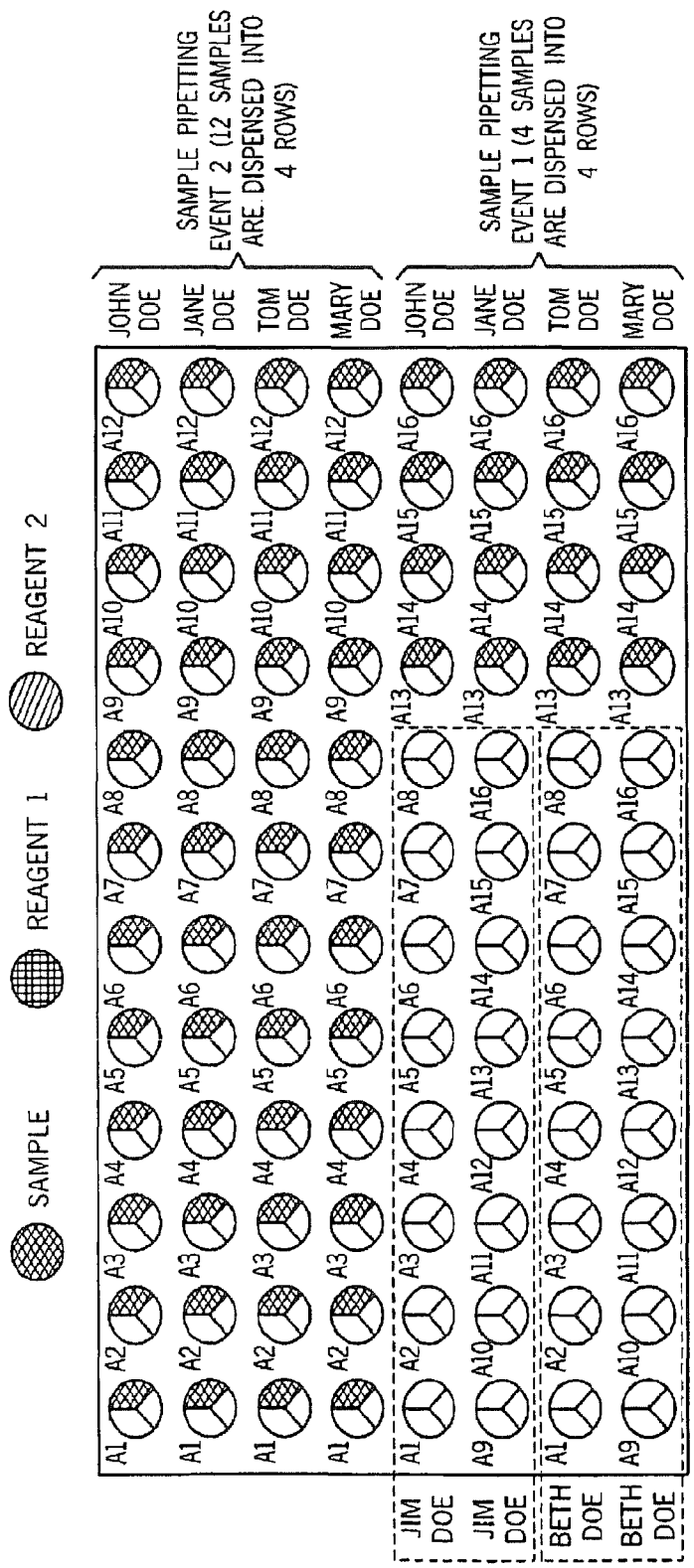
FIGS. 21A, 21B, 21C, 21D, 21E, and 21F are sequential top plan views of a single micro-well plate illustrating the dispensing of samples and reagents for sixteen clinical chemistry assays for six patients.
Figure 21B:
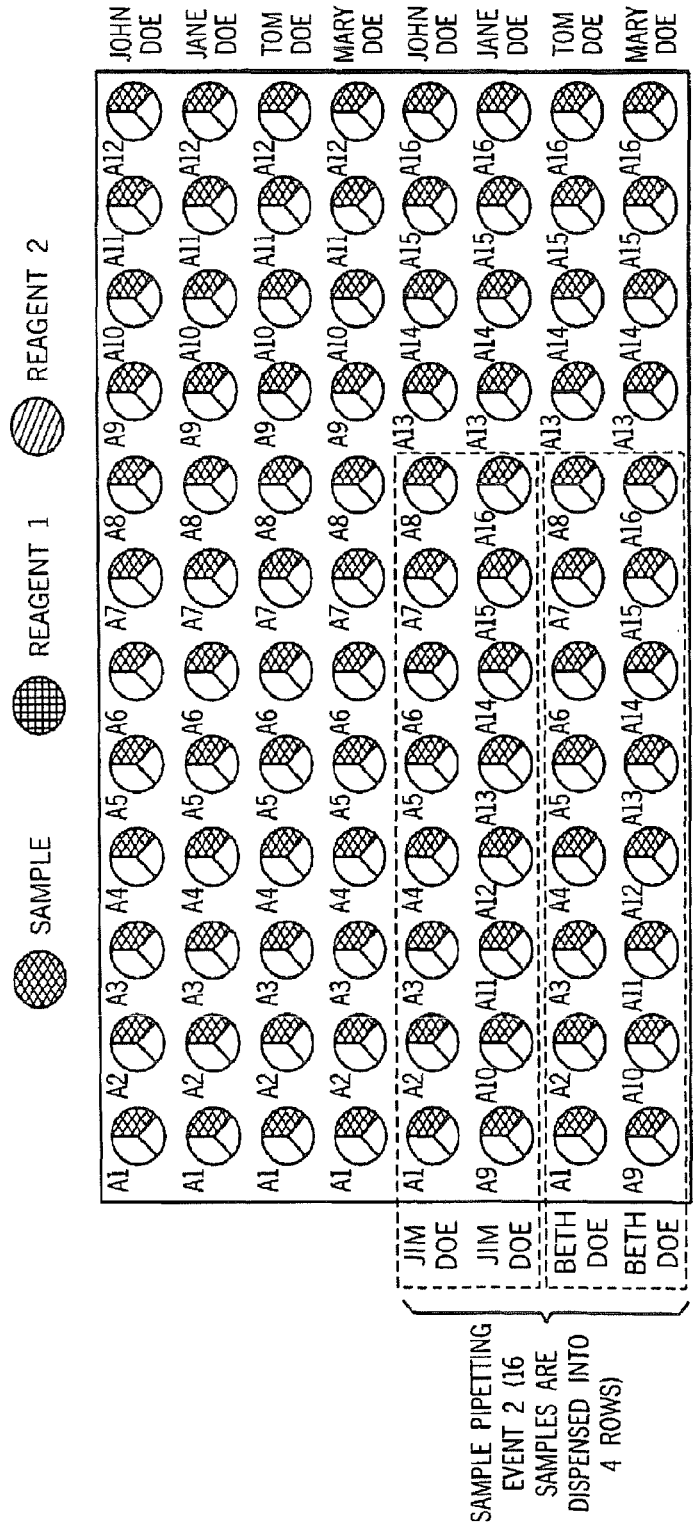
Figure 21C:
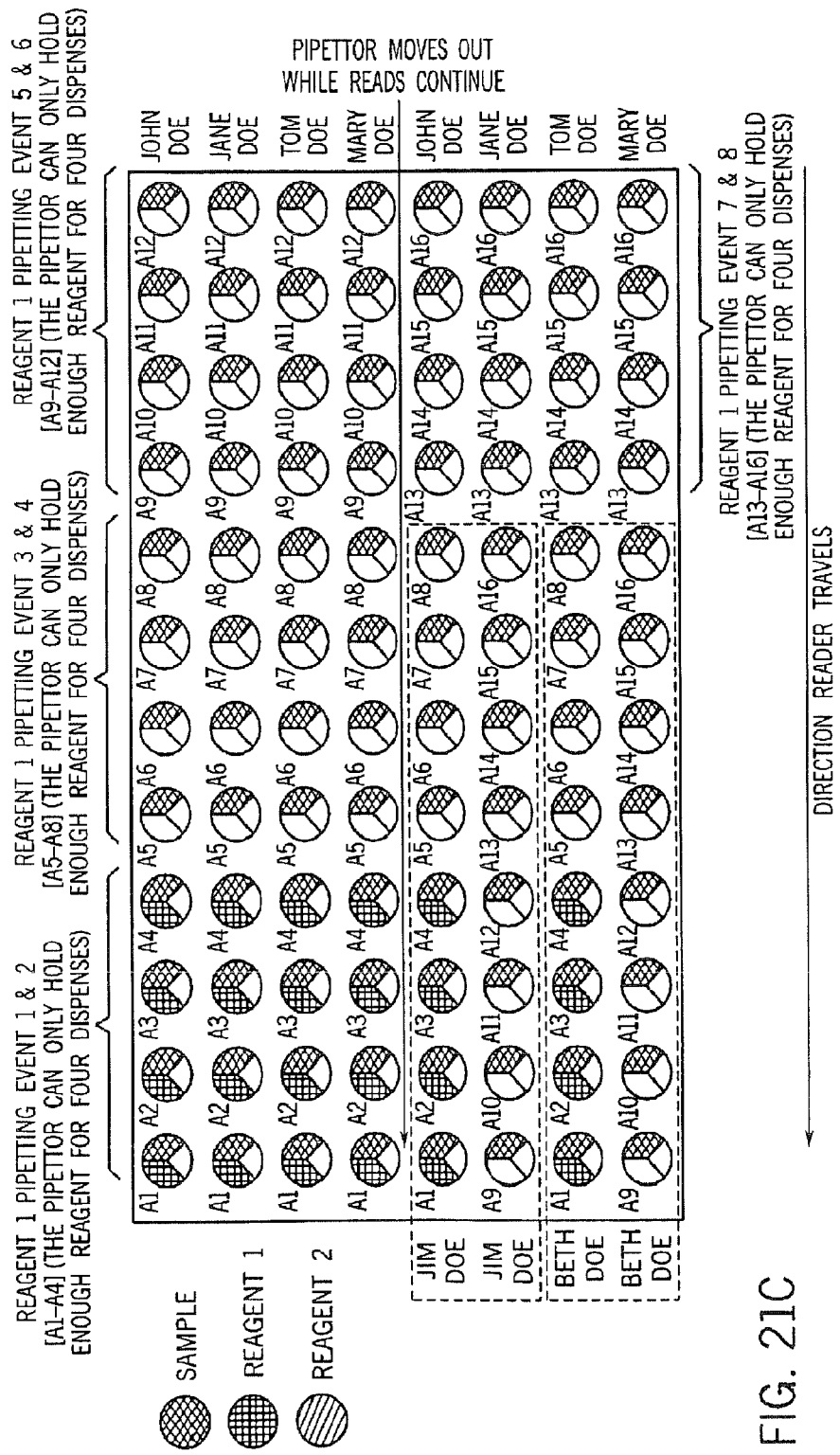
Figure 21D:
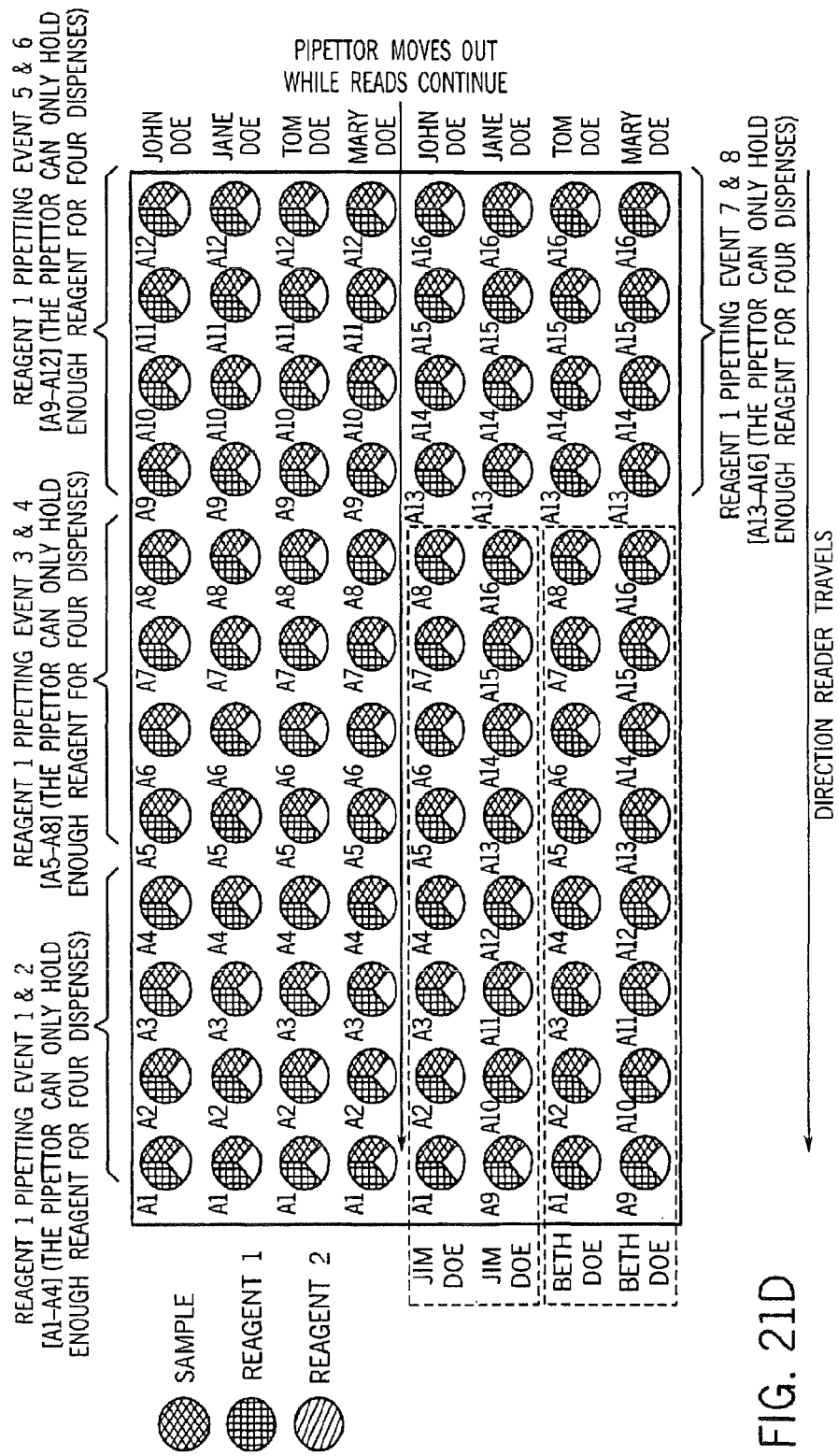
Figure 21E:
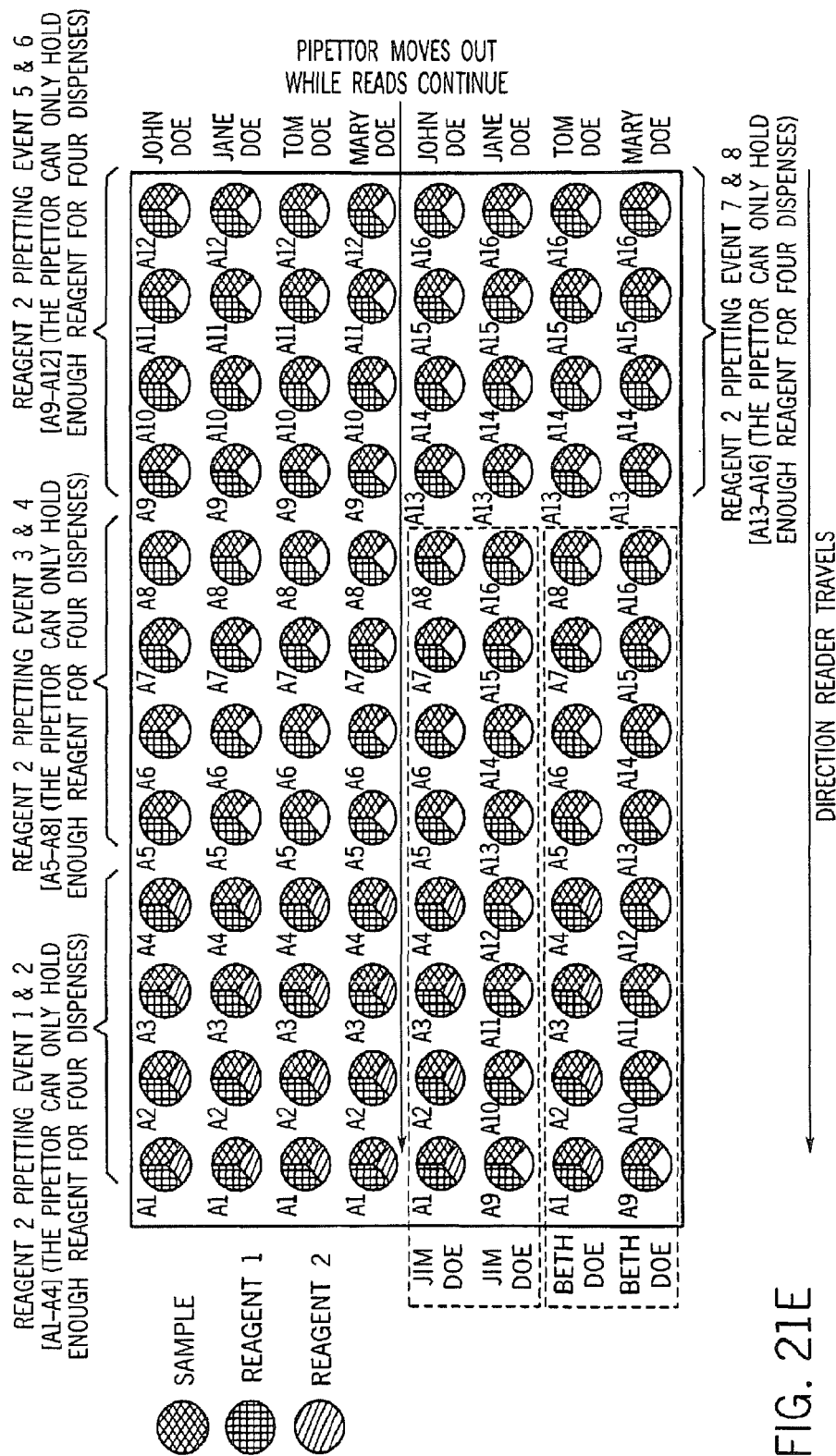
Figure 21F:
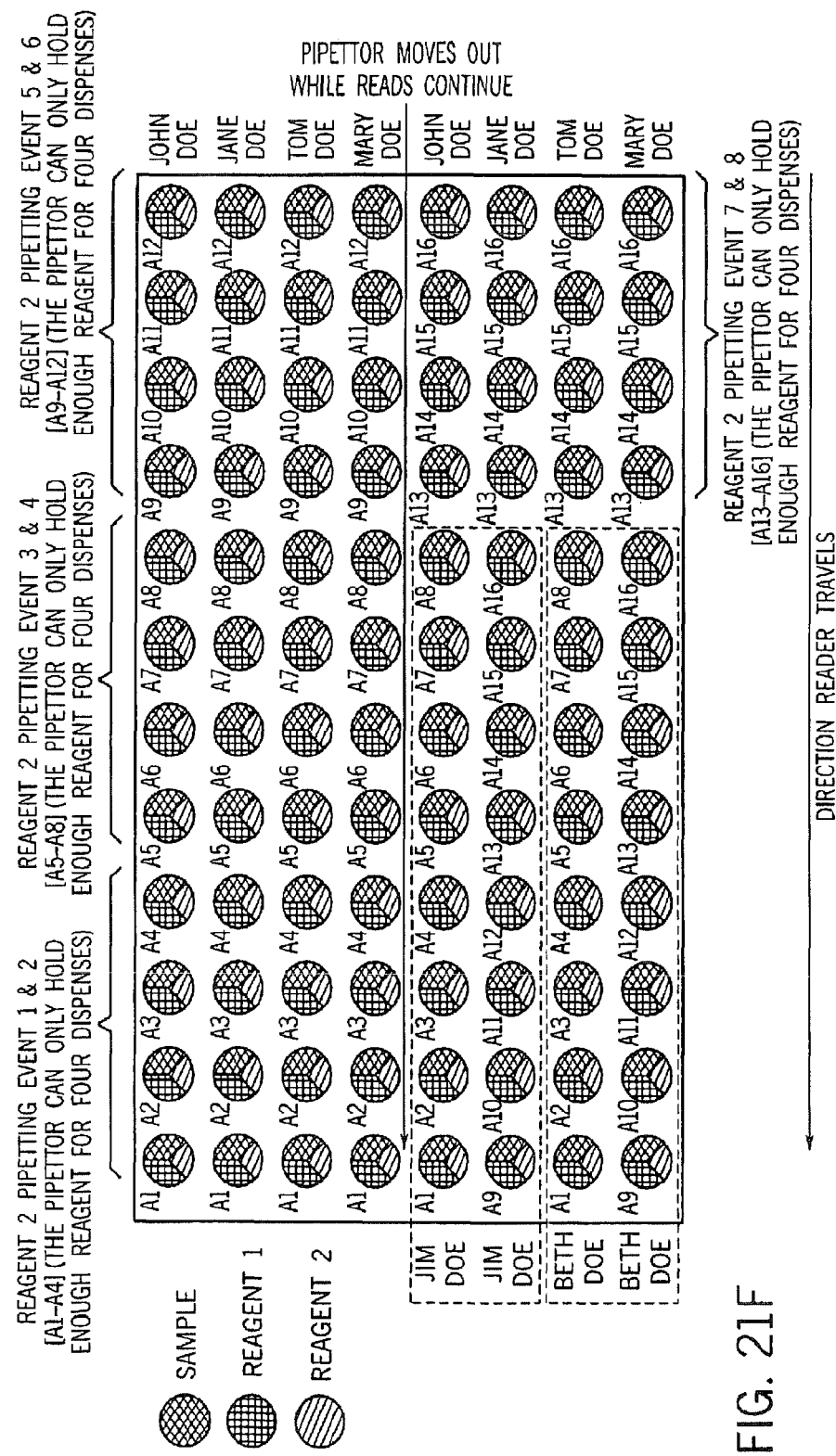
Figure 22A:
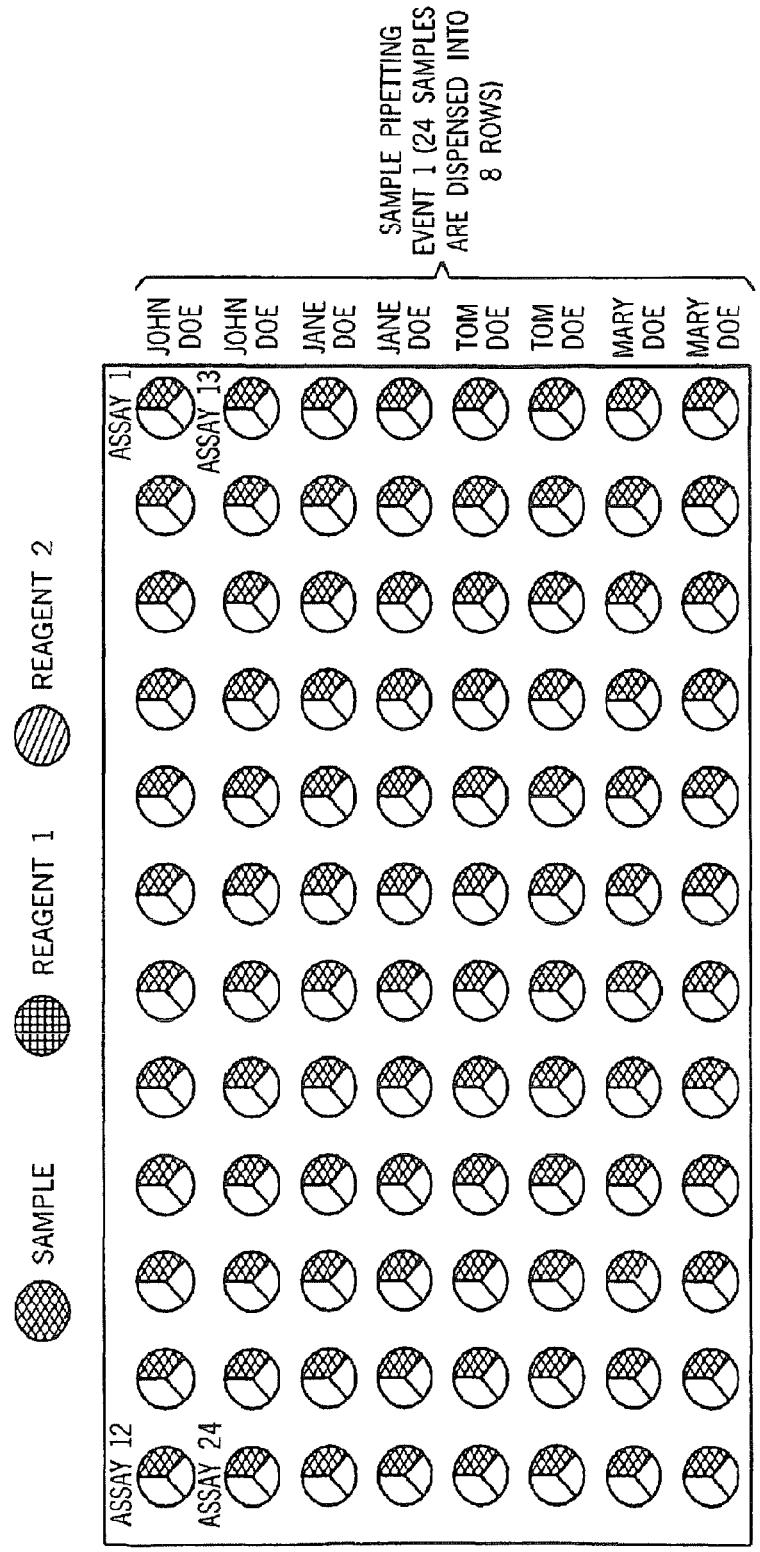
FIGS. 22A, 22B, 22C, 22D, and 22E are sequential top plan views of a single micro-well plate illustrating the dispensing of samples and reagents for twenty-four clinical chemistry assays for four patients.
Figure 22B:
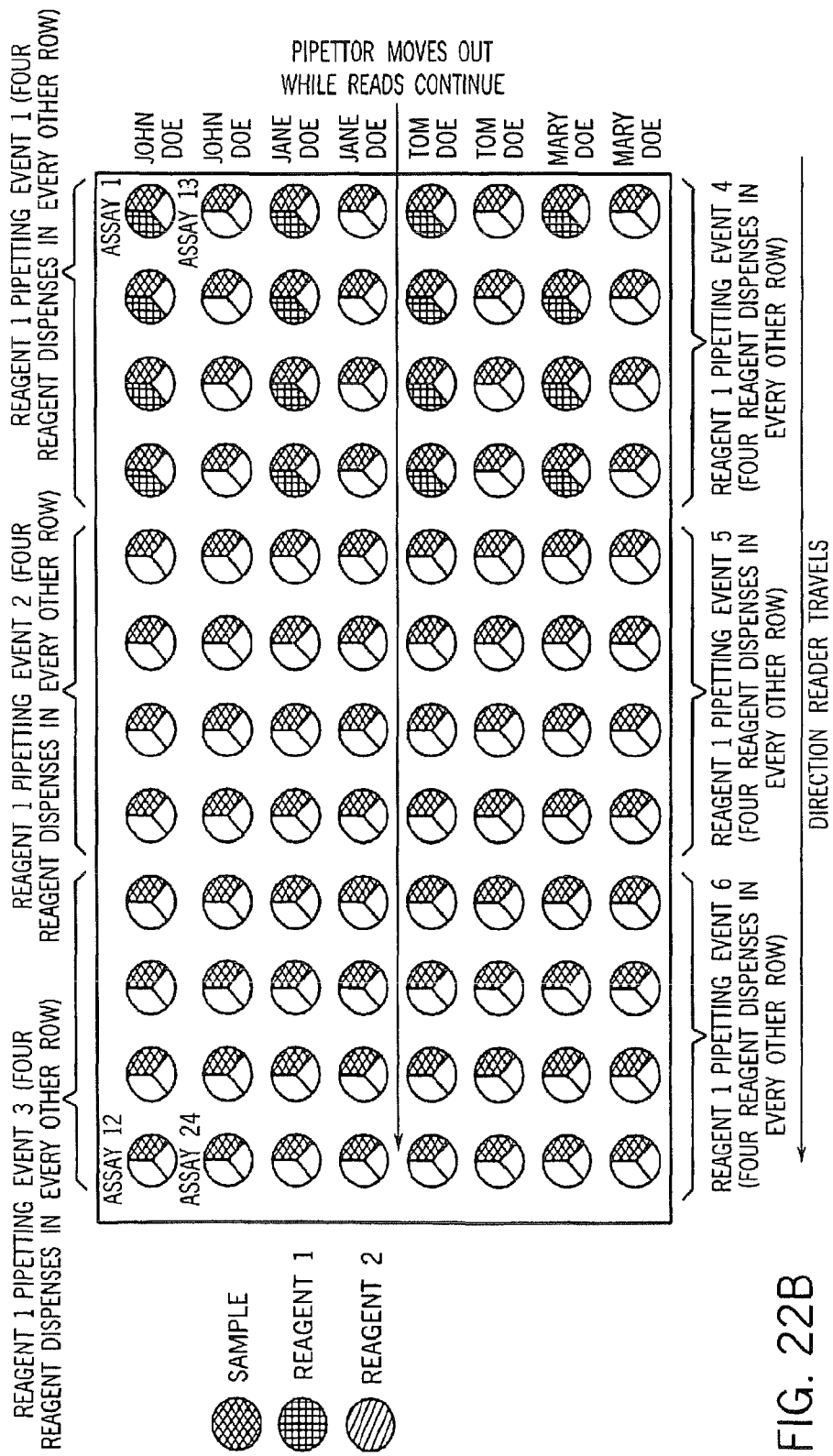
Figure 22C:
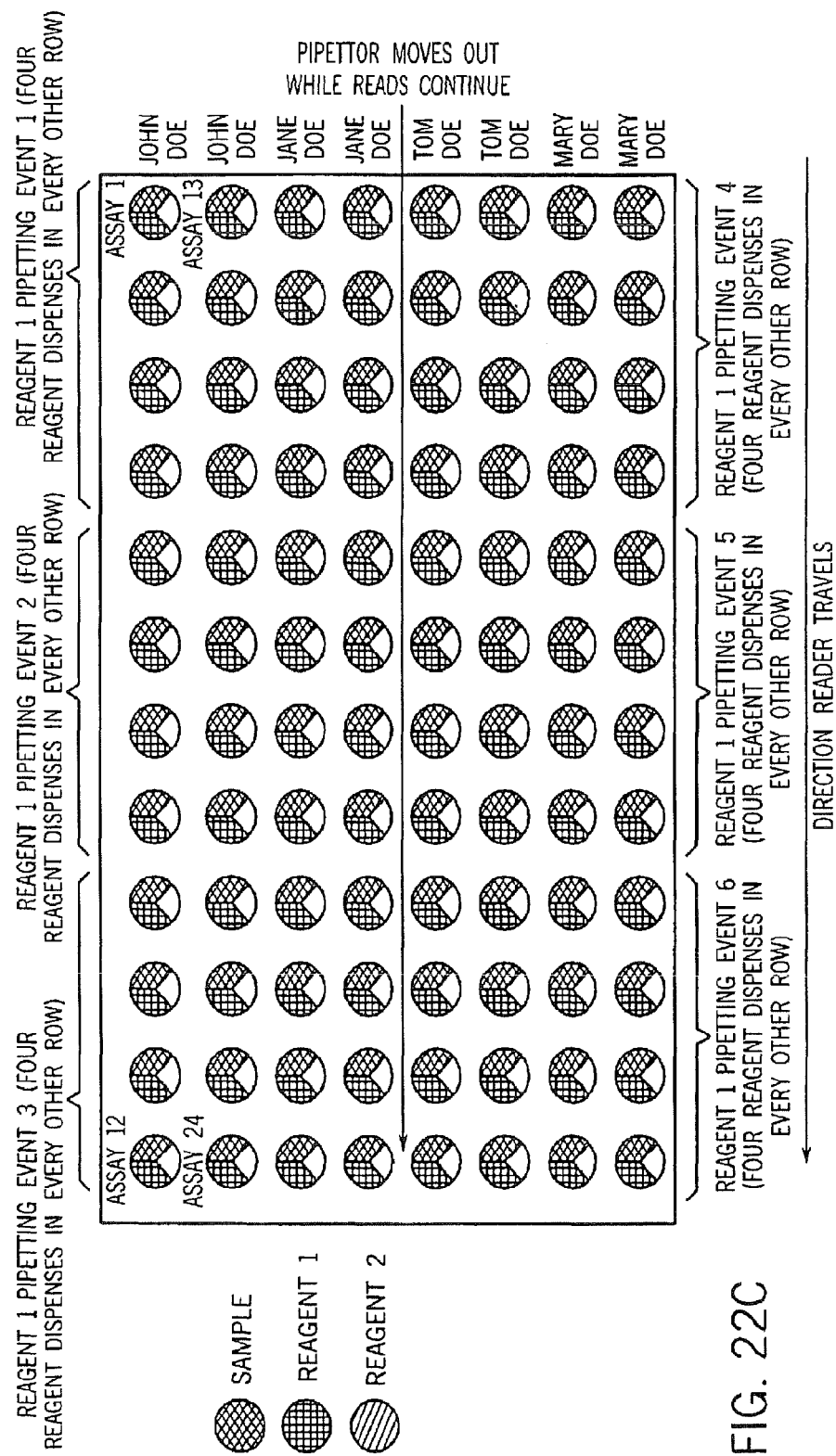
Figure 22D:
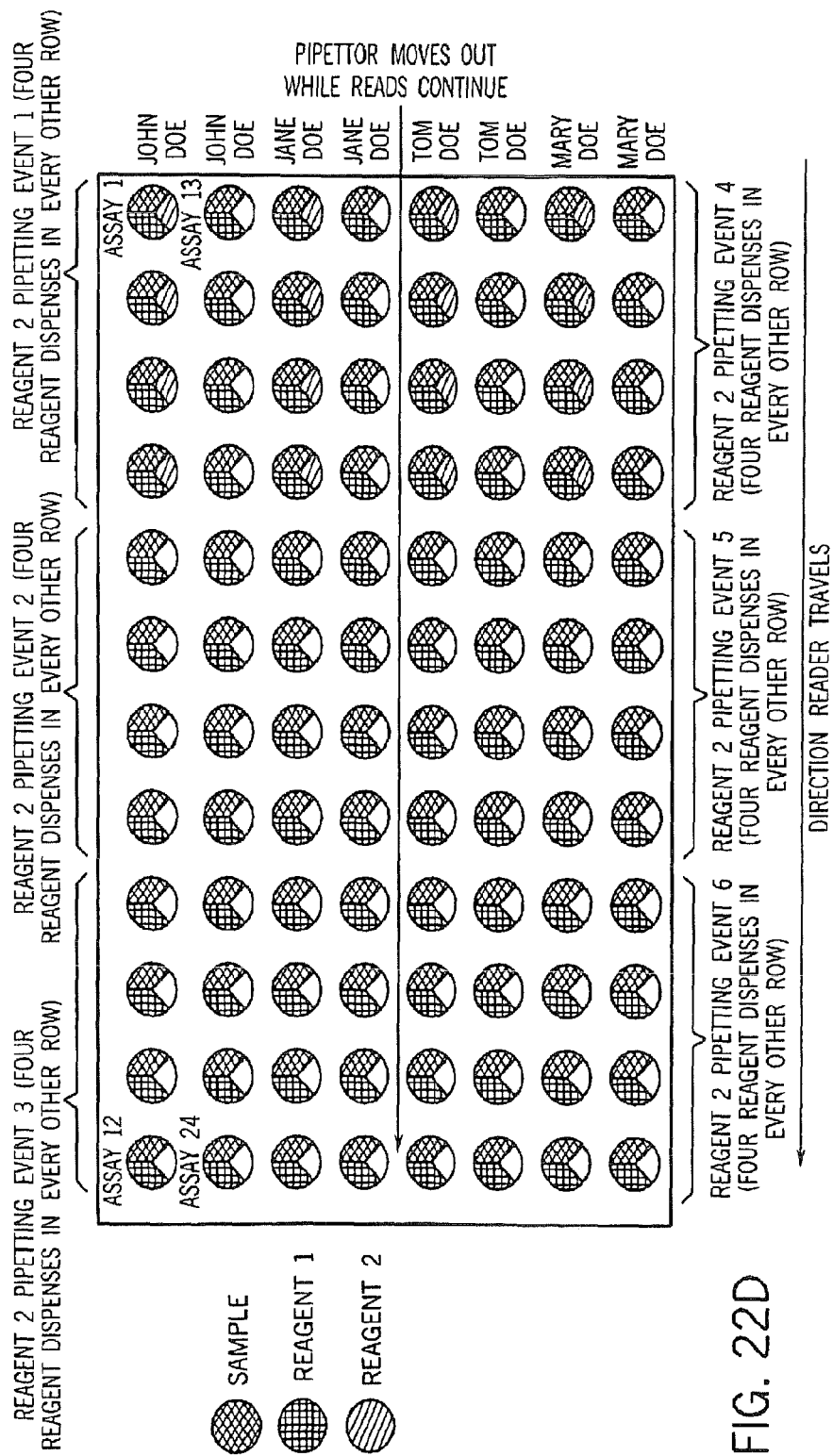
Figure 22E:
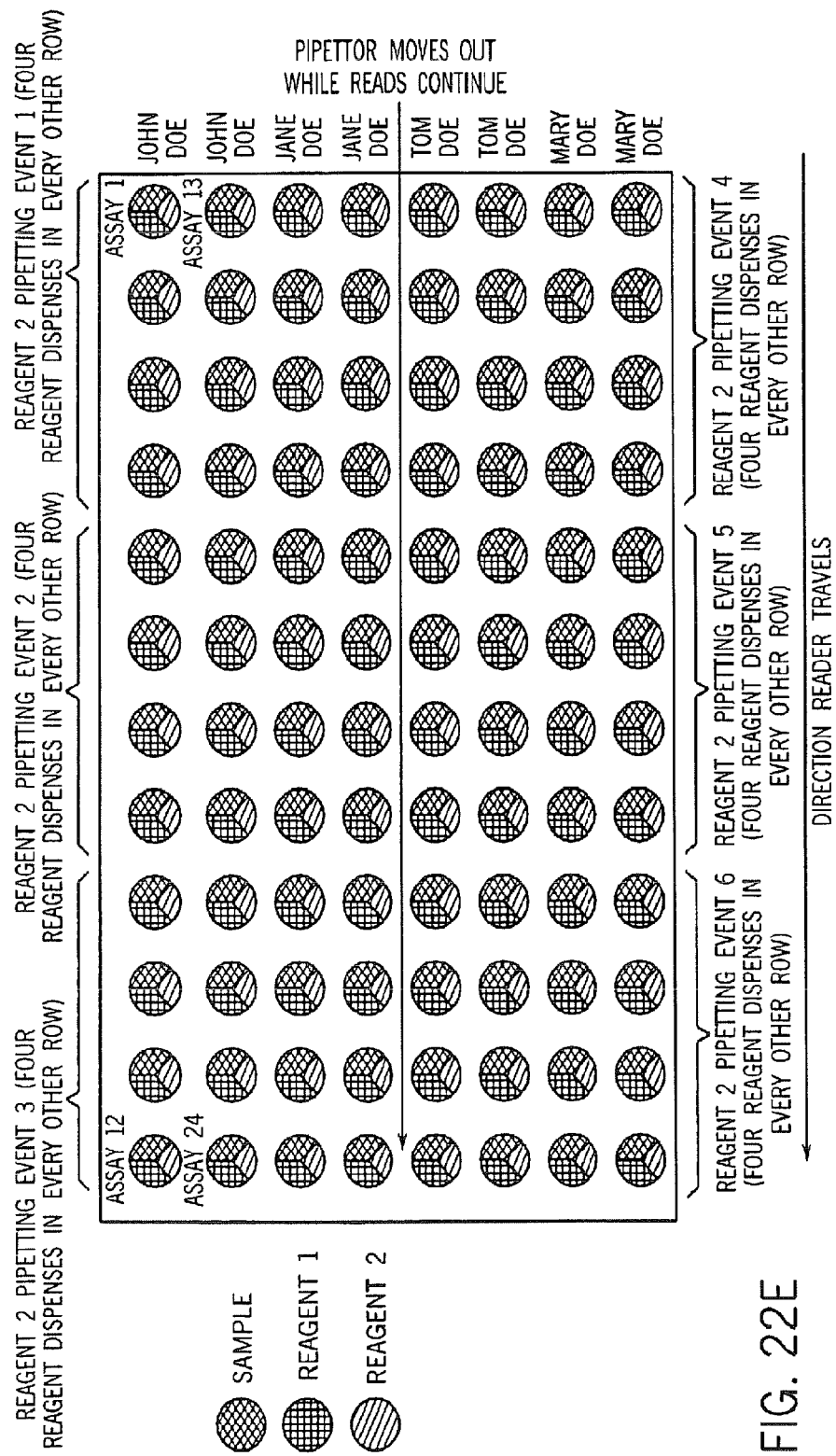

As the three immunoassay processors are completing the immunoassay protocols, three micro-well plates are transported to the three luminescence readers. FIG. 18B shows how these operations can be interleaved. Interleaving is intended to mean the switching the utilization of a given resource, e.g., an aspiration/dispensing device, when the next step in an assay protocol does not require that resource. For example, the aspiration/dispensing device is utilized for kitting micro-well plates for immunoassays until the kitting for the immunoassays is complete. Then the aspiration/dispensing device is used to process two micro-well plates designated for clinical chemistry assays. Thus, one resource is used for two different types of assay technologies. In conventional usage in the prior art, aspiration/dispensing devices are dedicated to either immunoassays or to clinical chemistry assay, not to both types of assays. Possibilities for modes of interleaving include, for example, (a) aspirating and dispensing samples and reagents for immunoassays and clinical chemistry assays, (b) reading clinical chemistry assays and adding reagents to micro-well plates for clinical chemistry assays, (c) incubating immunoassay mixtures in micro-well plates and adding reagents for homogeneous assays to micro-well plates, and (d) moving micro-well plates, dispensing bulk liquids, and aspirating and dispensing samples and reagents.

The aforementioned description involves the situation wherein the protocols for aspirating/dispensing for immunoassays and the protocols for aspirating/dispensing for clinical chemistry assays are interleaved. The description is based on the assumption that there are sufficient consumable materials and at least one test order for both immunoassays and clinical chemistry assays. In the event that there are no test orders or insufficient consumable materials for immunoassays, then only the aspirating/dispensing protocols for clinical chemistry assays will be performed. Similarly, if there are no test orders or insufficient consumable materials for clinical chemistry assays, then only the aspirating/dispensing protocols for immunoassays will be performed.

A sample dispensing area for clinical chemistry assays can be positioned at or near the sub-section 68 of the analysis section 60. Samples for from four to sixteen patients can be introduced to a micro-well plate to constitute one batch. Aspirating sufficient quantities of samples or reagents or both samples and reagents enables dispensing of a plurality of aliquots of samples or reagents or both samples and reagents without refilling the aspirating/dispensing device, thereby minimizing movement of the aspirating/dispensing device. The plate rotator 122 can be used to rotate the micro-well plate 900 for addition of clinical chemistry reagents. Rotation of the micro-well plate facilitates kitting of the clinical chemistry assays because the standard micro-well plate, which contains 96 micro-wells in an eight (8) micro-well by twelve (12) micro-well arrangement, is typically kitted by pipettes 98 driven by the head 96 of the aspirating/dispensing device 94, which moves in only one horizontal direction. In other words, the head 96 of the aspirating/dispensing device 94 can only move in one horizontal direction, for example, from left to right or from right to left. The samples are perpendicular to the assays. If the head 96 of the aspirating/dispensing device 94 is not rotatable 90°, the micro-well plate must be rotated 90° so that the same pipette head can be used to introduce samples into micro-wells and introduce reagents into micro-wells. Of course, if the head 96 of the aspirating/dispensing device 94 were rotatable, the micro-well plate would not have to be rotated.

Operation

The following discussion involves a single cycle of operation that includes both immunoassays and clinical chemistry assays. The operator loads sample containers 18 into the input/output module 20 and reagent containers 30 into the refrigerator. After the laboratory automation system 10 is programmed and activated, a robotic mechanism (not shown)

inserts reagent containers 30 into reagent container carriers 34 and sample containers 18 into sample container carriers 24. Then the laboratory automation system 10, by means of conveyors introduces the sample container carriers 24 into the appropriate queue 22 and the reagent container carriers 34 into the appropriate queue 32. The reagent containers 30 are placed in a temporary storage location by means of a robotic mechanism (not shown).

A micro-well plate is furnished for inverse magnetic particle processing by means of the aspirating/dispensing device 94. Another micro-well plate is furnished for clinical chemistry processing by means of the aspirating/dispensing device 94.

Reagent(s) are aspirated and dispensed from a reagent container(s) 30 for kitting for the inverse magnetic particle processing procedure by means of the aspirating/dispensing device 94. Reagent(s) are aspirated and dispensed from a reagent container(s) 30 for kitting for the clinical chemistry assays by means of the aspirating/dispensing device 94. Samples are aspirated from a sample container(s) 18 and dispensed into a first micro-well plate for the inverse magnetic particle processing procedure by means of the aspirating/dispensing device 94; samples are also aspirated from a sample container(s) 18 and dispensed into a second micro-well plate for clinical chemistry assays by means of the aspirating/dispensing device 94.

The micro-well plate that has been kitted for the inverse magnetic particle processing procedure is inserted into the magnetic particle processor 140 by means of the aspirating/dispensing device 94. The micro-well plate that has been kitted for the clinical chemistry assays is inserted into the clinical chemistry assay processor 142 by means of the aspirating/dispensing device 94.

The clinical chemistry reactions are carried out in the clinical chemistry assay processor 142 and the results of the clinical chemistry assays are read by the clinical chemistry assay processor 142. The inverse magnetic particle process is carried out by the magnetic particle processor 140. The micro-well plate from the magnetic particle processor 140 is removed from the magnetic particle processor 140 by the aspirating/dispensing device 94, placed on the conveyor belt 151, or delivered to a robotic mechanism, and transferred into the luminescence reader 150 to read the results of the immunoassays. After the results of the immunoassays are read by the luminescence reader 150, the aspirating/dispensing device 94 removes the micro-well plate from the luminescence reader 150 and disposes the micro-well plate into waste or recycles the micro-well plate, if desired. After the results of the clinical chemistry assays are read by the absorbance reader 142, the aspirating/dispensing device 94 removes the micro-well plate from the absorbance reader 142 and disposes the micro-well plate into waste or recycles the micro-well plate, if desired.

The aforementioned operation is extremely flexible; protocols other than those described above can be used. For example, immunoassays need not be run when clinical chemistry assays are being run; clinical chemistry assays need not be run when immunoassays are being run. In addition, each of the generic steps recited set forth above can be carried out in numerous ways.

After the reagent containers 30 and the sample containers 18 are properly positioned in appropriate queues 32, 22 in the analysis section 60 of the laboratory automation system 10 for kitting samples and reagents, the aspirating/dispensing protocols, the assay processing protocols, and the reading protocols for immunoassays can be the same as those employed by the ARCHITECT® system, with respect to timing. See U.S. Pat. Nos. 5,795,784 and 5,856,194, both of which are incorporated herein by reference. Of course, the magnetic particle processing technique described herein is extremely different from the immunoassay technique used in the ARCHITECT® system.

Protocols for aspirating and dispensing the samples and the reagents can be interleaved in the method described herein, thereby maximizing the utilization of the aspirating/dispensing device and the efficiency of the aspirating/dispensing device and reducing redundant aspirating/dispensing resources for both immunoassays and clinical chemistry assays. Furthermore, through the use of interleaving, a collision between one aspirating/dispensing device and another aspirating/dispensing device can be eliminated.

The general procedure for interleaving immunoassays and clinical chemistry assays involves at least the following steps:
(1) A first micro-well plate is kitted for an immunoassay and placed in the magnetic particle processor 120. One micro-well plate is kitted for each available immunoassay analyzer.
(2) While this first micro-well plate is being processed in the magnetic particle processor, samples are aspirated from a sample container(s) and dispensed into a clinical chemistry assay micro-well plate. Subsequently, the micro-well plate for the clinical chemistry assays is rotated 90° and placed in the micro-well plate absorbance reader 142.
(3) Aspirating/dispensing clinical chemistry reagent and absorbance reading of clinical chemistry assay results are interleaved, as they currently are for ARCHITECT® clinical chemistry assays. FIGS. 18A and 18B illustrates how the aforementioned interleaving feature can be carried out. FIG. 18A shows how interleaving can be used in a situation where both immunoassays and clinical chemistry assays are involved. FIG. 18B shows how interleaving can be used in a situation where only immunoassays are involved.

It should also be noted that processes for extracting nucleic acid(s) from samples and processes for amplifying nucleic acid(s) can also be integrated with immunoassays and clinical chemistry assays. In other words, interleaving can be carried out for (a) a plurality of immunoassays, or (b) a plurality of clinical chemistry assays, or (c) a plurality of extractions of nucleic acid(s) and a plurality of amplifications of nucleic acid(s), or (d) any combination of two or more of the foregoing (a) immunoassays, (b) clinical chemistry assays, and (c) extractions of nucleic acid(s) and amplifications of nucleic acid(s).

The following non-limiting examples further illustrate how immunoassays and clinical chemistry assays can be carried out with the laboratory automation system described herein.

EXAMPLE 1

This example illustrates how an immunoassay can be performed by means of inverse magnetic particle processing followed by reading results by means of a luminescence reader.

The magnetic particle processing steps can be carried out by means of inverse magnetic particle processing, with the steps of binding, collecting, washing, mixing, separating, and incubating being carried out in the micro-wells of a micro-well plate. Referring now to FIG. 13, a micro-well plate having eight (8) rows and twelve (12) columns is illustrated. A different assay is carried out in each column. A different process step is carried out in each row. In some rows, the process steps are varied on account of variations in the protocol of the assay. For each assay, the micro-well in the first row is blank. In each micro-well in the second row of the first eleven assays the sample is combined with the magnetic microparticle reagent. In each micro-well in the third row, the fourth row, the sixth row, and the seventh row for the first eleven assays, a wash buffer is present. In each micro-well in the fifth row for the first eleven assays the conjugate is present. In each micro-well in the eighth row for the first eleven assays, the pre-trigger solution is present. In the twelfth assay, the micro-wells in the first, second, third, and fourth rows are blank. In the micro-well in the fifth row, the sample, the magnetic microparticle reagent, and the conjugate are present. In the twelfth assay, in the micro-wells in the sixth and seventh rows, a wash buffer is present. In the twelfth assay, in the micro-well in the eighth row, the pre-trigger solution is present. Required incubation steps are performed on the entire micro-well plate. The amount of time that magnetic microparticles remain in a micro-well is deemed the incubation time or a portion thereof. By moving and incubating the magnetic microparticles through the various micro-wells containing the sample, the wash buffer, the conjugate, and the pre-trigger solution, chemiluminescent microparticle immunoassays can be processed in the same manner, with respect to functional steps, as they are in chemiluminescent microparticle immunoassays carried out by an ARCHITECT® analyzer. After the magnetic microparticles are incubated in the micro-wells containing the pre-trigger solution, the luminescent material, e.g., acridinium, is released and the quantity of photons emitted is determined by a luminescence reader. The micro-well plate can be transferred from the inverse magnetic particle processor to the luminescence reader by means of a conveyor belt or a suitable alternative thereof. Various robotic devices can be employed to move the micro-well plates into and out of the inverse magnetic particle processor(s) and the luminescence reader(s). Typically, such a robotic device selects a micro-well plate, grips the micro-well plate, raises the micro-well plate, transfers the micro-well plate to the area where it is required to be placed, and then places the micro-well plate in the appropriate position.

It is also possible to carry out homogeneous immunoassays merely by eliminating certain of the steps mentioned previously, such as, for example, moving microparticles from one micro-well to another micro-well.

EXAMPLE 2

Figure 17A:
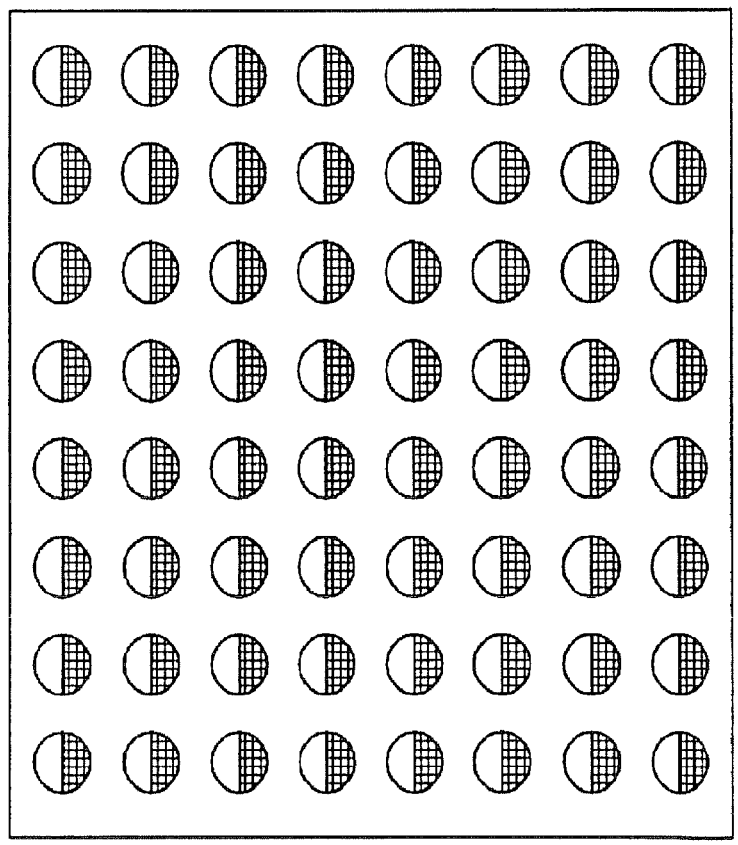
FIGS. 17A, 17B, and 17C are sequential top plan views of a single micro-well plate illustrating the kitting of a homogeneous immunoassay utilizing a single micro-well plate having 96 micro-wells.
Figure 17B:
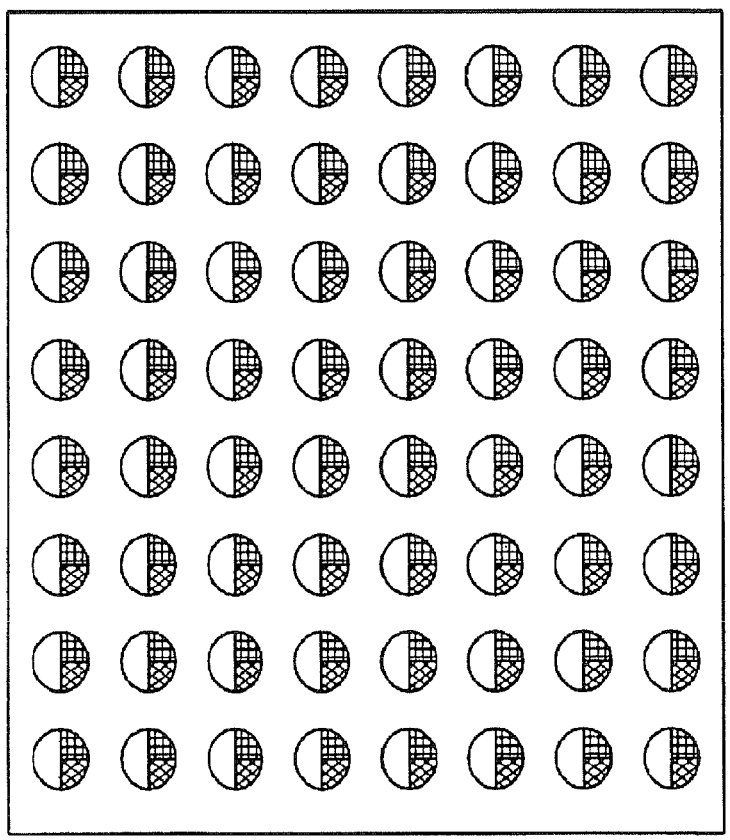
Figure 17C:
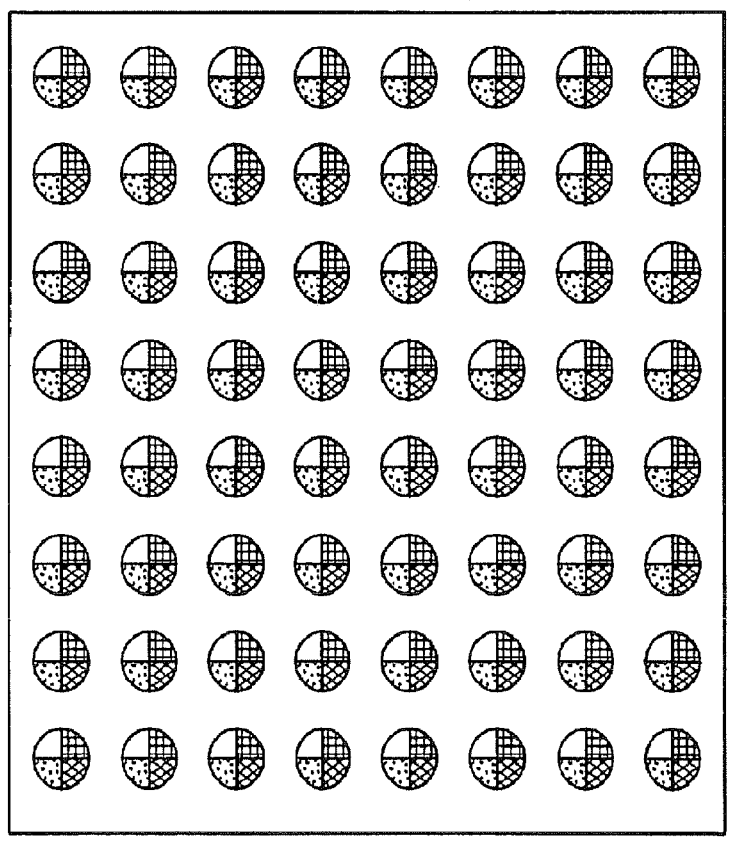

This example demonstrates kitting a micro-well plate for a homogeneous immunoassay. A homogeneous immunoassay is an immunoassay that does not require a separation step. An immunoassay for choline can be a homogeneous immunoassay, i.e., the immunoassay does not require magnetic separation and washing steps. Furthermore, only one micro-well is required for each immunoassay. FIGS. 17A, 17B, and 17C represent micro-well plates to be kitted for immunoassays. FIG. 17A shows the sample and a first reagent in each micro-well of the micro-well plate. FIG. 17B shows the sample, the first reagent, and the addition of the enzyme choline oxidase in each micro-well of a micro-well plate. FIG. 17C shows the sample, the first reagent, the enzyme choline oxidase, and the addition of the acridinium signal generator in each micro-well of the micro-well plate. After the additions of the reagents and a suitable period of incubation, the micro-well plate is inserted into a luminescence reader, and the results of the assay are determined. The homogeneous assay does not require magnetic particle processing to obtain an assay result.

EXAMPLE 3

This example illustrates a clinical chemistry assay using micro-well plates. FIGS. 19A, 19B, 19C, 19D, 19E, and 19F illustrate micro-well plates to be kitted for clinical chemistry assays. Referring now to FIGS. 19A, 19B, 19C, 19D, 19E, and 19F, the micro-well plate has eight (8) rows and twelve (12) columns. Columns 1-6 from the left involve assays for glucose (Glu), cholesterol (Chol), alanine transaminase or alanine aminotransferase (ALT), troponin (TP), Urea (Urea), and triglycerides (Trig), respectively. Columns 7-12 from the left involve the assays Glu, Chol, ALT, TP, Urea, and Trig, respectively. Rows 1-8 and columns 1-6 involve assays for eight (8) samples from different sources, i.e., sources John Doe, Jane Doe, Tom Doe, Mary Doe, Jim Doe, Beth Doe, Mike Doe, and Sue Doe. Rows 1-8 and columns 7-12 involve assays for another eight (8) samples from eight different sources, i.e., sources Carl Doe, Cindy Doe, Hank Doe, Julie Doe, Bob Doe, Pam Doe, Paul Doe, and Kim Doe. The absorbance reader travels from the right to the left in this example and the succeeding examples. TABLE 2 indicates various times required for various actions of the aspirating and dispensing procedures. FIGS. 19A, 19B, 19C, 19D, 19E, and 19F illustrate, in a sequential manner, the dispensing of samples and reagents for six assays for 16 patients.

Four different samples from four different patients (John Doe, Jane Doe, Tom Doe, Mary Doe) are aspirated into a four-channel XYZ pipette. The volume of each sample is sufficient for six assays. The samples are then dispensed into four rows of six columns to provide a total of 24 tests. These first 24 tests constitute the first set of four samples. The second set of four different samples from four different patients (Jim Doe, Beth Doe, Mike Doe, Sue Doe) are aspirated and dispensed by means of the aforementioned four-channel XYZ pipette into four rows of six columns to provide a total of 24 tests. The third set of four different samples from four different patients (Carl Doe, Cindy Doe, Hank Doe, and Julie Doe) are aspirated and dispensed by means of the aforementioned four-channel XYZ pipette into four rows of six columns to provide a total of 24 tests. The fourth set of four different samples from four different patients (Bob Doe, Pam Doe, Paul Doe, and Kim Doe) are aspirated and dispensed by means of the aforementioned four-channel XYZ pipette into four rows of six columns to provide a total of 24 tests. TABLE 2 indicates typical time required for each of the steps needed to kit the clinical chemistry assays.

TABLE 2

| Action | Time (sec) |
| --- | --- |
| Move to next tip | 3 |
| Get tip | 2 |
| Move to sample (40 inches) | 6 |
| Aspirate sample | 1 |
| Move and aspirate sample (3 times) | 18 |
| Move to micro-well plate (25 inches) | 5 |
| Move and dispense sample (6 times) | 22 |
| Move to tips (22 inches) | 5 |
| Drop tip | 2 |
| Total time | 64 |

The micro-well plate is rotated 90° to enable dispensing of reagents in the appropriate micro-wells of the micro-well plate. Volumes of four (4) R1 reagents are aspirated (at a volume of each R1 reagent sufficient for four assays) into a four-channel XYZ pipette. The R1 reagents are then dispensed into four rows of four columns. The patients who received this first batch of R1 reagents are John Doe, Jane Doe, Tom Doe, Mary Doe, and the reagents are for the assays for TP, ALT, Chol, and Glu. Immediately following these dispensings, the micro-well plate is positioned inside the absorbance reader. While the volumes of the same four (4) R1 reagents are being aspirated into a four-channel XYZ pipette (at a volume of each R1 reagent sufficient for four assays), the absorbance reader reads the micro-well plate. Immediately following this read, the micro-well plate is repositioned outside the absorbance reader, and the reagents are dispensed into four rows of four columns. The patients who received this second batch of R1 reagents are Jim Doe, Beth Doe, Mike Doe, Sue Doe, and the reagents are for the assays for TP, ALT, Chol, and Glu. Immediately following these dispensings, the micro-well plate is positioned inside the absorbance reader. While the volumes of four (4) R1 reagents are being aspirated into a four-channel XYZ pipette (at a volume of each R1 reagent sufficient for four assays), the absorbance reader reads the micro-well plate. Immediately following this read, the micro-well plate is repositioned outside the absorbance reader, and the reagents are dispensed into four rows of four columns. The patients who received this third batch of R1 reagents are John Doe, Jane Doe, Tom Doe, Mary Doe, and the reagents are for the assays for Trig and Urea. The patients who also received this third batch of R1 reagents are Carl Doe, Cindy Doe, Hank Doe, Julie Doe, and the reagents are for the assays for Chol, and Glu. Immediately following these dispensings, the micro-well plate is positioned inside the absorbance reader. While the volumes of the same four (4) R1 reagents are being aspirated into a four-channel XYZ pipette (at a volume of each R1 reagent sufficient for four assays), the absorbance reader reads the micro-well plate. Immediately following this read, the micro-well plate is repositioned outside the absorbance reader, and the reagents are dispensed into four rows of four columns. The patients who received this fourth batch of R1 reagents are Jim Doe, Beth Doe, Mike Doe, Sue Doe, and the reagents are for the assays for Trig and Urea. The patients who also received this fourth batch of R1 reagents are Bob Doe, Pam Doe, Paul Doe, and Kim Doe, and the reagents are for the assays for Chol, and Glu. Immediately following these dispensings, the micro-well plate is positioned inside the absorbance reader. While the volumes of four (4) R1 reagents are being aspirated into a four-channel XYZ pipette (at a volume of each R1 reagent sufficient for four assays), the absorbance reader reads the micro-well plate. Immediately following this read, the micro-well plate is repositioned outside the absorbance reader, and the reagents are dispensed into four rows of four columns. The patients who received this fifth batch of R1 reagents are Carl Doe, Cindy Doe, Hank Doe, Julie Doe, and the reagents are for the assays for Trig, Urea, TP, and ALT. Immediately following these dispensings, the micro-well plate is positioned inside the absorbance reader. While the volumes of the same four (4) R1 reagents are being aspirated into a four-channel XYZ pipette (at a volume of each R1 reagent sufficient for four assays), the absorbance reader reads the micro-well plate. Immediately following this read, the micro-well plate is repositioned outside the absorbance reader, and the reagents are dispensed into four rows of four columns. The patients who received this sixth batch of R1 reagents are Bob Doe, Pam Doe, Paul Doe, and Kim Doe, and the reagents are for the assays for Trig, Urea, TP, and ALT. Immediately following these dispensings, the micro-well plate is positioned inside the absorbance reader. TABLE 3 indicates typical time required for certain steps needed to kit clinical chemistry assays.

TABLE 3

| Action | Time (sec) |
| --- | --- |
| Move to next tip | 3 |
| Attach tip | 2 |
| Move to reagent (27 inches) | 5 |
| Aspirate reagent | 1 |
| Move and aspirate reagent (3 times) | 15 |
| Move to micro-well plate (22 inches) | 5 |
| Dispense and move reagent (4 times) | 14 |
| Move to reagent (22 inches) | 5 |
| Aspirate reagent | 1 |
| Move and aspirate reagent (3 times) | 15 |
| Move to micro-well plate (22 inches) | 5 |
| Dispense and move reagent (4 times) | 14 |
| Move to tips (22 inches) | 5 |
| Drop tip | 2 |
| Total time | 92 |

While the volumes of four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this first batch of complementary R2 reagents are John-Doe, Jane Doe, Tom Doe, Mary Doe, and the reagents are for the assays for TP, ALT, Chol, and Glu. Immediately following these dispensings, the micro-well plate is positioned inside the absorbance reader. While the volumes of the same four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this second batch of complementary R2 reagents are Jim Doe, Beth Doe, Mike Doe, Sue Doe, and the reagents are for the assays for TP, ALT, Chol, and Glu. Immediately following these dispensings, the micro-well plate is positioned inside the absorbance reader. While the volumes of four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this third batch of complementary R2 reagents are John Doe, Jane Doe, Tom Doe, Mary Doe, and the reagents are for the assays for Trig and Urea. The patients who also received this third batch of complementary R2 reagents are Carl Doe, Cindy Doe, Hank Doe, Julie Doe, and the reagents are for the assays for Chol, and Glu. Immediately following these dispensings, the micro-well plate is positioned inside the absorbance reader. While the volumes of the same four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this fourth batch of complementary R2 reagents are Jim Doe, Beth Doe, Mike Doe, Sue Doe, and the reagents are for the assays for Trig and Urea. The patients who also received this fourth batch of complementary R2 reagents are Bob Doe, Pam Doe, Paul Doe, and Kim Doe, and the reagents are for the assays for Chol, and Glu. Immediately following these dispensings, the micro-well plate is positioned inside the absorbance reader. While the volumes of four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this fifth batch of complementary R2 reagents are Carl Doe, Cindy Doe, Hank Doe, Julie Doe, and the reagents are for the assays for Trig, Urea, TP, and ALT. Immediately following these dispensings, the micro-well plate is positioned inside the absorbance reader. While the volumes of the same four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this sixth batch of complementary R2 reagents are Bob Doe, Pam Doe, Paul Doe, and Kim Doe, and the reagents are for the assays for Trig, Urea, TP, and ALT. Immediately following these dispensings, the micro-well plate is positioned inside the absorbance reader. Although no further dispensing of reagents are required, the micro-well plate remains in the absorbance reader, being read, for another 5 minutes (or whatever period is required by the protocols). Flexibility of protocols would allow for additional reagent additions, and/or modified reading windows.

To maximize the availability of the aspirating/dispensing device for other functions (such as, for example, kitting micro-well plates for immunoassays or dispensing samples into a micro-well plate for the next clinical chemistry assay), the assays for the clinical chemistry assays are arranged on the micro-well plate such that assays requiring both R1 and the complementary R2 reagent are dispensed before the assays that require R1 reagent only. In the same manner, if certain new clinical chemistry assays require R1 reagent, R2 reagent, and a new R3 reagent, then these assays would be arranged on the micro-well plate such that the reagents would be dispensed prior to the assays requiring both R1 and the complementary R2 reagent and before the assays that require R1 reagent only. TABLE 4 indicates typical time required for certain steps needed to kit clinical chemistry assays.

TABLE 4

| Action | Time (sec) |
| --- | --- |
| Move to next tip | 3 |
| Attach tip | 2 |
| Move to reagent (27 inches) | 5 |
| Aspirate reagent | 1 |
| Move and aspirate reagent (3 times) | 15 |
| Move to micro-well plate (22 inches) | 5 |
| Dispense and move reagent (4 times) | 14 |
| Move to reagent (22 inches) | 5 |
| Aspirate reagent | 1 |
| Move and aspirate reagent (3 times) | 15 |
| Move to micro-well plate (22 inches) | 5 |
| Dispense and move reagent (4 times) | 14 |
| Move to tips (22 inches) | 5 |
| Drop tip | 2 |
| Total time | 92 |

The reader moves from right to left. During aspirating and dispensing of the samples, the micro-well plate is oriented such that the 12-member rows are parallel to the direction that the pipette is moving. During aspirating and dispensing of the reagents, the micro-well plate is oriented such that the 8-member columns are parallel to the to the direction that the pipette is moving. The orientation of the micro-well plate can be altered by means of a turntable that is capable of rotating 90°.

EXAMPLE 4

In situations where more assays are requested, the samples of fewer patients can be tested. For example, if seven through twelve assays are requested, it is preferred that samples of eight patients be used. The following tables, TABLE 5, TABLE 6, and TABLE 7 tabulate aspirating and dispensing of samples, aspirating and dispensing of a first reagent, and aspirating and dispensing of a second reagent, respectively. FIGS. 20A, 20B, 20C, 20D, 20E, and 20F illustrate micro-well plates to be kitted for clinical chemistry assays. FIGS. 20A, 20B, 20C, 20D, 20E, and 20F illustrate, in a sequential manner, the dispensing of samples and reagents for twelve assays for eight patients.

Four different samples from four different patients (John Doe, Jane Doe, Tom Doe, Mary Doe) are aspirated into a four-channel XYZ pipette. The volume of each sample is sufficient for twelve (12) tests. The samples are then dispensed into four rows of twelve (12) columns to provide a total of 48 tests. These first 48 tests constitute the first set of four samples. The second set of four samples from four different patients (Jim Doe, Beth Doe, Mike Doe, Sally Doe) are aspirated into a four-channel XYZ pipette and dispensed into four rows of twelve (12) columns to provide a total of 48 tests. TABLE 5 indicates typical time required for certain steps needed to kit clinical chemistry assays.

TABLE 5

| Action | Time (sec) |
| --- | --- |
| Move to next tip | 3 |
| Get tip | 2 |
| Move to sample (40 inches) | 6 |
| Aspirate sample | 1 |
| Move and aspirate sample (3 times) | 18 |
| Move to micro-well plate (25 inches) | 5 |
| Move and dispense sample (12 times) | 46 |
| Move to tips (22 inches) | 5 |
| Drop tip | 2 |
| Total time | 88 |

The micro-well plate is rotated 90° to enable dispensing of reagents in the appropriate micro-wells of the micro-well plate. Volumes of four (4) R1 reagents are aspirated (at a volume of each R1 reagent sufficient for four assays) into a four-channel XYZ pipette. The R1 reagents are then dispensed into four rows of four columns. The patients who received this first batch of R1 reagents are John Doe, Jane Doe, Tom Doe, Mary Doe, and the reagents are for the assays for A1, A2, A3, and A4. Immediately following these dispensings, the micro-well plate is positioned inside the absorbance reader. While the volumes of the same four (4) R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns. The patients who received this second batch of R1 reagents are Jim Doe, Beth Doe, Mike Doe, Sally Doe, and the reagents are for the assays for A1, A2, A3, and A4. Immediately following these dispensings, the micro-well plate is positioned inside the absorbance reader. While the volumes of four (4) different R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns. The patients who received this third batch of R1 reagents are John Doe, Jane Doe, Tom Doe, Mary Doe, and the reagents are for the assays for A5, A6, A7, and A8. Immediately following these dispensings, the micro-well plate is positioned inside the absorbance reader. While the volumes of the same four (4) R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns. The patients who received this fourth batch of R1 reagents are Jim Doe, Beth Doe, Mike Doe, Sally Doe, and the reagents are for the assays for A5, A6, A7, and A8. Immediately following these dispensings, the micro-well plate is positioned inside the absorbance reader. While the volumes of four (4) different R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns. The patients who received this fifth batch of R1 reagents are John Doe, Jane Doe, Tom Doe, Mary Doe, and the reagents are for the assays for A9, A10, A11, and A12. Immediately following these dispensings, the micro-well plate is positioned inside the absorbance reader. While the volumes of the same four (4) R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns. The patients who received this sixth batch of R1 reagents are Jim Doe, Beth Doe, Mike Doe, Sally Doe, and the reagents are for the assays for A9, A10, A11, and A12. Immediately following these dispensings, the micro-well plate is positioned inside the absorbance reader. TABLE 6 indicates typical time required for certain steps needed to kit clinical chemistry assays.

TABLE 6

| Action | Time (sec) |
| --- | --- |
| Move to next tip | 3 |
| Attach tip | 2 |
| Move to reagent (27 inches) | 5 |
| Aspirate reagent | 1 |
| Move and aspirate reagent (3 times) | 15 |
| Move to micro-well plate (22 inches) | 5 |

TABLE 6-continued

| Action | Time (sec) |
| --- | --- |
| Dispense and mover reagent (4 times) | 14 |
| Move to reagent (22 inches) | 5 |
| Aspirate reagent | 1 |
| Move and aspirate reagent (3 times) | 15 |
| Move to micro-well plate (22 inches) | 5 |
| Dispense and move reagent (4 times) | 14 |
| Move to tips (22 inches) | 5 |
| Drop tip | 2 |
| Total time | 92 |

While the volumes of four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this first batch of complementary R2 reagents are John Doe, Jane Doe, Tom Doe, Mary Doe, and the reagents are for the assays for A1, A2, A3, and A4. Immediately following these dispensings, the micro-well plate is positioned inside the absorbance reader. While the volumes of the same four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this second batch of complementary R2 reagents are Jim Doe, Beth Doe, Mike Doe, Sally Doe, and the reagents are for the assays for A1, A2, A3, and A4. Immediately following these dispensings, the micro-well plate is positioned inside the absorbance reader. While the volumes of four (4) different complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this third batch of complementary R2 reagents are John Doe, Jane Doe, Tom Doe, Mary Doe, and the reagents are for the assays for A5, A6, A7, and A8. Immediately following these dispensings, the micro-well plate is positioned inside the absorbance reader. While the volumes of the same four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this fourth batch of complementary R2 reagents are Jim Doe, Beth Doe, Mike Doe, Sally Doe, and the reagents are for the assays for A5, A6, A7, and A8. Immediately following these dispensings, the micro-well plate is positioned inside the absorbance reader. While the volumes of four (4) different complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this fifth batch of complementary R2 reagents are John Doe, Jane Doe, Tom Doe, Mary Doe, and the reagents are for the assays for A9, A10, A11, and A12. Immediately following these dispensings, the micro-well plate is positioned inside the absorbance reader. While the volumes of the same four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this sixth batch of complementary R2 reagents are Jim Doe, Beth Doe, Mike Doe, Sally Doe, and the reagents are for the assays for A9, A10, A11, and A12. Immediately following these dispensings, the micro-well plate is positioned inside the absorbance reader. Although no further reagent dispensings are required, the micro-well plate remains in the absorbance reader, being read, for another 5 minutes (or whatever period is required by the protocols). Protocol flexibility would allow for additional reagent additions, and/or modified reading windows. TABLE 7 indicates typical time required for certain steps needed to kit clinical chemistry assays.

TABLE 7

| Action | Time (sec) |
|---|---|
| Move to next tip | 3 |
| Attach tip | 2 |
| Move to reagent (27 inches) | 5 |
| Aspirate reagent | 1 |
| Move and aspirate reagent (3 times) | 15 |
| Move to micro-well plate (22 inches) | 5 |
| Dispense and mover reagent (4 times) | 14 |
| Move to reagent (22 inches) | 5 |
| Aspirate reagent | 1 |
| Move and aspirate reagent (3 times) | 15 |
| Move to micro-well plate (22 inches) | 5 |
| Dispense and move reagent (4 times) | 14 |
| Move to tips (22 inches) | 5 |
| Drop tip | 2 |
| Total time | 92 |

EXAMPLE 5

As another example, if 13 through 16 assays are requested, it is preferred that samples of six patients be used. The following tables, TABLE 8, TABLE 9, and TABLE 10 tabulate aspirating and dispensing of samples, aspirating and dispensing of a first reagent, and aspirating and dispensing of a second reagent, respectively.

Four different samples from four different patients (John Doe, Jane Doe, Tom Doe, Mary Doe) are aspirated into a four-channel XYZ pipette. The volume of each sample is sufficient for sixteen (16) tests. The samples from the same four patients are then dispensed into four rows of four columns to provide a total of 64 tests. Two different samples from two different patients (Jim Doe and Beth Doe) are aspirated into a four-channel XYZ pipette and dispensed into four rows of eight columns to provide a total of 32 tests. TABLE 8 indicates typical time required for certain steps needed to kit clinical chemistry assays. FIGS. 21A, 21B, 21C, 21D, 21E, and 21F illustrate micro-well plates to be kilted for clinical chemistry assays. FIGS. 21A, 21B, 21C, 21D, 21E, and 21F illustrate, in a sequential manner, the dispensing of samples and reagents for 16 assays for six patients.

TABLE 8

| Action | Time (sec) |
|---|---|
| Move to next tip | 3 |
| Get tip | 2 |
| Move to sample (40 inches) | 6 |
| Aspirate sample | 1 |
| Move and aspirate sample (3 times) | 18 |
| Move to micro-well plate (25 inches) | 5 |
| Move and dispense sample (12 times) | 46 |
| Reposition to micro-well plate | 3 |
| Move and dispense sample (4 times) | 14 |
| Move to tips (22 inches) | 5 |
| Drop tip | 2 |
| Total time | 105 |
| Move to next tip | 3 |
| Get tip | 2 |
| Move to sample (40 inches) | 6 |
| Aspirate sample | 1 |
| Move and aspirate sample (1 time) | 6 |
| Move to micro-well plate (25 inches) | 5 |
| Move and dispense sample (8 times) | 30 |
| Reposition to micro-well plate | 3 |
| Move and dispense sample (8 times) | 30 |
| Move to tips (22 inches) | 5 |
| Drop tip | 2 |
| Total time | 93 |

The micro-well plate is rotated 90° to enable dispensing of reagents in the appropriate micro-wells of the micro-well plate. Volumes of four (4) R1 reagents are aspirated (at a volume of each R1 reagent sufficient for four assays) into a four-channel XYZ pipette. The R1 reagents are then dispensed into four rows of four columns. The patients who received this first batch of R1 reagents are John Doe, Jane Doe, Tom Doe, Mary Doe, and the reagents are for the assays for A1, A2, A3, and A4. Immediately following these dispensings, the micro-well plate is positioned inside the absorbance reader. While the volumes of the same four (4) R1 reagents are being aspirated into a four-channel XYZ pipette (at a volume of each R1 reagent sufficient for two assays), the micro-well plate is read by the absorbance reader. Immediately following the reading, the micro-well plate is repositioned outside the absorbance reader, and the reagents are dispensed into two rows of four columns. The patients who received this second batch of R1 reagents are Jim Doe, and Beth Doe, and the reagents are for the assays for A1, A2, A3, and A4. Immediately following these dispensings, the micro-well plate is positioned inside the absorbance reader. While the volumes of four (4) different R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns. The patients who received this third batch of R1 reagents are John Doe, Jane Doe, Tom Doe, Mary Doe, and the reagents are for the assays for A5, A6, A7, and A8. Immediately following these dispensings, the micro-well plate is positioned inside the absorbance reader. While the volumes of the same four (4) R1 reagents are being aspirated into a four-channel XYZ pipette (at a volume of each R1 reagent sufficient for two assays), the micro-well plate is read by the absorbance reader. Immediately following the reading, the micro-well plate is repositioned outside the absorbance reader, and the reagents are dispensed into two rows of four columns. The patients who received this fourth batch of R1 reagents are Jim Doe, and Beth Doe, and the reagents are for the assays for A5, A6, A7, and A8. Immediately following these dispensings, the micro-well plate is positioned inside the absorbance reader. While the volumes of four (4) different R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns. The patients who received this fifth batch of R1 reagents are John Doe, Jane Doe, Tom Doe, Mary Doe, and the reagents are for the assays for A9, A10, A11, and A12. Immediately following these dispensings, the micro-well plate is positioned inside the absorbance reader. While the volumes of the same four (4) R1 reagents are being aspirated into a four-channel XYZ pipette (at a volume of each R1 reagent sufficient for two assays), the micro-well plate is read by the absorbance reader. Immediately following the reading, the micro-well plate is repositioned outside the absorbance reader, and the reagents are dispensed into two rows of four columns. The patients who received this sixth batch of R1 reagents are Jim Doe, and Beth Doe, and the reagents are for the assays for A9, A10, A11, and A12. Immediately following these dispensings, the micro-well plate is positioned inside the absorbance reader. While the volumes of four (4) different R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns. The patients who received this seventh batch of R1 reagents are John Doe, Jane Doe, Tom Doe, Mary Doe, and the reagents are for the assays for A13, A14, A15, and A16. Immediately following these dispensings, the micro-well plate is positioned inside the absorbance reader. While the volumes of the same four (4) R1 reagents are being aspirated into a four-channel XYZ pipette (at a volume of each R1 reagent sufficient for two assays), the micro-well plate is read by the absorbance reader. Immediately following the reading, the micro-well plate is repositioned outside the absorbance reader, and the reagents are dispensed into two rows of four columns. The patients who received this eighth batch of R1 reagents are Jim Doe, and Beth Doe, and the reagents are for the assays for A13, A14, A15, and A16. Immediately following these dispensings, the micro-well plate is positioned inside the absorbance reader. TABLE 9 indicates typical time required for certain steps needed to kit clinical chemistry assays.

TABLE 9

| Action | Time (sec) |
|---|---|
| Move to next tip | 3 |
| Attach tip | 2 |
| Move to reagent (27 inches) | 5 |
| Aspirate reagent | 1 |
| Move and aspirate reagent (3 times) | 15 |
| Move to micro-well plate (22 inches) | 5 |
| Dispense and mover reagent (4 times) | 14 |
| Move to reagent (22 inches) | 5 |
| Aspirate reagent | 1 |
| Move and aspirate reagent (3 times) | 15 |
| Move to micro-well plate (22 inches) | 5 |
| Dispense and move reagent (2 times) | 6 |
| Move to tips (22 inches) | 5 |
| Drop tip | 2 |
| Total time | 84 |

While the volumes of four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this first batch of complementary R2 reagents are John Doe, Jane Doe, Tom Doe, Mary Doe, and the reagents are for the assays for A1, A2, A3, and A4. Immediately following these dispensings, the micro-well plate is positioned inside the absorbance reader. While the volumes of the same four (4) complementary R2 reagents are being aspirated into a four-channel XYZ pipette (at a volume of each complementary R2 reagent sufficient for two assays), the micro-well plate is read by the absorbance reader. Immediately following the reading, the micro-well plate is repositioned outside the absorbance reader, and the reagents are dispensed into two rows of four columns. The patients who received this second batch of complementary R2 reagents are Jim Doe, and Beth Doe, and the reagents are for the assays for A1, A2, A3, and A4. Immediately following these dispensings, the micro-well plate is positioned inside the absorbance reader. While the volumes of four (4) different complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this third batch of complementary R2 reagents are John Doe, Jane Doe, Tom Doe, Mary Doe, and the reagenis are for the assays for A5, A6, A7, and A8. Immediately following these dispensings, the micro-well plate is positioned inside the absorbance reader. While the volumes of the same four (4) complementary R2 reagents are being aspirated into a four-channel XYZ pipette (at a volume of each complementary R2 reagent sufficient for two assays), the micro-well plate is read by the absorbance reader. Immediately following the reading, the micro-well plate is repositioned outside the absorbance reader, and the reagents are dispensed into two rows of four columns. The patients who received this fourth batch of complementary R2 reagents are Jim Doe, and Beth Doe, and the reagents are for the assays for A5, A6, A7, and A8. Immediately following these dispensings, the micro-well plate is positioned inside the absorbance reader. While the volumes of four (4) different complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this fifth batch of complementary R2 reagents are John Doe, Jane Doe, Tom Doe, Mary Doe, and the reagents are for the assays for A9, A10, A11, and A12. Immediately following these dispensings, the micro-well plate is positioned inside the absorbance reader. While the volumes of the same four (4) complementary R2 reagents are being aspirated into a four-channel XYZ pipette (at a volume of each complementary R2 reagent sufficient for two assays), the micro-well plate is read by the absorbance reader. Immediately following the reading, the micro-well plate is repositioned outside the absorbance reader, and the reagents are dispensed into two rows of four columns. The patients who received this sixth batch of complementary R2 reagents are Jim Doe, and Beth Doe, and the reagents are for the assays for A9, A10, A11, and A12. Immediately following these dispensings, the micro-well plate is positioned inside the absorbance reader. While the volumes of four (4) different complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns. The patients who received this seventh batch of complementary R2 reagents are John Doe, Jane Doe, Tom Doe, Mary Doe, and the reagents are for the assays for A13, A14, A15, and A16. Immediately following these dispensings, the micro-well plate is positioned inside the absorbance reader. While the volumes of the same four (4) complementary R2 reagents are being aspirated into a four-channel XYZ pipette (at a volume of each complementary R2 reagent sufficient for two assays), the micro-well plate is read by the absorbance reader. Immediately following the reading, the micro-well plate is repositioned outside the absorbance reader, and the reagents are dispensed into two rows of four columns. The patients who received this eighth batch of complementary R2 reagents are Jim Doe, and Beth Doe, and the reagents are for the assays for A13, A14, A15, and A16. Immediately following these dispensings, the micro-well plate is positioned inside the absorbance reader. Although no further reagent dispensings are required, the micro-well plate remains in the absorbance reader, being read, for another 5 minutes (or whatever period is required by the protocols). Protocol flexibility would allow for additional reagent additions, and/or modified reading windows. TABLE 10 indicates typical time required for certain steps needed to kit clinical chemistry assays.

TABLE 10

| Action | Time (sec) |
|---|---|
| Move to next tip | 3 |
| Attach tip | 2 |
| Move to reagent (27 inches) | 5 |
| Aspirate reagent | 1 |
| Move and aspirate reagent (3 times) | 15 |
| Move to micro-well plate (22 inches) | 5 |
| Dispense and mover reagent (4 times) | 14 |
| Move to reagent (22 inches) | 5 |
| Aspirate reagent | 1 |
| Move and aspirate reagent (3 times) | 15 |
| Move to micro-well plate (22 inches) | 5 |
| Dispense and move reagent (2 times) | 6 |
| Move to tips (22 inches) | 5 |
| Drop tip | 2 |
| Total time | 84 |

EXAMPLE 6

If 17-24 assays are requested, it is preferred that samples of four patients be used. The following tables, TABLE 11, TABLE 12, and TABLE 13 tabulate aspirating and dispensing of samples, aspirating and dispensing of a first reagent, and aspirating and dispensing of a second reagent, respectively. FIGS. 22A, 22B, 22C, 22D, 22E, and 22F represent micro-well plates to be kitted for clinical chemistry assays. FIGS. 22A, 22B, 22C, 22D, 22E, and 22F illustrate, in a sequential manner, the dispensing of samples and reagents for 24 assays for four patients Four different samples from four patients (John Doe, Jane Doe, Tom Doe, Mary Doe) are aspirated into a four-channel XYZ pipette. The volume of each sample is sufficient for six tests. The samples are then dispensed into four rows of six columns to provide a total of 24 tests. These first 24 tests constitute the first set of four samples. The second set of four samples from the same four patients (John Doe, Jane Doe, Tom Doe, Mary Doe) are aspirated into a four-channel XYZ pipette and dispensed into four rows of six columns to provide a total of 24 tests. The third set of four samples from the same four patients (John Doe, Jane Doe, Tom Doe, Mary Doe) are aspirated into a four-channel XYZ pipette and dispensed into four rows of six columns to provide a total of 24 tests. The fourth set of four samples from the same four patients (John Doe, Jane Doe, Tom Doe, Mary Doe) are aspirated into a four-channel XYZ pipette and dispensed into four rows of six columns to provide a total of 24 tests. TABLE II indicates typical time required for certain steps needed to kit clinical chemistry assays.

TABLE 11

| Action | Time (sec) |
|---|---|
| Move to next tip | 3 |
| Get tip | 2 |
| Move to sample (40 inches) | 6 |
| Aspirate sample | 1 |
| Move and aspirate sample (3 times) | 18 |
| Move to micro-well plate (25 inches) | 5 |
| Move and dispense sample (12 times) | 46 |
| Reposition to (?) micro-well plate | 3 |
| Move and dispense sample (12 times) | 46 |
| Move to tips (22 inches) | 5 |
| Drop tip | 2 |
| Total time | 137 |

The micro-well plate is rotated 90° to enable dispensing of reagents in the appropriate micro-wells of the micro-well plate. Volumes of four (4) R1 reagents are aspirated (at a volume of each R1 reagent sufficient for four assays) into a four-channel XYZ pipette. The R1 reagents are then dispensed into four rows of four columns, but every other row so that it corresponds to the correct test. The patients who received this first batch of R1 reagents are John Doe, Jane Doe, Tom Doe, Mary Doe, and the reagents are for the assays for A1, A2, A3, and A4. Immediately following these dispensings, the micro-well plate is positioned inside the absorbance reader. While the volumes of four (4) different R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns, but every other row so that it corresponds to the correct test. The patients who received this second batch of R1 reagents are John Doe, Jane Doe, Tom Doe, Mary Doe, and the reagents are for the assays for A5, A6, A7, and A8. Immediately following these dispensings, the micro-well plate is positioned inside the absorbance reader. While the volumes of four (4) different R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns, but every other row so that it corresponds to the correct test. The patients who received this third batch of R1 reagents are John Doe, Jane Doe, Tom Doe, Mary Doe, and the reagents are for the assays for A9, A10, A11, and A12. Immediately following these dispensings, the micro-well plate is positioned inside the absorbance reader. While the volumes of four (4) different R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns, but every other row so that it corresponds to the correct test. The patients who received this fourth batch of R1 reagents are John Doe, Jane Doe, Tom Doe, Mary Doe, and the reagents are for the assays for A13, A14, A15, and A16. Immediately following these dispensings, the micro-well plate is positioned inside the absorbance reader. While the volumes of four (4) different R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns, but every other row so that it corresponds to the correct test. The patients who received this fifth batch of R1 reagents are John Doe, Jane Doe, Tom Doe, Mary Doe, and the reagents are for the assays for A17, A18, A19, and A20. Immediately following these dispensings, the micro-well plate is positioned inside the absorbance reader. While the volumes of four (4) different R1 reagents are being aspirated into a four-channel XYZ pipette (at a volume of each R1 reagent sufficient for four assays), the micro-well plate is read by the absorbance reader. Immediately following the reading, the micro-well plate is repositioned outside the absorbance reader, and the reagents are dispensed into four rows of four columns, but every other row so that it corresponds to the correct test. The patients who received this sixth batch of R1 reagents are John Doe, Jane Doe, Tom Doe, Mary Doe, and the reagents are for the assays for A21, A22, A23, and A24. Immediately following these dispensings, the micro-well plate is positioned inside the absorbance reader. TABLE 12 indicates typical time required for certain steps needed to kit clinical chemistry assays.

TABLE 12

| Action | Time (sec) |
|---|---|
| Move to next tip | 3 |
| Attach tip | 2 |
| Move to reagent (27 inches) | 5 |
| Aspirate reagent | 1 |
| Move and aspirate reagent (3 times) | 15 |
| Move to micro-well plate (22 inches) | 5 |
| Dispense and mover reagent (4 times) | 14 |
| Move to reagent (22 inches) | 5 |
| Drop tip | 2 |
| Total time | 52 |

While the volumes of four (4) complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns, but every other row so that it corresponds to the correct test. The patients who received this first batch of complementary R2 reagents are John Doe, Jane Doe, Tom Doe, Mary Doe, and the reagents are for the assays for A1, A2, A3, and A4. Immediately following these dispensings, the micro-well plate is positioned inside the absorbance reader. While the volumes of four (4) different complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns, but every other row so that it corresponds to the correct test. The patients who received this second batch of complementary R2 reagents are John Doe, Jane Doe, Tom Doe, Mary Doe, and the reagents are for the assays for A5, A6, A7, and A8. Immediately following these dispensings, the micro-well plate is positioned inside the absorbance reader. While the volumes of four (4) different complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns, but every other row so that it corresponds to the correct test. The patients who received this third batch of complementary R2 reagents are John Doe, Jane Doe, Toni Doe, Mary Doe, and the reagents are for the assays for A9, A10, A11, and A12. Immediately following these dispensings, the micro-well plate is positioned inside the absorbance reader. While the volumes of four (4) different complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns, but every other row so that it corresponds to the correct test. The patients who received this fourth batch of complementary R2 reagents are John Doe, Jane Doe, Tom Doe, Mary Doe, and the reagents are for the assays for A13, A14, A15, and A16. Immediately following these dispensings, the micro-well plate is positioned inside the absorbance reader. While the volumes of four (4) different complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns, but every other row so that it corresponds to the correct test. The patients who received this fifth batch of complementary R2 reagents are John Doe, Jane Doe, Tom Doe, Mary Doe, and the reagents are for the assays for A17, A18, A19, and A20. Immediately following these dispensings, the micro-well plate is positioned inside the absorbance reader. While the volumes of four (4) different complementary R2 reagents are being aspirated into a four-channel XYZ pipette (at a volume of each complementary R2 reagent sufficient for four assays), the micro-well plate is read by the absorbance reader. Immediately following the reading, the micro-well plate is repositioned outside the absorbance reader, and the reagents are dispensed into four rows of four columns, but every other row so that it corresponds to the correct test. The patients who received this sixth batch of complementary R2 reagents are John Doe, Jane Doe, Tom Doe, Mary Doe, and the reagents are for the assays for A21, A22, A23, and A24. Immediately following these dispensings, the micro-well plate is positioned inside the absorbance reader. Although no further reagent dispensings are required, the micro-well plate remains in the absorbance reader, being read, for another 5 minutes (or whatever period is required by the protocols). Protocol flexibility would allow for additional reagent additions, and/or modified reading windows. TABLE 13 indicates typical time required for certain steps needed to kit clinical chemistry assays.

TABLE 13

| Action | Time (sec) |
|---|---|
| Move to next tip | 3 |
| Attach tip | 2 |
| Move to reagent (27 inches) | 5 |
| Aspirate reagent | 1 |
| Move and aspirate reagent (3 times) | 15 |
| Move to micro-well plate (22 inches) | 5 |
| Dispense and mover reagent (4 times) | 14 |
| Move to tips (22 inches) | 5 |
| Drop tip | 2 |
| Total time | 52 |

EXAMPLE 7

This example illustrates the kitting of multi-well plates for use in a KingFisher™ Flex magnetic particle processor for extraction of nucleic acids. A substantially similar embodiment of the laboratory automation system as was described with respect to FIG. 7 can be used for the kitting of multi-well plates, magnetic particle processing, and analysis of nucleic acids.

The KingFisher™ Flex magnetic particle processor can provide rapid and reproducible purification of high-quality DNA, RNA, proteins, and cells from various starting materials, such as, for example, blood, cell cultures, tissue lysates, soil, and faeces. Like the KingFisher™ magnetic particle processors described previously, the KingFisher™ Flex magnetic particle processor uses magnetic rods that move particle through the various purification phases, i.e., binding, missing, washing, elution. The KingFisher™ Flex magnetic particle processor uses a 24-rod magnet head and 24-well deep well plate. The volume of sample can be as high as 5 mL. For higher throughput needs, 96 samples can be processed in different working volumes (20-1000 µL) using 96-rod magnet head and appropriate 96-well plates. Additional details relating to the KingFisher™ Flex magnetic particle processor are accessible by means of the Hypertext Transfer Protocol on the World Wide Web at the website thermo.com/com/cda/product/detail/1,10136240,00.html, incorporated herein by reference.

FIGS. 25A, 25B, 25C, 25D, 25E, and 25F represent multi-well plates to be kitted for extraction of a nucleic acid from a sample. Referring now to FIGS. 25A, 25B, 25C, 25D, 25E, and 25F, each deep well plate for extraction of RNA (1.0 mL HIV) encompasses an entire step of the protocol for the magnetic particle processor. Thus, one complete deep well multi-well plate is used for the introduction of samples along with microparticles and appropriate buffer, two complete deep well multi-well plates are used for diluted lysis buffer, two complete deep well multi-well plates are used for water, and one complete deep well multi-well plate is used for phosphate buffer. A total of six deep well multi-well plates are used for a given magnetic separation process for the aforementioned antigen. After the samples, the magnetic microparticles, and the buffers are introduced to the deep well multi-well plates and the appropriate incubation procedures have been carried out, the deep well multi-well plates are transferred to a KingFisher™ Flex magnetic particle processor.

The sample is typically serum. Serum is also typically used in both immunoassay analyzers and clinical chemistry analyzers. Other samples, such as, for example, sputum or tissue scrapings, will be eluted in a volume of liquid that would be equivalent to a volume of serum. A representative example of lysis buffer suitable for use herein (RNA) comprises a mixture of 4.66M guanidine isothiocyanate, 2-amino-2-(hydroxymethyl)-1,3-propanediol (Trizma®, pH 8.0), and polyoxyethylenesorbitan monolaurate (Tween® 20, 10%). A representative example of diluted lysis buffer suitable for use herein comprises 2M guanidine isothiocyanate, polyoxyethylenesorbitan monolaurate (Tween® 20, 5%), and 50 mM potassium acetate (pH 6.0). A representative example of a phosphate buffer suitable for use herein comprises 20 mM potassium phosphate (pH 8.5). Magnetic microparticles are typically particles comprising iron oxide.

TABLE 14 lists the materials, amounts, time and temperature conditions for each deep well of the multi-well plate, and an approximate time for kitting. The table also lists the figure that illustrates the deep well multi-well plate.

TABLE 14

| FIG. | Material in each well | Quantity of material (µL) | Temperature (° C.) | Time (minutes) | Time for kitting (minutes) |
|---|---|---|---|---|---|
| 25A | Magnetic microparticles | 100 | 50 | 20 | 14.5 |
| 25A | Lysis buffer | 2400 | 50 | 20 | 14.5 |
| 25A | Sample | 1000 | 50 | 20 | 14.5 |
| 25B | Diluted lysis buffer | 700 | 25 | | 1 |
| 25C | Diluted lysis buffer | 700 | 25 | | 1 |
| 25D | Water | 700 | 25 | | 1 |
| 25E | Water | 700 | 25 | | 1 |
| 25F | Phosphate buffer* | 25 | 75 | 20 | 2 |

*Water (63 µL) is added to each well of the multi-well plate prior to the step of transferring the extracted nucleic acid to the wells of a PCR plate.

The lysis buffer disrupts cell membranes, thereby exposing nucleic acid and enabling the nucleic acid to attach to magnetic microparticles. The material in the multi-well plates shown in FIGS. 25B, 25C, 25D, and 25E, i.e., diluted lysis buffer, water, operate to wash away the lysis buffer, because the lysis buffer interferes with the polymerase chain reaction for amplifying nucleic acids. The phosphate buffer elutes, i.e., releases the nucleic acid from the magnetic microparticles.

Figure 25D:
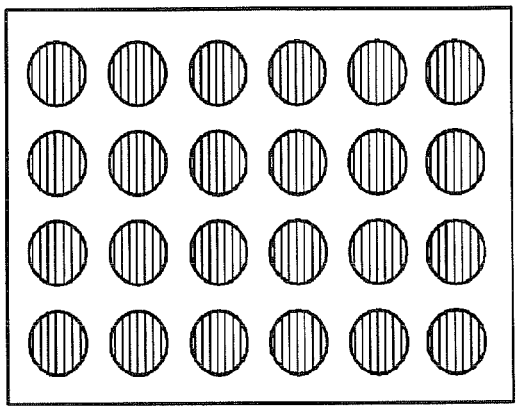
Figure 25E:
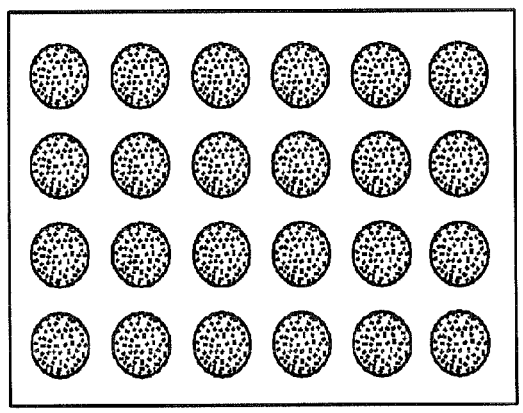
Figure 25F:
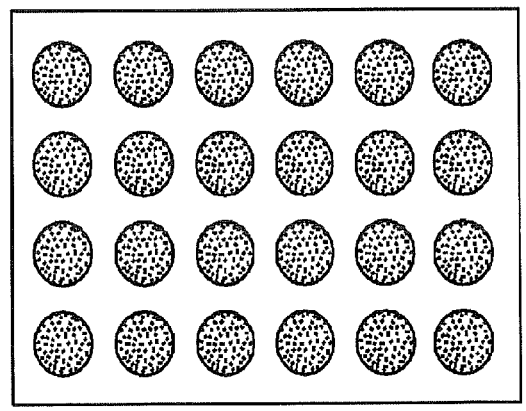

A high-speed reagent dispenser can be employed to kit the multi-well plates shown in FIGS. 25B, 25C, 25D, 25E, and 25F at the same time that the multi-well plate shown in FIG. 25A is being kitted by a different dispensing device, in which case a saving of 5.5 minutes of kitting time can be realized.

After the nucleic acid is released from the magnetic microparticles, the nucleic acid can be aspirated from the deep wells of the multi-well plate and transferred to the wells of a 96-well PCR plate. This transfer step is referred to herein as master mixing and activating. An example of the transfer step involves the transfer of samples from four magnetic particle processing operations from one or more KingFisher™ Flex magnetic particle processors to the 96-well PCR plate. After the samples that have been processed by the magnetic particle processor have been introduced to the 96-well PCR plate, the appropriate reagents are introduced to each well of the 96-well PCR plate, the 96-well PCR plate is sealed, and the sealed 96-well PCR plate is transferred to the thermal cycler for further processing.

The amplification of the nucleic acid can be carried out in a thermal cycler, also known as a thermocycler, PCR machine, or DNA amplifier. This device can be used to amplify segments of DNA via the polymerase chain reaction (PCR) process. The device has thermal block with holes where tubes holding the PCR reaction mixtures can be inserted. The cycler then raises and lowers the temperature of the block in discrete, pre-programmed steps. Thermal cyclers are described, for example, in articles, such as, for example, Thermal cycler, accessible by means of the Hypertext Transfer Protocol on the World Wide Web at the website en.wikipedia.org/wiki/Thermal_cycler, incorporated herein by reference. Additional information relating to the processes carried out by thermal cyclers can be found, for example, in articles, such as, for example, Polymerase chain reaction, accessible by means of the Hypertext Transfer Protocol on the World Wide Web at the website en.wikipedia.org/wiki/Polymerasae_chain_reaction, incorporated herein by reference. Representative examples of thermal cyclers suitable for use herein include ABI7500 Thermocycler/Reader, Bio-Rad® i-Cycler®, Stratagene MX4000™.

Kitting of the multi-well plates can be carried out at the aspirating/dispensing locations 124a and 124b of FIG. 7, magnetic particle processing can be carried out in the areas 140a of FIG. 7, transfer of the nucleic acid from the multi-well plate to the PCR plate can be carried out near the area 124b of FIG. 7, and the PCR process can be carried out in an area of FIG. 7 where thermal cyclers can be positioned, typically within the analysis section 60 of the laboratory automation system.

The estimated processing time for the KingFisher™ Flex magnetic particle processor is 44 minutes. The estimated time for thermal cycling and reading is three hours. The estimated time for master mixing and activating is 32 minutes. The estimated time for achieving the first result is approximately four hours and 46 minutes. The approximate throughput is 94 tests per hour.

EXAMPLE 8

This example illustrates the kitting of multi-well plates for use in a KingFisher™ Flex magnetic particle processor for extraction of nucleic acids. A substantially similar embodiment of the laboratory automation system as was described with respect to FIG. 7 can be used for the kitting of multi-well plates, magnetic particle processing, and analysis of nucleic acids.

FIGS. 26A, 26B, 26C, 26D, 26E, 26F, and 26G illustrate multi-well plates to be kitted for extraction of a nucleic acid from a sample. Referring now to FIGS. 26A, 26B, 26C, 26D, 26E, 26F, and 26G, each deep well plate for extraction of DNA (0.5 mL HBV) encompasses an entire step of the protocol for the magnetic particle processor. Thus, one complete deep well multi-well plate is used for the introduction of samples along with microparticles and appropriate buffers, two complete deep well multi-well plates are used for lysis buffer, three complete deep well multi-well plates are used for ethanol buffer, and one complete deep well multi-well plate is used for water. A total of seven deep well multi-well plates are used for a given magnetic separation process for the aforementioned antigen. After the samples, the magnetic microparticles, and the buffers are introduced to the deep well multi-well plates and the appropriate incubation procedures have been carried out, the deep well multi-well plates are transferred to a KingFisher™ Flex magnetic particle processor. The KingFisher™ Flex magnetic particle processor can be used to carry out the magnetic particle processing in substantially the same manner that was used in EXAMPLE 7.

The sample is typically serum. Serum is also typically used in both immunoassay analyzers and clinical chemistry analyzers. Other samples, such as, for example, sputum or tissue scrapings, will be eluted in a volume of liquid that would be equivalent to a volume of serum. A representative example of lysis buffer suitable for use herein (DNA) comprises a mixture of 2M guanidine isothiocyanate, polyoxyethylenesorbitan monolaurate (Tween® 20, 5%), and 50 mM potassium acetate (pH 6.0). A representative example of a phosphate buffer suitable for use herein comprises 20 mM potassium phosphate (pH 8.5). A representative example of ethanol buffer suitable for use herein (DNA) comprises 70% ethanol. A representative example of PK reagent suitable for use herein (DNA) comprises proteinase K buffer.

TABLE 15 lists the materials, amounts, time and temperature conditions for each deep well plate, and an approximate range of time for kitting. The table also lists the figure that illustrates the deep well plate.

TABLE 15

| FIG. | Material in each well | Quantity of material | Temperature (° C.) | Time (minutes) | Range of time for kitting (minutes) |
|---|---|---|---|---|---|
| First incubation* | | | | | |
| 26A | Lysis buffer | 150 μL | 58 | 15 | 31.5 |
| 26A | PK buffer | 400 μL | 58 | 15 | 31.5 |
| 26A | Sample | 500 μL | 58 | 15 | 31.5 |
| Second incubation* | | | | | |
| 26A | Lysis buffer | 1950 μL | 58 | 15 | 31.5 |
| 26A | Magnetic microparticles | 60 μL | 58 | 15 | 31.5 |
| 26B | Lysis buffer | 700 μL | 58 | 5 | 1 |
| 26C | Lysis buffer | 700 μL | 25 | | 1 |
| 26D | Ethanol buffer | 750 μL | 25 | | 1 |
| 26E | Ethanol buffer | 500 μL | 25 | | 1 |
| 26F | Ethanol buffer | 500 μL | 25 | | 1 |
| 26G | Water | 110 μL | 80 | 8** | 1 |

*Lysis buffer, PK buffer, and sample were incubated at 58° C. for 15 minutes, after which time, additional lysis buffer and the magnetic microparticles were added, and the combined mixture was incubated at 58° C. for 15 minutes.
Cool down for three minutes The lysis buffer disrupts cell membranes, thereby exposing nucleic acid and enabling the nucleic acid to attach to magnetic microparticles. The material in the multi-well plates shown in FIGS. 26B, 26C, 26D, 26E, and 26F, i.e., diluted lysis buffer, ethanol buffer, operate to wash away the lysis buffer, because the lysis buffer interferes with the polymerase chain reaction for amplifying nucleic acids. FIG. 26G shows a multi-well plate in which the nucleic acid is eluted in water for 15 minutes. The materials in the wells in the multi-well plate in FIG. 26G** are then cooled down for three minutes.

A high-speed reagent dispenser can be employed to kit the multi-well plates shown in FIGS. 26B, 26C, 26D, 26E, 26F, and 26G at the same time that the multi-well plate shown in FIG. 26A is being kitted by a different dispensing device, in which case a saving of 21 minutes of kitting time can be realized.

After the nucleic acid is released from the magnetic microparticles, the nucleic acid can be aspirated from the deep wells of the multi-well plate and transferred to the wells of a 96-well PCR plate. This transfer step is referred to herein as master mixing and activating. An example of the transfer step involves the transfer of samples from four magnetic particle processing operations from one or more KingFisher™ Flex magnetic particle processors to the 96-well PCR plate. After the samples that have been processed by the magnetic particle processor have been introduced to the 96-well PCR plate, the appropriate reagents are introduced to each well of the 96-well PCR plate, the 96-well PCR plate is sealed, and the sealed 96-well PCR plate is transferred to the thermal cycler for further processing.

The amplification of nucleic acid can be carried out in a thermal cycler, also known as a thermocycler, PCR machine, or DNA amplifier. This device can be used to amplify segments of DNA via the polymerase chain reaction (PCR) process. The device has thermal block with holes where tubes holding the PCR reaction mixtures can be inserted. The cycler then raises and lowers the temperature of the block in discrete, pre-programmed steps. Thermal cyclers are described, for example, in articles, such as, for example, Thermal cycler, accessible by means of the Hypertext Transfer Protocol on the World Wide Web at the website en.wikipedia.org/wiki/Thermal_cycler, incorporated herein by reference. Additional information relating to the processes carried out by thermal cyclers can be found, for example, in articles, such as, for example, Polymerase chain reaction, accessible by means of the Hypertext Transfer Protocol on the World Wide Web at the website en.wikipedia.org/wiki/Polymerasae_chain_reaction, incorporated herein by reference. Representative examples of thermal cyclers suitable for use herein include ABI7500 Thermocycler/Reader, Bio-Rad® i-Cycler®, Stratagene MX4000™.

Kitting of the multi-well plates can be carried out at the aspirating/dispensing locations 124a and 124b of FIG. 7, magnetic particle processing can be carried out in the areas 140a of FIG. 7, transfer of the nucleic acid from the multi-well plate to the PCR plate can be carried out near the area 124b of FIG. 7, and the PCR process can be carried out in an area of FIG. 7 where thermal cyclers can be positioned, typically within the analysis section 60 of the laboratory automation system.

The estimated processing time for the KingFisher™ Flex magnetic particle processor is 52 minutes. The estimated time for thermal cycling and reading is two hours and 15 minutes. The estimated time for master mixing and activating is 32 minutes. The estimated time for achieving the first result is approximately four hours and 25 minutes. The approximate throughput is 89 tests per hour.

The operations of the laboratory automation system 10 can be controlled by a personal computer, using commercially available interfaces. These interfaces are identified in FIG. 24. The graphical user interface can use features and controls that are common to modern personal computer graphical user interfaces. For example, drop down menus and tree-views can be used for multiple choices. Radio buttons, checkboxes, and slider controls can provide selection options that are intuitive to the operator. Splash screens, progress bars, and highlighted controls can provide status reports that are intuitive to the operator. Hot-links can provide access to web sites or local information such as help, maintenance procedures, training, etc.

The graphical user interface can be provided with the capability to make views semi-transparent to prevent views at the top of the screen from completely obscuring views underneath. The graphical user interface can be provided with the capability to zoom in or zoom out to provide details for selected items, rather than requiring the operator to select a lower level "details screen". The graphical user interface can be provided with widgets to allow the operator to move small windows around the screen for customizing displays (such as a clock, or test counter, etc.). The graphical user interface can be provided with the capability to view and interact with a graphical depiction of the instrument. The area under a cursor can be highlighted and/or magnified for selection, information, zoomed viewing, etc. The graphical user interface can have instructional pop-up balloons for providing details and/or information for selected items, rather than requiring the operator to select a lower level "details screen" or "help screen". The graphical user interface can be equipped with fuel gauge-type icons to quickly indicate low levels of consumable items and/or reagents. A touch screen can be used to allow an alternative for a keyboard and/or a mouse.

Figure 24:
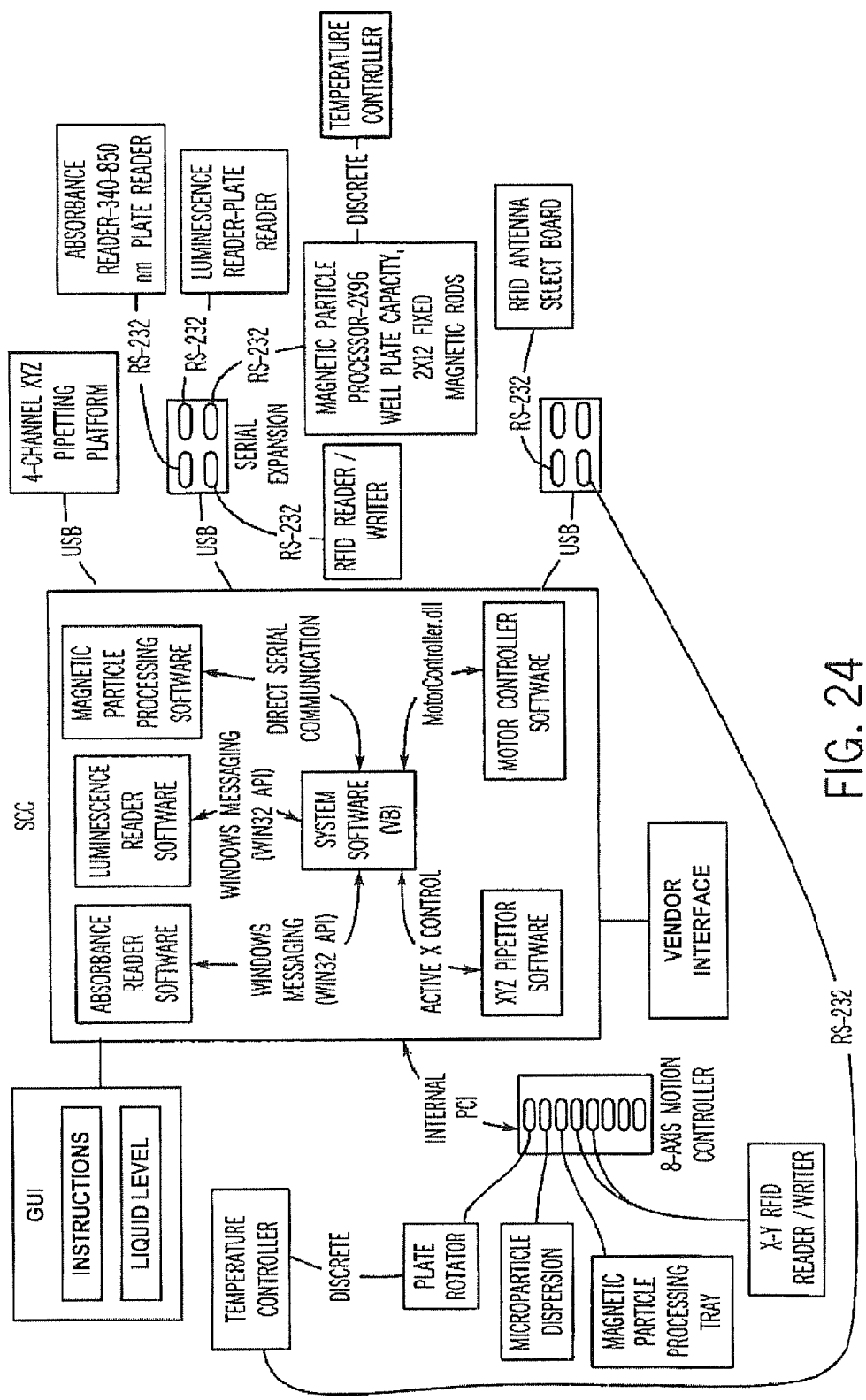
FIG. 24 is a schematic diagram illustrating computer interfaces for controlling the laboratory automation system described herein.

The components illustrated in FIG. 24 include a software module for absorbance readers, software for luminescence readers, software for magnetic particle processing, software for motor controllers, and software for dispensing devices. The foregoing programs are connected to the system software. The components also include appropriate connectors for interconnecting the aforementioned software.

Other components illustrated in FIG. 24 that are connected to the software module include an 8-axis motion controller, which is used to control the micro-well plate rotator, the apparatus for dispersing microparticles, the magnetic particle processing tray, and the radio frequency reader/writer, which can move in two directions in one plane. A temperature controller is connected to the plate rotator. The components also include appropriate electrical connectors for connecting to the aforementioned software module.

Still other components illustrated in FIG. 24 that can be connected to the software module include at least one radio frequency identification antenna section board, at least one radio frequency identification reader/writer, at least one magnetic particle processor, at least one luminescence reader, at least one absorbance reader, at least one dispensing device platform. A temperature controller is connected to the at least one magnetic particle processor. The components also include appropriate electrical connectors for connecting to the aforementioned software module. It should be noted that the system does not require both at least one radio frequency identification antenna section board and at least one radio frequency identification reader/writer. One or the other or both of the foregoing radio frequency identification components can be used.

The components illustrated in FIG. 24 are commercially available and are capable of being connected in a proper manner by one having ordinary skill in the art.

The operator or laboratory information system will download test orders to the system, for samples that will eventually be presented to the system for testing.

The operator or a system for managing the inventory of reagents will load the required consumables on to the system. The operator or the laboratory automation system will present the required samples to the system. The system will determine and report the analyte (i.e., antigen or antibody) in a sample, according to the downloaded test order for that sample. The operator or the laboratory automation system will remove the samples from the system. The operator or the laboratory information system will review/release test results to the origin of the test order.

The apparatus and method described herein allow a reduction in volume of reaction mixture, volume of reagent, volume of liquid waste, and resultant assay costs by performing assays within a micro-well plate. The apparatus and method described herein allow an improvement in readable sensitivity of five (5) times (compared to existing analyzers with translucent reaction vessels), by using micro-well plates for reading chambers. The apparatus and method described herein allows the consolidation of workflow, the complete integration of immunoassay and clinical chemistry processing, and increased efficiency of resources by utilizing similar consumable materials, modular subsystems, and different assay technologies within one system, by using an aspirating/dispensing device and performing assays within a micro-well plate.

The apparatus and method described herein enable immunoassays to be integrated with clinical chemistry assays by using many of the same resources, such as, for example, pipettes, kitting stations, fluidics, refrigeration equipment, controllers, power supply, that can be used for both types of assays.

The apparatus and method described herein allows resultant analyzers to be smaller, more reliable, and less complex than existing analyzers, by performing assays within a micro-well plate, using an aspirating/dispensing device.

The apparatus and method described herein allow new assays protocols to be accommodated with minimal effect on analyzer design, by using an aspirating/dispensing device and micro-well plates.

The use of micro-well plates facilitates miniaturization, smaller system footprint, and bench-top implementation.

Micro-well plates enable the use of simpler mechanisms and fewer mechanisms, thereby lowering the cost of the system over its life and increasing reliability.

The aspirating/dispensing device and micro-well plates facilitate new protocols, and new timing requirements for these protocols The laboratory automation system can be rearranged and scaled by using modular subsystems as building blocks (for new assays) that can be added or subtracted from the aspirating/dispensing device.

Micro-well plate washers are available; consequently the micro-well plates can be re-used.

The invention enables chain of custody techniques/checks, kitting of reaction vessels, and management of consumable items and disposable items that span a multiplicity of diagnostic testing technologies within a centralized control and resource scheduling design.

For clinical chemistry assays, mixing of the reaction mixtures can be carried out by shaking the micro-well plate, compared to the invasive mixing procedure performed on the ARCHITECT® apparatus. Absorbance reading is performed with a sweeping photodiode array and stationary source, compared with the moving cuvette method performed on the ARCHITECT® apparatus. Incubation is performed on the entire clinical chemistry micro-well plate.

For immunoassays, the separation, washing, and mixing can be performed by means of magnetic rods encased in sleeves. This manner of separation, washing, and mixing stands in contrast to the moving cuvettes, process path magnets, direct aspirating/dispense, and in-track vortexing methods performed on the ARCHITECT® apparatus. Incubation is performed on the entire micro-well plate in which the immunoassay is conducted. The magnetic microparticles remain in a micro-well during the complete incubation period. Even though the immunoassays are performed by moving and incubating the microparticles through microwells of the sample, the wash buffer, the conjugate, and the pre-trigger solutions, immunoassays can continue to processed according to the fundamental procedure used for immunoassays performed on the ARCHITECT® apparatus.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A laboratory automation system to perform clinical chemistry assays and immunoassays on a plurality multi-well plates, the system comprising:
    an immunoassay module configured to perform immunoassays on a first multi-plate, the immunoassay module including:
        an incubator:
        a luminescence reader; and
        a magnetic particle processor to mix and wash contents of the first multi-well plate;
    a clinical chemistry assay module configured to perform clinical chemistry assays on a second multi-well plate, the clinical chemistry assay module including:
        an absorbance reader;
        a mixer; and
        an incubator;
    an extraction module configured to extract a nucleic acid from a biological sample and to amplify the extracted nucleic acid;
    a reagent storage module including a first reagent and a second reagent;
    a common platform supporting the immunoassay module, the clinical chemistry assay module, and the extraction module;
    a multi-well plate storage module disposed on the platform, the multi-well plate storage module including a plurality of storage areas for storing the plurality of multi-well plates;
    an aspirating/dispensing device; and
    a controller configured to:
        control the aspirating/dispensing device to kit the first multi-well plate by dispensing sample into the first multi-well plate and dispensing the first reagent into the first multi-well plate for an immunoassay analysis;
        control the immunoassay module to analyze contents of one or more wells of the first multi-well plate by mixing, incubating, washing and reading the contents of the one or more of wells of the first multi-well plate;
        control the aspirating/dispensing device to kit the second multi-well kit for a clinical chemistry assay analysis while the first multi-well plate is being analyzed by the immunoassay module, the aspirating/dispensing device to kit the second multi-well plate by dispensing sample into the second multi-well plate and dispensing the second reagent into the second multi-well plate; and
        control the clinical chemistry assay module to analyze contents of one or more wells of the second multi-well plate by mixing, incubating and reading the contents of the one or more wells of the second multi-well plate while the first multi-well plate is being analyzed by the immunoassay module.

2. The laboratory automation system of claim 1, wherein the controller is further configured to control the immunoassay module to perform about two to about twenty-four immunoassays in the magnetic particle processor simultaneously.

3. The laboratory automation system of claim 1, wherein the controller is further configured to control the immunoassay module to perform about two to about 96 immunoassays in the magnetic particle processor simultaneously.

4. The laboratory automation system of claim 1 further comprising troughs having bulk liquids including at least one of a pre-trigger solution, a washer buffer or deionized water.

5. The laboratory automation system of claim 1, wherein the magnetic particle processor is a first magnetic particle processor, the extraction module including a second magnetic particle processor.

6. The laboratory automation system of claim 1, wherein the controller is further configured to vary one or more of a duration of incubation, a duration of mixing, a duration of reagent addition steps or a duration of washing of contents of one or more of the wells of the first multi-well plate.

7. The laboratory automation system of claim 1 further including a sample container, wherein the controller is further configured to control the aspirating/dispensing device to aspirate a liquid from the sample container and dispense the liquid into one or more of the first multi-well plate or the second multi-well plate.

8. The laboratory automation system of claim 1, wherein the reagent
storage module includes a first reagent container with the first reagent for the immunoassay module and a second reagent container with the second reagent for the clinical chemistry assay module.

9. The laboratory automation system of claim 8, wherein the aspirating/dispensing includes a transport mechanism and is to move one or more of a sample container, the first reagent container or the second reagent container via the transport mechanism.

10. The laboratory automation system of claim 9, wherein the luminescence reader is located outside of the magnetic particle processor, and wherein the controller is further configured to control the aspirating/dispensing device to transfer the first multi-well plate from the magnetic particle processor into the luminescence reader via the transport mechanism.

11. The laboratory automation system of claim 1 further comprising a plate rotator to rotate the second multi-well plate before processing in the clinical chemistry assay module.

12. The laboratory automation system of claim 1, wherein the controller is further configured to control the aspirating/dispensing device to kit the first multi-well plate and the second multi-well plate with the same sample.

13. The laboratory automation system of claim 1, wherein the immunoassay module comprises a chemiluminescent microparticle processor.

14. The laboratory automation system of claim 1 further comprising a second immunoassay module and a third multi-well plate, wherein the controller is configured to control the aspirating/dispensing device to kit the third multi-well plate for analysis by the second immunoassay module.

15. The laboratory automation system of claim 1, wherein the immunoassay module is located at a first location in the laboratory automation system and the clinical chemistry assay module is located at a second location in the laboratory automation system, the second location different from the first location.

16. The laboratory automation system of claim 1, wherein the kitting of the first multi-well plate is to be carried out prior to entry of the first multi-well plate into the immunoassay module and the kitting of the second multi-well plate is to be carried out prior to entry of the second multi-well plate into the clinical chemistry assay module.

17. The laboratory automation system of claim 1, wherein the luminescence reader is separate from the magnetic particle processor, the luminescence reader to read reaction mixtures in one or more of the wells of the first multi-well plate, wherein the first multi-well plate is to be transferred into the luminescence reader after processing in the magnetic particle processor.

18. The laboratory automation system of claim 17, wherein the controller is further configured to control the luminescence reader to read the reaction mixtures in one or more of the wells of the first multi-well plate while the absorbance reader is to read reaction mixtures in one or more of the wells of the second multi-well plate.

19. The laboratory automation system of claim 1 further comprising an automated robotic mechanism to transfer at least one of a reagent container or sample container from a refrigerated storage area to the immunoassay module, the clinical chemistry assay module or the extraction module of the laboratory automation system.

20. The laboratory automation system of claim 1 further comprising one or more immunoassay modules, clinical chemistry assay modules or extraction modules that are capable of being one or more of added to, subtracted from or rearranged.

21. The laboratory automation system of claim 1 further comprising a system for controlling evaporation of reagents by means of a plurality of sliding covers.

22. The laboratory automation system of claim 1, wherein, to control the clinical chemistry assay module to analyze the contents of one or more wells of the second multi-well plate, the controller is further configured to control the aspirating/dispensing device to dispense the second reagent or a third reagent into one or more wells of the second multi-well plate between readings by the absorbance reader.

* * * * *